US010167295B2

(12) United States Patent
Levine et al.

(10) Patent No.: US 10,167,295 B2
(45) Date of Patent: Jan. 1, 2019

(54) ANALGESIC COMPOUNDS AND METHODS OF USE

(71) Applicant: The Regents of the University of California, Oakland, CA (US)

(72) Inventors: Jon D. Levine, San Francisco, CA (US); Alejandra Gallardo-Godoy, Brisbane (AU)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/851,248

(22) Filed: Sep. 11, 2015

(65) Prior Publication Data

US 2016/0068541 A1 Mar. 10, 2016

Related U.S. Application Data

(63) Continuation of application No. PCT/US2014/031089, filed on Mar. 18, 2014.

(60) Provisional application No. 61/792,462, filed on Mar. 15, 2013.

(51) Int. Cl.

| C07D 401/06 | (2006.01) |
| C07D 403/12 | (2006.01) |
| C07D 405/12 | (2006.01) |
| C07D 405/14 | (2006.01) |
| C07D 491/107 | (2006.01) |
| C07D 489/02 | (2006.01) |
| C07D 207/09 | (2006.01) |
| C07D 211/06 | (2006.01) |
| C07D 207/06 | (2006.01) |
| C07D 207/263 | (2006.01) |
| C07D 211/12 | (2006.01) |
| C07D 489/00 | (2006.01) |

(52) U.S. Cl.
CPC ....... *C07D 491/107* (2013.01); *C07D 207/06* (2013.01); *C07D 207/09* (2013.01); *C07D 207/263* (2013.01); *C07D 211/06* (2013.01); *C07D 211/12* (2013.01); *C07D 401/06* (2013.01); *C07D 403/12* (2013.01); *C07D 405/12* (2013.01); *C07D 405/14* (2013.01); *C07D 489/00* (2013.01); *C07D 489/02* (2013.01)

(58) Field of Classification Search
None
See application file for complete search history.

(56) References Cited

U.S. PATENT DOCUMENTS

| 4,801,604 A | 1/1989 | VonVoightlander et al. |
| 4,861,760 A | 8/1989 | Mazuel et al. |
| 4,911,920 A | 3/1990 | Jani et al. |
| 5,212,162 A | 5/1993 | Missel et al. |
| 5,403,841 A | 4/1995 | Lang et al. |
| 5,739,158 A | 4/1998 | De Costa et al. |
| 2003/0144272 A1* | 7/2003 | Kumar ................ A61K 31/404 514/217.12 |
| 2005/0038060 A1 | 2/2005 | Ando et al. |

FOREIGN PATENT DOCUMENTS

| WO | WO-2004110996 A1 * | 12/2004 | ........... C07D 207/08 |
| WO | WO-2014/146111 A2 | 9/2014 | |
| WO | WO-2014/146111 A3 | 9/2014 | |

OTHER PUBLICATIONS

Dorwald F. A. Side Reactions in Organic Synthesis, 2005, Wiley: VCH, Weinheim p. IX of Preface p. 1-15.*
Pirrung "Handbook of Synthetic Organic Chemistry" Second Edition, Academic Press: San Diego, 2017.*
Pitt "Heteroaromatic Rings of the Future" J. Med. Chem. 2009, 52, 2952-2963.*
Bilke, J.L. et al. (Aug. 15, 2008, e-published Jul. 19, 2008). "On the two-ligand catalytic asymmetric deprotonation of N-boc pyrrolidine: probing the effect of the stoichiometric ligand," *J Org Chem* 73(16):6452-6454.
Commiskey, S. et al. (Jun. 2005, e-published Jun. 8, 2005). "Butorphanol: effects of a prototypical agonist-antagonist analgesic on kappa-opioid receptors.," *J Pharmacol Sci* 98(2):109-116.
International Search Report dated Sep. 19, 2014, for PCT Application No. PCT/US2014/031089, filed on Mar. 18, 2014, 4 pages.
Levine, J.D. et al. (Nov. 1988). "Potentiation of pentazocine analgesia by low-dose naloxone," *J Clin Invest* 82(5):1574-1577.
Negus, S.S. et al. Sep. 1999). "Opioid antinociception in ovariectomized monkeys: comparison with antinociception in males and effects of estradiol replacement," *J Pharmacol Exp Ther* 290(3):1132-1140.
Rizzi, A. et al. (Sep. 2006, e-published May 11, 2006). "Endogenous nociceptin/orphanin FQ signalling produces opposite spinal antinociceptive and supraspinal pronociceptive effects in the mouse formalin test: pharmacological and genetic evidences," *Pain* 124(1-2):100-108.
Written Opinion dated Sep. 19, 2014, for PCT Application No. PCT/US2014/031089, filed on Mar. 18, 2014, 6 pages.
Zhu, J. et al. (Aug. 1997). "Activation of the cloned human kappa opioid receptor by agonists enhances [35S]GTPgammaS binding to membranes: determination of potencies and efficacies of ligands," *J Pharmacol Exp Ther* 282(2):676-684.
Chien, C.C. et al. Dec. 1994). "Selective antagonism of opioid analgesia by a sigma system," *J Pharmacol Exp Ther* 271(3):1683-1590.
Fillingim, R.B. et al. (May 2004). "Experimental pain models reveal no sex differences in pentazocine analgesia in humans," *Anesthesiology* 100(5):1263-1270.
Gear, R.W. et al. (Nov. 1996). "Kappa-opioids produce significantly greater analgesia in women than in men," *Nat Med* 2(11):1248-1250.

(Continued)

*Primary Examiner* — Zinna Northington Davis
(74) *Attorney, Agent, or Firm* — Mintz Levin Cohn Ferris Glovsky and Popeo, P.C.

(57) ABSTRACT

Provided herein, inter alia, are methods and compositions for achieving an analgesic effect in subjects in need thereof.

6 Claims, 16 Drawing Sheets

(56) References Cited

OTHER PUBLICATIONS

Gear, R.W. et al. (Nov. 1999). "The kappa opioid nalbuphine produces gender- and dose-dependent analgesia and antianalgesia in patients with postoperative pain," *Pain* 83(2):339-345.

Gear, R.W. et al. (2000). "Action of Naloxone on Gender-Dependent Analgesic and Antianalgesic Effects of Nalbuphine in Humans," *The Journal of Pain* 1(2):122-127.

Gear, R.W. et al. (Nov. 6, 2003). "Dose ratio is important in maximizing naloxone enhancement of nalbuphine analgesia in humans," *Neurosci Lett* 351(1):5-8.

Gear, R.W. et al. (Mar. 2006). "Neuroleptics antagonize nalbuphine antianalgesia," *J Pain* 7(3):187-191.

Gear, R.W. et al. (Jan. 17, 2014, e-published Nov. 1, 2013). "NOP receptor mediates anti-analgesia induced by agonist-antagonist opioids," *Neuroscience* 257:139-148.

Gordon, N. C. et al. (Nov. 1995). "Enhancement of morphine analgesia by the GABAB agonist baclofen," *Neuroscience* 69(2):345-349.

Khasar, S.G. et al. (2003). "Absence of nalbuphine anti-analgesia in the rat," *Neurosci Lett* 345(3):165-168.

Kshirsagar, S. et al. (Feb. 2008, e-published Oct. 18, 2007). "A mechanistic model for the sex-specific response to nalbuphine and naloxone in postoperative pain," *J Pharmacokinet Pharmacodyn* 35(1):69-83.

Levine, J.D. et al. (Jun. 1988). "Synergism between the analgesic actions of morphine and pentazocine," *Pain* 33(3):369-372.

Mogil, J.S. et al. (Nov. 1996). "Orphanin FQ is a functional anti-opioid peptide," *Neuroscience* 75(2):333-337.

Suaudeau, C. et al. (1998). "Nociceptin-induced apparent hyperalgesia in mice as a result of the prevention of opioid autoanalgesic mechanisms triggered by the stress of an intracerebroventricular injection,"*Fundam Clin Pharmacol* 12(4):420-425.

Coldham, I. et al. (Apr. 6, 2010). "Asymmetric substitutions of 2-lithiated N-boc-piperidine and N-Boc-azepine by dynamic resolution," *Chemistry* 16(13):4082-4090.

Gonzalez-Sabin, J. et al. (Nov. 5, 2004). "Chemoenzymatic preparation of optically active trans-cyclohexane-1,2-diamine derivatives: an efficient synthesis of the analgesic U-(-)-50,488," *Chemistry* 10(22):5788-5794.

Clark et al, Highly selective kappa opioid analgesics. Synthesis and structure-activity relationships of novel N-[(2-aminocyclohexyl)aryl]acetamide and N-[(2-aminocyclohexyl)aryloxy]acetamide derivatives, J. Med. Chem., 31(4):831-836 (1988).

Montalbetti et al, Amide bond formation and peptide coupling, Tetrahedron, 61:10827-10852 (2005).

Valeur et al, Amide bond formation: beyond the myth of coupling reagents, Chemical Society Reviews, 38:606-631 (2009).

\* cited by examiner

ANALGESIC COMPOUNDS AND METHODS OF USE

CROSS-REFERENCE TO RELATED APPLICATIONS

This application claims the benefit of U.S. Provisional Application No. 61/792,462 filed Mar. 15, 2013, which is hereby incorporated in its entirety and for all purposes.

STATEMENT AS TO RIGHTS TO INVENTIONS MADE UNDER FEDERALLY SPONSORED RESEARCH AND DEVELOPMENT

This invention was made with government support under grant DE018526 awarded by the National Institutes of Health. The Government has certain rights in the invention.

BACKGROUND

Pain represents a major health and economic problem throughout the world. Despite advances in understanding the physiological basis of pain, an ideal analgesic has yet to be discovered. Among analgesic drugs, the opioid class of compounds is widely used for pain treatment. The opioid drugs produce effects by interacting with the opioid receptors. The existence of at least three opioid receptor types, μ (mu), δ (delta), and κ (kappa) has been established. All three opioid receptor types are located in the human peripheral and central nervous system, and each has a role in the mediation of pain.

Opioid compounds have opium or morphine-like properties and are primarily used to treat pain, but may have other pharmacological effects including drowsiness, respiratory depression, and constipation, as well as abuse potential and tolerance. Opioid agonists include compounds that bind to an opioid receptor thereby forming a complex which elicits pharmacological responses particular to the nature of the receptor. Kappa (.kappa.)-opioid receptor agonists include compounds that induce analgesia predominantly by acting on kappa-opioid receptors. Examples of kappa-opioid agonists include nalbuphine, pentazocine, butorphanol, benzomorphan, and benzacetamide, phenothiazine, thiazine, and benzodiazepine derivatives.

Opioid antagonists include compounds that pharmacologically block or reverse all (or substantially all) the effects of opioid agonists. Non-selective opioid antagonists include those antagonists that act at least on kappa, mu, and delta opioid receptors. Opioid antagonists are generally used to reverse the effects of opioid agonist overdose and treatment of opioid addiction. Examples of opioid antagonists include naloxone, naltrexone, methylnaltrexone and nalmefene.

Morphine and related opioids currently used as analgesics produce their effect primarily through their agonist action at mu opioid receptors. The administration of these drugs is limited by significant side effects such as the development of tolerance, physical dependence, addiction liability, constipation, respiratory depression, muscle rigidity, and emesis. Kappa (κ)-type agonist-antagonist opioid analgesics (e.g. nalbuphine, pentazocine, and butorphanol) are known, but are considered weak analgesics compared to μ-opioids such as morphine or oxycodone. In addition, clinical studies have shown that kappa-type agonist-antagonist opioid analgesics (agonist-antagonists) produce a delayed-onset anti-analgesia in men but not women, an effect blocked by co-administration of a low dose of naloxone. Therefore, there is a need in the art for effective analgesic compounds that do not possess anti-analgesic (e.g. pain enhancing) properties, especially in men. Provided herein are compounds and methods addressing these and other needs in the art.

BRIEF SUMMARY

Provided herein, inter alia, are methods and compositions providing a new modality in the treatment pain in human subjects, particularly male human subjects. It has been demonstrated that anti-analgesic activity (e.g. pain enhancing) of opioid receptor agonist-antagonists (e.g. κ-agonist-antagonists) is facilitated by the nociceptin receptor or NOP receptor. Thus, provided herein, inter alia, are compounds and methods useful in achieving an analgesic effect through opioid receptor agonism (e.g. mu opioid receptor agonism, kappa opioid receptor agonism and/or delta opioid receptor agonism) while avoiding or decreasing anti-analgesic (e.g. pain enhancing) effects mediated by the NOP receptor.

In one aspect, provided herein is a compound or pharmaceutically acceptable salt thereof, having the formula:

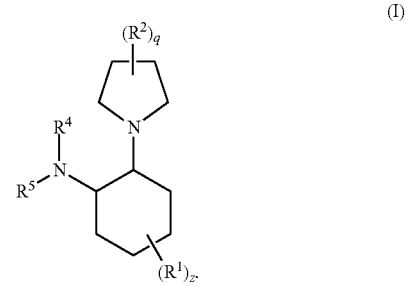

(I)

In Formula (I), q is an integer from 0 to 4 and z is an integer from 0 to 4. $R^1$, $R^2$ and $R^4$ are independently hydrogen, halogen, $-N_3$, $-CF_3$, $-CCl_3$, $-OH$, $-SH$, $-NH_2$, $-C(O)NH_2$, $-C(O)OH$, $-CN$, $-NO_2$, $-NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^4$ and $R^5$ are optionally joined together to form a substituted or unsubstituted heterocycloalkyl or substituted or unsubstituted heteroaryl. Alternatively, $R^5$ is $-C(O)-L^1-R^3$ or $R^3$-substituted or unsubstituted alkyl. $L^1$ is a bond or substituted or unsubstituted alkylene. $R^3$ is substituted or unsubstituted cycloalkyl, substituted or unsubstituted heterocycloalkyl, substituted or unsubstituted aryl or substituted or unsubstituted heteroaryl.

In another aspect, provided herein is a compound, or pharmaceutically acceptable salt thereof, having the formula:

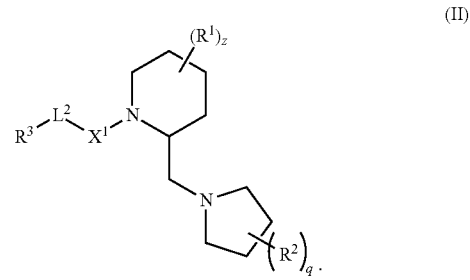

(II)

In Formula (II), q is an integer from 0 to 4 and z is an integer from 0 to 4. $X^1$ is —C(O)— or substituted or unsubstituted alkylene. $L^2$ is a bond, —N(H)—C(O)—, —C(O)— or substituted or unsubstituted alkylene. $R^1$ and $R^2$ are independently hydrogen, halogen, —$N_3$, —$CF_3$, —$CCl_3$, —OH, —SH, —$NH_2$, —C(O)$NH_2$, —C(O)OH, —CN, —$NO_2$, —$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^3$ is substituted or unsubstituted cycloalkyl, substituted or unsubstituted heterocycloalkyl, substituted or unsubstituted aryl or substituted or unsubstituted heteroaryl.

In another aspect, provided herein is a compound, or pharmaceutically acceptable salt thereof, having the formula:

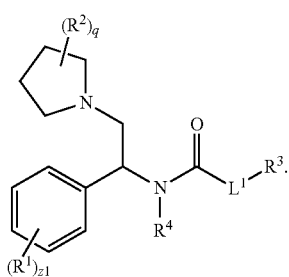

(III)

In Formula (III), q is an integer from 0 to 4 and z1 is an integer from 0 to 5. $R^1$ and $R^2$ are independently hydrogen, halogen, —$N_3$, —$CF_3$, —$CCl_3$, —OH, —SH, —$NH_2$, —C(O)$NH_2$, —C(O)OH, —CN, —$NO_2$, —$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $L^1$ is a bond or substituted or unsubstituted alkylene. $R^3$ is substituted or unsubstituted cycloalkyl, substituted or unsubstituted heterocycloalkyl, substituted or unsubstituted aryl or substituted or unsubstituted heteroaryl.

In another aspect, provided herein is a compound, or pharmaceutically acceptable salt thereof, having the formula:

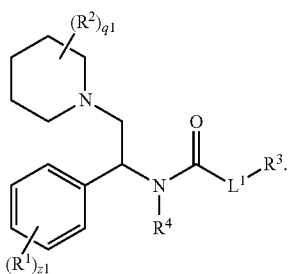

(IV)

In Formula (IV), q1 is an integer from 0 to 5 and z1 is an integer from 0 to 5. $R^1$ and $R^2$ are independently hydrogen, halogen, —$N_3$, —$CF_3$, —$CCl_3$, —OH, —SH, —$NH_2$, —C(O)$NH_2$, —C(O)OH, —CN, —$NO_2$, —$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $L^1$ is a bond or substituted or unsubstituted alkylene. $R^3$ is substituted or unsubstituted cycloalkyl, substituted or unsubstituted heterocycloalkyl, substituted or unsubstituted aryl or substituted or unsubstituted heteroaryl.

In another aspect, a method of inhibiting a nociceptin (NOP) receptor is provided. The method includes contacting a NOP receptor with an effective amount of a compound provided herein thereby inhibiting the NOP receptor.

In another aspect, a method of activating an opioid receptor is provided. The method includes contacting an opioid receptor with an effective amount of a compound provided herein thereby activating the opioid receptor. The opioid receptor is typically a delta opioid receptor, a kappa opioid receptor or a mu opioid receptor.

In another aspect, a method is provided for treating pain in a subject in need thereof. The method includes administering to the subject a therapeutically effective amount of a compound provided herein.

In another aspect, a method of determining whether a test compound elicits an analgesic effect in a human male subject and does not elicit an anti-analgesic (e.g. pain enhancing) effect in a human male subject is provided. The method includes (a) administering a test compound to a human male subject, (b) determining whether the test compound elicits an analgesic effect in the human male subject at a first time point and (c) determining whether the test compound elicits an anti-analgesic (e.g. pain enhancing) effect in the human male subject at a second time point thereby determining whether a test compound elicits an analgesic effect in a human male subject and does not elicit an anti-analgesic (e.g. pain enhancing) effect in a human male subject.

In another aspect, a method of determining whether a test compound elicits an analgesic effect in a mammal and does not elicit an anti-analgesic (e.g. pain enhancing) effect in mammal is provided. The method includes (a) administering a test compound to a mammal, (b) determining whether the test compound elicits an analgesic effect in the mammal at a first time point and (c) determining whether the test compound elicits an anti-analgesic (e.g. pain enhancing) effect in the mammal at a second time point thereby determining whether a test compound elicits an analgesic effect in a mammal and does not elicit an anti-analgesic (e.g. pain enhancing) effect in a mammal.

DETAILED DESCRIPTION

Definitions

Figure 1:
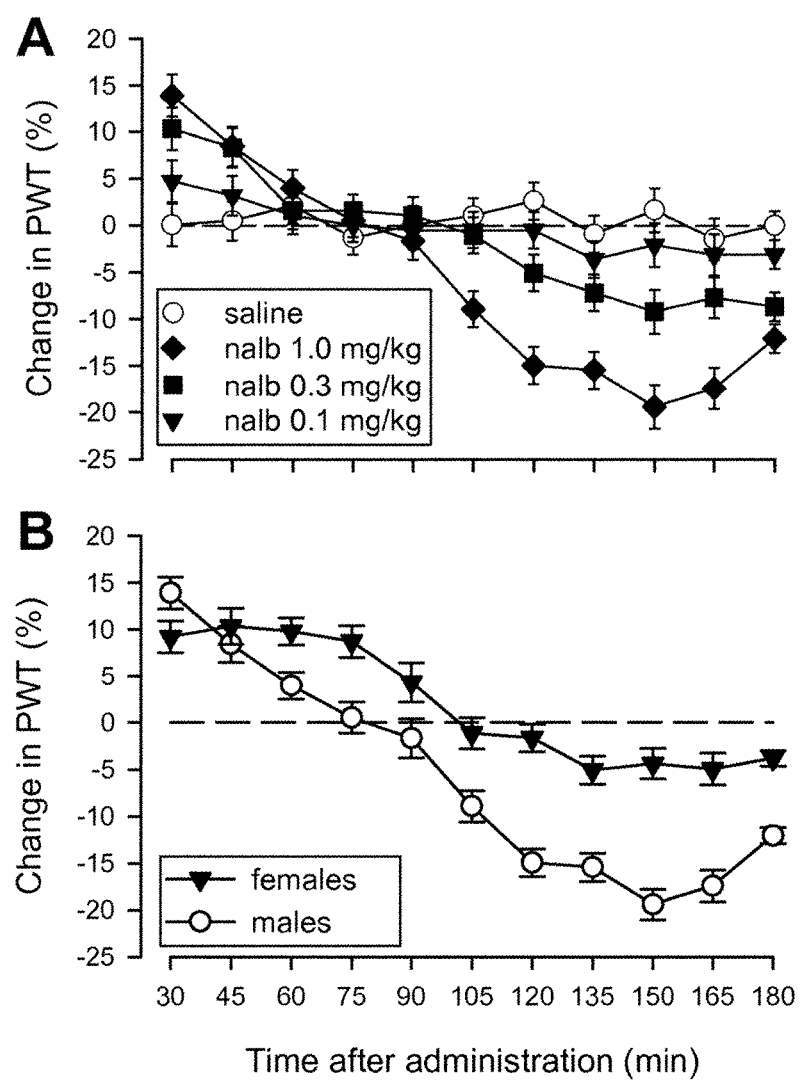
FIG. 1. Nalbuphine in the rat. A. Groups of male rats were administered nalbuphine (nalb 0.1, 0.3, and 1.0 mg/kg i.v.) or saline (i.v.). Nalbuphine (1 mg/kg) produced both analgesia and anti-analgesia. The onset of anti-analgesia began ~90 minutes after its administration, became significant at 120 minutes, and persisted through the remainder of the 180 minute experiment. B. In female rats, nalbuphine 1 mg/kg produced only analgesia. Data for males is replotted from FIG. 1A. In this and subsequent figures, data are plotted as mean±SEM; analgesia is defined as mechanical nociceptive threshold significantly above baseline; anti-analgesia is defined as threshold significantly below baseline.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of heteroaryl groups include pyridinyl, pyrimidinyl, thiophenyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —NO$_2$, in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R''', and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —$CO_2$R', —CONR'R", —OC(O) NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —NR'NR"R''', —ONR'R", —NR'C=(O)NR"R'''R'''', —CN, —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R''', and R'''' groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —$CF_3$, —CN, —OH, —$NH_2$, —COOH, —$CONH_2$, —$NO_2$, —SH, —$SO_2$Cl, —$SO_3$H, —$SO_4$H, —$SO_2NH_2$, —$NHNH_2$, —$ONH_2$, —NHC=(O)$NHNH_2$, —NHC=(O) $NH_2$, —$NHSO_2$H, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, halogen, —$CF_3$, —CN, —OH, —$NH_2$, —COOH, —$CONH_2$, —$NO_2$, —SH, —$SO_2$Cl, —$SO_3$H, —$SO_4$H, —$SO_2NH_2$, —$NHNH_2$, —$ONH_2$, —NHC=(O)$NHNH_2$, —NHC=(O)$NH_2$, —$NHSO_2$H, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, halogen, —$CF_3$, —CN, —OH, —$NH_2$, —COOH, —$CONH_2$, —$NO_2$, —SH, —$SO_2$Cl, —$SO_3$H, —$SO_4$H, —$SO_2NH_2$, —$NHNH_2$, —$ONH_2$, —NHC=(O)$NHNH_2$, —NHC=(O)$NH_2$, —$NHSO_2$H, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, halogen, —$CF_3$, —CN, —OH, —$NH_2$, —COOH, —$CONH_2$, —$NO_2$, —SH, —$SO_2$Cl, —$SO_3$H, —$SO_4$H, —$SO_2NH_2$, —$NHNH_2$, —$ONH_2$, —NHC=(O)$NHNH_2$, —NHC=(O)$NH_2$, —$NHSO_2$H, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the present invention, whether radioactive or not, are encompassed within the scope of the present invention.

The symbol "〰" denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Where a moiety is substituted with an R substituent, the group may be referred to as "R-substituted." Where a moiety is R-substituted, the moiety is substituted with at least one R substituent and each R substituent is optionally different. For example, where a moiety herein is $R^{12}$-substituted or unsubstituted alkyl, a plurality of $R^{12}$ substituents may be attached to the alkyl moiety wherein each $R^{12}$ substituent is optionally different. Where an R-substituted moiety is substituted with a plurality R substituents, each of the R-substituents may be differentiated herein using a prime symbol (') such as R', R", etc. For example, where a moiety is $R^{12}$-substituted or unsubstituted alkyl, and the moiety is substituted with a plurality of $R^{12}$ substituents, the plurality of $R^{12}$ substituents may be differentiated as $R^{12'}$, $R^{12''}$, $R^{12'''}$, etc. In embodiments, the plurality of R substituents is 3. In embodiments, the plurality of R substituents is 2.

In embodiments, a compound as described herein may include multiple instances of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and/or other variables. In such embodiments, each variable may optional be different and be appropriately labeled to distinguish each group for greater clarity. For example, where each $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, and/or $R^{21}$, is different, they may be referred to, for example, as $R^{1.1}$, $R^{1.2}$, $R^{1.3}$, $R^{1.4}$, $R^{2.1}$, $R^{2.2}$, $R^{2.3}$, $R^{2.4}$, $R^{3.1}$, $R^{3.2}$, $R^{3.3}$, $R^{3.4}$, $R^{4.1}$, $R^{4.2}$, $R^{4.3}$, $R^{4.4}$, $R^{5.1}$, $R^{5.2}$, $R^{5.3}$, $R^{5.4}$, $R^{6.1}$, $R^{6.2}$, $R^{6.3}$, $R^{6.4}$, $R^{7.1}$, $R^{7.2}$, $R^{7.3}$, $R^{7.4}$, $R^{8.1}$, $R^{8.2}$, $R^{8.3}$, $R^{8.4}$, $R^{9.1}$, $R^{9.2}$, $R^{9.3}$, $R^{9.4}$, $R^{10.1}$, $R^{10.2}$, $R^{10.3}$, $R^{10.4}$, $R^{11.1}$, $R^{11.2}$, $R^{11.3}$, $R^{11.4}$, $R^{12.1}$, $R^{12.2}$, $R^{12.3}$, $R^{12.4}$, $R^{13.1}$, $R^{13.2}$, $R^{13.3}$, $R^{13.4}$, $R^{14.1}$, $R^{14.2}$, $R^{14.3}$, $R^{14.4}$, $R^{15.1}$, $R^{15.2}$, $R^{15.3}$, $R^{15.4}$, $R^{16.1}$, $R^{16.2}$, $R^{16.3}$, $R^{16.4}$, $R^{17.1}$, $R^{17.2}$, $R^{17.3}$, $R^{17.4}$, $R^{18.1}$, $R^{18.2}$, $R^{18.3}$, $R^{18.4}$, $R^{19.1}$, $R^{19.2}$, $R^{19.3}$, $R^{19.4}$, $R^{20.1}$, $R^{20.2}$, $R^{20.3}$, $R^{20.4}$, $R^{21.1}$, $R^{21.2}$, $R^{21.3}$, and/or $R^{21.4}$, respectively, wherein the definition of $R^1$ is assumed by $R^{1.1}$, $R^{1.2}$, $R^{1.3}$, and/or $R^{1.4}$, the definition of $R^2$ is assumed by $R^{2.1}$, $R^{2.2}$, $R^{2.3}$, and/or $R^{2.4}$, the definition of $R^3$ is assumed by $R^{3.1}$, $R^{3.2}$, $R^{3.3}$, and/or $R^{3.4}$, the definition of $R^4$ is assumed by $R^{4.1}$, $R^{4.2}$, $R^{4.3}$, and/or $R^{4.4}$, the definition of $R^5$ is assumed by $R^{5.1}$, $R^{5.2}$, $R^{5.3}$, and/or $R^{5.4}$, the definition of $R^6$ is assumed by $R^{6.1}$, $R^{6.2}$, $R^{6.3}$, and/or $R^{6.4}$, the definition of $R^7$ is assumed by $R^{7.1}$, $R^{7.2}$, $R^{7.3}$, and/or $R^{7.4}$, the definition of $R^8$ is assumed by $R^{8.1}$, $R^{8.2}$, $R^{8.3}$, and/or $R^{8.4}$, the definition of $R^9$ is assumed by $R^{9.1}$, $R^{9.2}$, $R^{9.3}$, and/or $R^{9.4}$, the definition of $R^{10}$ is assumed by $R^{10.1}$, $R^{10.2}$, $R^{10.3}$, and/or $R^{10.4}$, the definition of $R^{11}$ is assumed by $R^{11.1}$, $R^{11.3}$, and/or $R^{11.4}$, the definition of $R^{12}$ is assumed by $R^{12.1}$, $R^{12.2}$, $R^{12.3}$, and/or $R^{12.4}$, the definition of $R^{13}$ is assumed by $R^{13.1}$, $R^{13.2}$, $R^{13.3}$, and/or $R^{13.4}$, the definition of $R^{14}$ is assumed by $R^{14.1}$, $R^{14.2}$, $R^{14.3}$, and/or $R^{14.4}$, the definition of $R^{15}$ is assumed by $R^{15.1}$, $R^{15.2}$, $R^{15.3}$, and/or $R^{15.4}$, the definition of $R^{16}$ is assumed by $R^{16.1}$, $R^{16.2}$, $R^{16.3}$, and/or $R^{16.4}$, the definition of $R^{17}$ is assumed by $R^{17.1}$, $R^{17.3}$, and/or $R^{17.4}$, the definition of $R^{18}$ is assumed by $R^{18.1}$, $R^{18.2}$, $R^{18.3}$, and/or $R^{18.4}$, the definition of $R^{19}$ is assumed by $R^{19.1}$, $R^{19.2}$, $R^{19.3}$, and/or $R^{19.4}$, the definition of $R^{20}$ is assumed by $R^{20.1}$, $R^{20.2}$, $R^{20.3}$, and/or $R^{20.4}$, the definition of $R^{21}$ is assumed by $R^{21.1}$, $R^{21.2}$, $R^{21.3}$, and/or $R^{21.4}$. The variables used within a definition of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, and/or $R^{21}$, and/or other variables that appear at multiple instances and are different may similarly be appropriately labeled to distinguish each group for greater clarity.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of pain (e.g. from an injury, disease, pathology or condition), including any objective or subjective abatement parameters. Thus, the treatment or amelioration of pain can be based on objective or subjective parameters, including the results of a physical examination, neuropsychiatric exams, and/or a psychiatric evaluation.

An "effective amount" is an amount sufficient to accomplish a stated purpose (e.g. treat pain and/or impart an analgesic effect). An example of an "effective amount" is an amount sufficient to contribute to the treatment, prevention, or reduction of a symptom or symptoms pain, which could also be referred to as a "therapeutically effective amount." A "reduction" of a symptom or symptoms pain (and grammatical equivalents of this phrase) means decreasing of the severity or frequency of the symptom(s), or elimination of the symptom(s).

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein (e.g. receptor).

As defined herein, the term "inhibition", "inhibit", "inhibiting" and the like in reference to a receptor inhibitor (e.g. receptor antagonist) interaction means negatively affecting (e.g. decreasing) the activity or function of the receptor relative to the activity or function of the receptor in the absence of the inhibitor.

As defined herein, the term "activation", "activate", "activating" and the like in reference to a receptor activator (e.g. agonist) interaction means positively affecting (e.g. increasing) the activity or function of the receptor relative to the activity or function of the receptor in the absence of the "Patient" or "subject in need thereof" refers to a living organism suffering from or prone to a disease or condition that can be treated by administration of a compound or pharmaceutical composition, as provided herein. Non-limiting examples include humans, other mammals, bovines, rats, mice, dogs, monkeys, goat, sheep, cows, deer, and other non-mammalian animals. In some embodiments, a patient or subject is human.

"Disease" or "condition" refer to a state of being or health status of a patient or subject capable of being treated with a compound, pharmaceutical composition, or method provided herein.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. The compositions of the present invention can be delivered transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

Pharmaceutical compositions provided by the present invention include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result. Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

Compounds

In one aspect, provided herein is a compound, or pharmaceutically acceptable salt thereof, having the formula:

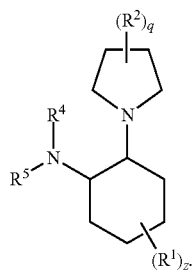

(I)

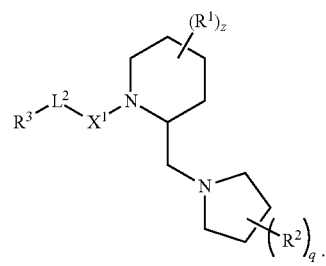

(II)

In Formula (I), q is an integer from 0 to 4 and z is an integer from 0 to 4. $R^1$, $R^2$ and $R^4$ are independently hydrogen, halogen, —$N_3$, —$CF_3$, —$CCl_3$, —OH, —SH, —$NH_2$, —C(O)$NH_2$, —C(O)OH, —CN, —$NO_2$, —$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^4$ and $R^5$ are optionally joined together to form a substituted or unsubstituted heterocycloalkyl or substituted or unsubstituted heteroaryl. Alternatively, $R^5$ is —C(O)-$L^1$-$R^3$ or $R^3$-substituted or unsubstituted alkyl. $L^1$ is a bond or substituted or unsubstituted alkylene. $R^3$ is substituted or unsubstituted cycloalkyl, substituted or unsubstituted heterocycloalkyl, substituted or unsubstituted aryl or substituted or unsubstituted heteroaryl.

In embodiments of Formula (I), the compound has the formula:

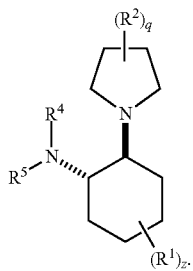

(IA)

In embodiments of Formula (I) and (IA), $R^4$ and $R^5$ are joined together to form a substituted or unsubstituted heteroaryl or substituted or unsubstituted heterocycloalkyl. For example, $R^4$ and $R^5$ may be joined together to form a substituted or unsubstituted fused ring heteroaryl or fused ring heterocycloalkyl (e.g. benzimidizolone).

In another aspect, provided herein is a compound, or pharmaceutically acceptable salt thereof, having the formula:

In Formula (II), q is an integer from 0 to 4 and z is an integer from 0 to 4. $X^1$ is —C(O)— or substituted or unsubstituted alkylene. $L^2$ is a bond, —N(H)—C(O)—, —C(O)— or substituted or unsubstituted alkylene. $R^1$ and $R^2$ are independently hydrogen, halogen, —$N_3$, —$CF_3$, —$CCl_3$, —OH, —SH, —$NH_2$, —C(O)$NH_2$, —C(O)OH, —CN, —$NO_2$, —$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^3$ is substituted or unsubstituted cycloalkyl, substituted or unsubstituted heterocycloalkyl, substituted or unsubstituted aryl or substituted or unsubstituted heteroaryl.

In embodiments of Formula (II), the compound has the formula:

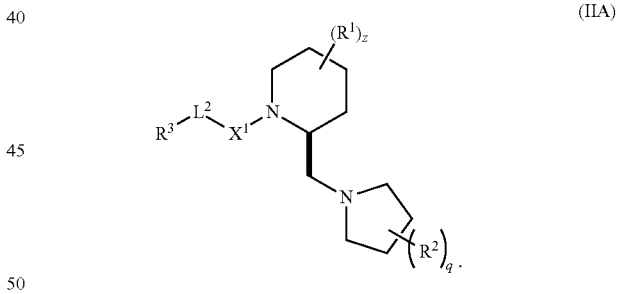

(IIA)

In embodiments of Formula (II) and (IIA), $X^1$ is —C(O)— or substituted or unsubstituted ($C_1$ to $C_3$) alkylene. $X^1$ may also be —C(O)— or unsubstituted ($C_1$ to $C_3$) alkylene. In embodiments, $X^1$ is —C(O)— or methylene. $X^1$ may also be —C(O)—.

$L^2$ may be a bond, —N(H)—C(O)—, —C(O)— or substituted or unsubstituted ($C_1$ to $C_3$) alkylene. $L^2$ may also be a bond, —N(H)—C(O)—, —C(O)— or unsubstituted ($C_1$ to $C_3$) alkylene. In embodiments, $L^2$ is a bond, —N(H)—C(O)—, —C(O)— or methylene. $L^2$ may also be a bond or methylene. In embodiments, $X^1$ is substituted or unsubstituted alkylene and $L^1$ is —N(H)—C(O)—.

In another aspect, provided herein is a compound, or pharmaceutically acceptable salt thereof, having the formula:

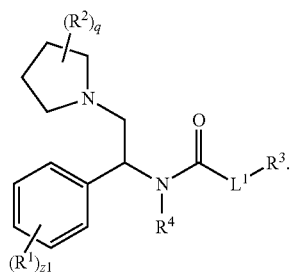
(III)

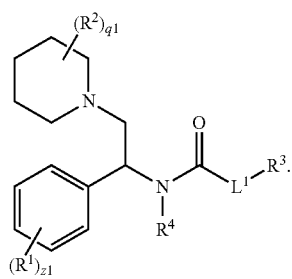
(IV)

In Formula (III), q is an integer from 0 to 4 and z1 is an integer from 0 to 5. $R^1$ and $R^2$ are independently hydrogen, halogen, —$N_3$, —$CF_3$, —$CCl_3$, —OH, —SH, —$NH_2$, —C(O)$NH_2$, —C(O)OH, —CN, —$NO_2$, —$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $L^1$ is a bond or substituted or unsubstituted alkylene. $R^3$ is substituted or unsubstituted cycloalkyl, substituted or unsubstituted heterocycloalkyl, substituted or unsubstituted aryl or substituted or unsubstituted heteroaryl.

In embodiments of Formula (III), the compound has the formula:

In Formula (IV), q1 is an integer from 0 to 5 and z1 is an integer from 0 to 5. $R^1$ and $R^2$ are independently hydrogen, halogen, —$N_3$, —$CF_3$, —$CCl_3$, —OH, —SH, —$NH_2$, —C(O)$NH_2$, —C(O)OH, —CN, —$NO_2$, —$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $L^1$ is a bond or substituted or unsubstituted alkylene. $R^3$ is substituted or unsubstituted cycloalkyl, substituted or unsubstituted heterocycloalkyl, substituted or unsubstituted aryl or substituted or unsubstituted heteroaryl.

In embodiments of Formula (IV), the compound has the formula:

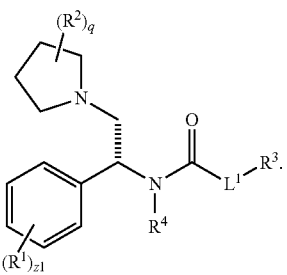
(IIIA)

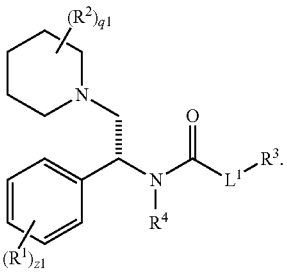
(IVA)

In embodiments of Formula (III), the compound has the formula:

In embodiments of Formula (IV), the compound has the formula:

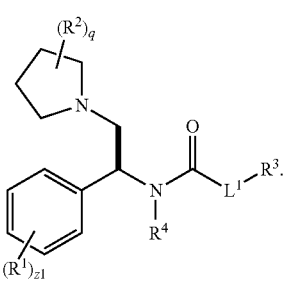
(IIIB)

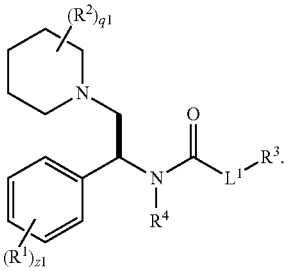
(IVB)

In another aspect, provided herein is a compound, or pharmaceutically acceptable salt thereof, having the formula:

In embodiments of Formula (IV), the compound has the formula:

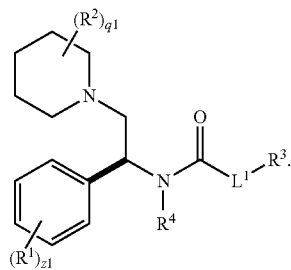

(IVC)

In embodiments of the compounds provided herein (i.e. the compounds of Formulae (I, IA, II, IIA, III, IIIA, IIIB, IV, IVA, IVB, IVC and embodiments thereof)), $R^1$ is hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^1$ may be hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, substituted or unsubstituted $C_1$-$C_{20}$ (e.g., $C_1$-$C_6$) alkyl, substituted or unsubstituted 2 to 20 membered (e.g., 2 to 6 membered) heteroalkyl, substituted or unsubstituted $C_3$-$C_8$ (e.g., $C_5$-$C_7$) cycloalkyl, substituted or unsubstituted 3 to 8 membered (e.g., 3 to 6 membered) heterocycloalkyl, substituted or unsubstituted $C_5$-$C_{10}$ (e.g., $C_5$-$C_6$) aryl, or substituted or unsubstituted 5 to 10 membered (e.g., 5 to 6 membered) heteroaryl.

In embodiments, $R^1$ is hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, $R^{1A}$-substituted or unsubstituted alkyl, $R^{1A}$-substituted or unsubstituted heteroalkyl, $R^{1A}$-substituted or unsubstituted cycloalkyl, $R^{1A}$-substituted or unsubstituted heterocycloalkyl, $R^{1A}$-substituted or unsubstituted aryl or $R^{1A}$-substituted or unsubstituted heteroaryl. In embodiments, $R^1$ is hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, or —NHC=(O)$NHNH_2$. In embodiments, $R^1$ is $R^{1A}$-substituted or unsubstituted alkyl, $R^{1A}$-substituted or unsubstituted heteroalkyl, $R^{1A}$-substituted or unsubstituted cycloalkyl, $R^{1A}$-substituted or unsubstituted heterocycloalkyl, $R^{1A}$-substituted or unsubstituted aryl or $R^{1A}$-substituted or unsubstituted heteroaryl. $R^1$ may be $R^{1A}$-substituted or unsubstituted $C_1$-$C_{20}$ (e.g., $C_1$-$C_6$) alkyl, $R^{1A}$-substituted or unsubstituted 2 to 20 membered (e.g., 2 to 6 membered) heteroalkyl, $R^{1A}$-substituted or unsubstituted $C_3$-$C_8$ (e.g., $C_5$-$C_7$) cycloalkyl, $R^{1A}$-substituted or unsubstituted 3 to 8 membered (e.g., 3 to 6 membered) heterocycloalkyl, $R^{1A}$-substituted or unsubstituted $C_5$-$C_{10}$ (e.g., $C_5$-$C_6$) aryl, or $R^{1A}$-substituted or unsubstituted 5 to 10 membered (e.g., 5 to 6 membered) heteroaryl.

$R^{1A}$ may be hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, $R^{1B}$-substituted or unsubstituted alkyl, $R^{1B}$-substituted or unsubstituted heteroalkyl, $R^{1B}$-substituted or unsubstituted cycloalkyl, $R^{1B}$-substituted or unsubstituted heterocycloalkyl, $R^{1B}$-substituted or unsubstituted aryl or $R^{1B}$-substituted or unsubstituted heteroaryl. In embodiments, $R^{1A}$ is hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, or —NHC=(O)$NHNH_2$. In embodiments, $R^{1A}$ is $R^{1B}$ substituted or unsubstituted alkyl, $R^{1B}$-substituted or unsubstituted heteroalkyl, $R^{1B}$-substituted or unsubstituted cycloalkyl, $R^{1B}$-substituted or unsubstituted heterocycloalkyl, $R^{1B}$-substituted or unsubstituted aryl or $R^{1B}$-substituted or unsubstituted heteroaryl. $R^{1A}$ may be $R^{1B}$-substituted or unsubstituted $C_1$-$C_{20}$ (e.g., $C_1$-$C_6$) alkyl, $R^{1B}$-substituted or unsubstituted 2 to 20 membered (e.g., 2 to 6 membered) heteroalkyl, $R^{1B}$-substituted or unsubstituted $C_3$-$C_8$ (e.g., $C_5$-$C_7$) cycloalkyl, $R^{1B}$-substituted or unsubstituted 3 to 8 membered (e.g., 3 to 6 membered) heterocycloalkyl, $R^{1B}$-substituted or unsubstituted $C_5$-$C_{10}$ (e.g., $C_5$-$C_6$) aryl, or $R^{1B}$-substituted or unsubstituted 5 to 10 membered (e.g., 5 to 6 membered) heteroaryl.

$R^{1B}$ may be hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, $R^{1C}$-substituted or unsubstituted alkyl, $R^{1C}$-substituted or unsubstituted heteroalkyl, $R^{1C}$-substituted or unsubstituted cycloalkyl, $R^{1C}$-substituted or unsubstituted heterocycloalkyl, $R^{1C}$-substituted or unsubstituted aryl or $R^{1C}$-substituted or unsubstituted heteroaryl. In embodiments, $R^{1B}$ is hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, or —NHC=(O)$NHNH_2$. In embodiments, $R^{1B}$ is $R^{1C}$-substituted or unsubstituted alkyl, $R^{1C}$-substituted or unsubstituted heteroalkyl, $R^{1C}$-substituted or unsubstituted cycloalkyl, $R^{1C}$-substituted or unsubstituted heterocycloalkyl, $R^{1C}$-substituted or unsubstituted aryl or $R^{1C}$-substituted or unsubstituted heteroaryl. $R^{1B}$ may be $R^{1C}$-substituted or unsubstituted $C_1$-$C_{20}$ (e.g., $C_1$-$C_6$) alkyl, $R^{1C}$-substituted or unsubstituted 2 to 20 membered (e.g., 2 to 6 membered) heteroalkyl, $R^{1C}$-substituted or unsubstituted $C_3$-$C_8$ (e.g., $C_5$-$C_7$) cycloalkyl, $R^{1C}$-substituted or unsubstituted 3 to 8 membered (e.g., 3 to 6 membered) heterocycloalkyl, $R^{1C}$-substituted or unsubstituted $C_5$-$C_{10}$ (e.g., $C_5$-$C_6$) aryl, or $R^{1C}$-substituted or unsubstituted 5 to 10 membered (e.g., 5 to 6 membered) heteroaryl.

$R^{1C}$ may be hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, $R^{1D}$-substituted or unsubstituted alkyl, $R^{1D}$-substituted or unsubstituted heteroalkyl, $R^{1D}$-substituted or unsubstituted cycloalkyl, $R^{1D}$-substituted or unsubstituted heterocycloalkyl, $R^{1D}$-substituted or unsubstituted aryl or $R^{1D}$-substituted or unsubstituted heteroaryl. In embodiments, $R^{1C}$ is hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, or —NHC=(O)$NHNH_2$. In embodiments, $R^{1C}$ is $R^{1D}$-substituted or unsubstituted alkyl, $R^{1D}$-substituted or unsubstituted heteroalkyl, $R^{1D}$-substituted or unsubstituted cycloalkyl, $R^{1D}$-substituted or unsubstituted heterocycloalkyl, $R^{1D}$-substituted or unsubstituted aryl or $R^{1D}$-substituted or unsubstituted heteroaryl. $R^{1C}$ may be $R^{1D}$-substituted or unsubstituted $C_1$-$C_{20}$ (e.g., $C_1$-$C_6$) alkyl, $R^{1D}$-substituted or unsubstituted 2 to 20 membered (e.g., 2 to 6 membered) heteroalkyl, $R^{1D}$-substituted or unsubstituted $C_3$-$C_8$ (e.g., $C_5$-$C_7$) cycloalkyl, $R^{1D}$-substituted or unsubstituted 3 to 8 membered (e.g., 3 to 6 membered) heterocycloalkyl, $R^{1D}$-substituted or unsubstituted $C_5$-$C_{10}$ (e.g., $C_5$-$C_6$) aryl, or $R^{1D}$-substituted or unsubstituted 5 to 10 membered (e.g., 5 to 6 membered) heteroaryl.

$R^{1D}$ may be hydrogen, halogen, =O, =S, —$CF_3$, —CN, —$CCl_3$, —COOH, —$CH_2$COOH, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, unsubstituted alkyl, unsubstituted heteroalkyl, unsubstituted cycloalkyl, unsubstituted heterocycloalkyl, unsubstituted aryl or unsubstituted heteroaryl. In embodiments, $R^{1D}$ is hydrogen, halogen, =O, =S, —$CF_3$, —CN, —$CCl_3$, —COOH, —$CH_2$COOH, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, or —NHC=(O)$NHNH_2$. In embodiments, $R^{1D}$ is unsubstituted alkyl, unsubstituted heteroalkyl, unsubstituted cycloalkyl, unsubstituted heterocycloalkyl, unsubstituted aryl or unsubstituted heteroaryl. $R^{1D}$ may be unsubstituted $C_1$-$C_{20}$ (e.g., $C_1$-$C_6$) alkyl, unsubstituted 2 to 20 membered (e.g., 2 to 6 membered) heteroalkyl, unsubstituted $C_3$-$C_8$ (e.g., $C_5$-$C_7$) cycloalkyl, unsubstituted 3 to 8 membered (e.g., 3 to 6 membered) heterocycloalkyl, unsubstituted $C_5$-$C_{10}$ (e.g., $C_5$-$C_6$) aryl, or unsubstituted 5 to 10 membered (e.g., 5 to 6 membered) heteroaryl.

In embodiments of the compounds provided herein (i.e. the compounds of Formulae (I, IA, II, IIA, III, IIIA, IIIB, IV, IVA, IVB, IVC and embodiments thereof)), $R^2$ is hydrogen, halogen, =O, =S, —$CF_3$, —CN, —$CCl_3$, —COOH, —$CH_2$COOH, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^2$ may be hydrogen, halogen, =O, =S, —$CF_3$, —CN, —$CCl_3$, —COOH, —$CH_2$COOH, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, substituted or unsubstituted $C_1$-$C_{20}$ (e.g., $C_1$-$C_6$) alkyl, substituted or unsubstituted 2 to 20 membered (e.g., 2 to 6 membered) heteroalkyl, substituted or unsubstituted $C_3$-$C_8$ (e.g., $C_5$-$C_7$) cycloalkyl, substituted or unsubstituted 3 to 8 membered (e.g., 3 to 6 membered) heterocycloalkyl, substituted or unsubstituted $C_5$-$C_{10}$ (e.g., $C_5$-$C_6$) aryl, or substituted or unsubstituted 5 to 10 membered (e.g., 5 to 6 membered) heteroaryl.

In embodiments, $R^2$ is hydrogen, halogen, =O, =S, —$CF_3$, —CN, —$CCl_3$, —COOH, —$CH_2$COOH, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, $R^{2A}$-substituted or unsubstituted alkyl, $R^{2A}$-substituted or unsubstituted heteroalkyl, $R^{2A}$-substituted or unsubstituted cycloalkyl, $R^{2A}$-substituted or unsubstituted heterocycloalkyl, $R^{2A}$-substituted or unsubstituted aryl or $R^{2A}$-substituted or unsubstituted heteroaryl. In embodiments, $R^2$ is hydrogen, halogen, =O, =S, —$CF_3$, —CN, —$CCl_3$, —COOH, —$CH_2$COOH, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, or —NHC=(O)$NHNH_2$. In embodiments, $R^2$ is $R^{2A}$-substituted or unsubstituted alkyl, $R^{2A}$-substituted or unsubstituted heteroalkyl, $R^{2A}$-substituted or unsubstituted cycloalkyl, $R^{2A}$-substituted or unsubstituted heterocycloalkyl, $R^{2A}$-substituted or unsubstituted aryl or $R^{2A}$-substituted or unsubstituted heteroaryl. $R^2$ may be $R^{2A}$-substituted or unsubstituted $C_1$-$C_{20}$ (e.g., $C_1$-$C_6$) alkyl, $R^{2A}$-substituted or unsubstituted 2 to 20 membered (e.g., 2 to 6 membered) heteroalkyl, $R^{2A}$-substituted or unsubstituted $C_3$-$C_8$ (e.g., $C_5$-$C_7$) cycloalkyl, $R^{2A}$-substituted or unsubstituted 3 to 8 membered (e.g., 3 to 6 membered) heterocycloalkyl, $R^{2A}$-substituted or unsubstituted $C_5$-$C_{10}$ (e.g., $C_5$-$C_6$) aryl, or $R^{2A}$-substituted or unsubstituted 5 to 10 membered (e.g., 5 to 6 membered) heteroaryl.

$R^{2A}$ may be hydrogen, halogen, =O, =S, —$CF_3$, —CN, —$CCl_3$, —COOH, —$CH_2$COOH, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, $R^{2B}$-substituted or unsubstituted alkyl, $R^{2B}$-substituted or unsubstituted heteroalkyl, $R^{2B}$-substituted or unsubstituted cycloalkyl, $R^{2B}$-substituted or unsubstituted heterocycloalkyl, $R^{2B}$-substituted or unsubstituted aryl or $R^{2B}$-substituted or unsubstituted heteroaryl. In embodiments, $R^{2A}$ is hydrogen, halogen, =O, =S, —$CF_3$, —CN, —$CCl_3$, —COOH, —$CH_2$COOH, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, or —NHC=(O)$NHNH_2$. In embodiments, $R^{2A}$ is $R^{2B}$-substituted or unsubstituted alkyl, $R^{2B}$-substituted or unsubstituted heteroalkyl, $R^{2B}$-substituted or unsubstituted cycloalkyl, $R^{2B}$-substituted or unsubstituted heterocycloalkyl, $R^{2B}$-substituted or unsubstituted aryl or $R^{2B}$-substituted or unsubstituted heteroaryl. $R^{2A}$ may be $R^{2B}$-substituted or unsubstituted $C_1$-$C_{20}$ (e.g., $C_1$-$C_6$) alkyl, $R^{2B}$-substituted or unsubstituted 2 to 20 membered (e.g., 2 to 6 membered) heteroalkyl, $R^{2B}$-substituted or unsubstituted $C_3$-$C_8$ (e.g., $C_5$-$C_7$) cycloalkyl, $R^{2B}$-substituted or unsubstituted 3 to 8 membered (e.g., 3 to 6 membered) heterocycloalkyl, $R^{2B}$-substituted or unsubstituted $C_5$-$C_{10}$ (e.g., $C_5$-$C_6$) aryl, or $R^{2B}$-substituted or unsubstituted 5 to 10 membered (e.g., 5 to 6 membered) heteroaryl.

$R^{2B}$ may be hydrogen, halogen, =O, =S, —$CF_3$, —CN, —$CCl_3$, —COOH, —$CH_2$COOH, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, $R^{2C}$-substituted or unsubstituted alkyl, $R^{2C}$-substituted or unsubstituted heteroalkyl, $R^{2C}$-substituted or unsubstituted cycloalkyl, $R^{2C}$-substituted or unsubstituted heterocycloalkyl, $R^{2C}$-substituted or unsubstituted aryl or $R^{2C}$-substituted or unsubstituted heteroaryl. In embodiments, $R^{2B}$ is hydrogen, halogen, =O, =S, —$CF_3$, —CN, —$CCl_3$, —COOH, —$CH_2$COOH, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, or —NHC=(O)$NHNH_2$. In embodiments, $R^{2B}$ is $R^{2C}$-substituted or unsubstituted alkyl, $R^{2C}$-substituted or unsubstituted heteroalkyl, $R^{2C}$-substituted or unsubstituted cycloalkyl, $R^{2C}$-substituted or unsubstituted heterocycloalkyl, $R^{2C}$-substituted or unsubstituted aryl or $R^{2C}$-substituted or unsubstituted heteroaryl. $R^{2B}$ may be $R^{2C}$-substituted or unsubstituted $C_1$-$C_{20}$ (e.g., $C_1$-$C_6$) alkyl, $R^{2C}$-substituted or unsubstituted 2 to 20 membered (e.g., 2 to 6 membered) heteroalkyl, $R^{2C}$-substituted or unsubstituted $C_3$-$C_8$ (e.g., $C_5$-$C_7$) cycloalkyl, $R^{2C}$-substituted or unsubstituted 3 to 8 membered (e.g., 3 to 6 membered) heterocycloalkyl, $R^{2C}$-substituted or unsubstituted $C_5$-$C_{10}$ (e.g., $C_5$-$C_6$) aryl, or $R^{2C}$-substituted or unsubstituted 5 to 10 membered (e.g., 5 to 6 membered) heteroaryl.

$R^{2C}$ may be hydrogen, halogen, =O, =S, —$CF_3$, —CN, —$CCl_3$, —COOH, —$CH_2$COOH, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, $R^{2D}$-substituted or unsubstituted alkyl, $R^{2D}$-substituted or unsubstituted heteroalkyl, $R^{2D}$-substituted or unsubstituted cycloalkyl, $R^{2D}$-substituted or unsubstituted heterocycloalkyl, $R^{2D}$-substituted or unsubstituted aryl or $R^{2D}$-substituted or unsubstituted heteroaryl. In embodiments, $R^{2C}$ is hydrogen, halogen, =O, =S, —CF$_3$, —CN, —CCl$_3$, —COOH, —CH$_2$COOH, —CONH$_2$, —OH, —SH, —SO$_2$Cl, —SO$_3$H, —SO$_4$H, —SO$_2$NH$_2$, —NO$_2$, —NH$_2$, —NHNH$_2$, —ONH$_2$, or —NHC=(O)NHNH$_2$. In embodiments, $R^{2C}$ is $R^{2D}$-substituted or unsubstituted alkyl, $R^{2D}$-substituted or unsubstituted heteroalkyl, $R^{2D}$-substituted or unsubstituted cycloalkyl, $R^{2D}$-substituted or unsubstituted heterocycloalkyl, $R^{2D}$-substituted or unsubstituted aryl or $R^{2D}$-substituted or unsubstituted heteroaryl. $R^{2C}$ may be $R^{2D}$-substituted or unsubstituted $C_1$-$C_{20}$ (e.g., $C_1$-$C_6$) alkyl, $R^{2D}$-substituted or unsubstituted 2 to 20 membered (e.g., 2 to 6 membered) heteroalkyl, $R^{2D}$-substituted or unsubstituted $C_3$-$C_8$ (e.g., $C_5$-$C_7$) cycloalkyl, $R^{2D}$-substituted or unsubstituted 3 to 8 membered (e.g., 3 to 6 membered) heterocycloalkyl, $R^{2D}$-substituted or unsubstituted $C_5$-$C_{10}$ (e.g., $C_5$-$C_6$) aryl, or $R^{2D}$-substituted or unsubstituted 5 to 10 membered (e.g., 5 to 6 membered) heteroaryl.

$R^{2D}$ may be hydrogen, halogen, =O, =S, —CF$_3$, —CN, —CCl$_3$, —COOH, —CH$_2$COOH, —CONH$_2$, —OH, —SH, —SO$_2$Cl, —SO$_3$H, —SO$_4$H, —SO$_2$NH$_2$, —NO$_2$, —NH$_2$, —NHNH$_2$, —ONH$_2$, —NHC=(O)NHNH$_2$, unsubstituted alkyl, unsubstituted heteroalkyl, unsubstituted cycloalkyl, unsubstituted heterocycloalkyl, unsubstituted aryl or unsubstituted heteroaryl. In embodiments, $R^{2D}$ is hydrogen, halogen, =O, =S, —CF$_3$, —CN, —CCl$_3$, —COOH, —CH$_2$COOH, —CONH$_2$, —OH, —SH, —SO$_2$Cl, —SO$_3$H, —SO$_4$H, —SO$_2$NH$_2$, —NO$_2$, —NH$_2$, —NHNH$_2$, —ONH$_2$, or —NHC=(O)NHNH$_2$. In embodiments, $R^{2D}$ is unsubstituted alkyl, unsubstituted heteroalkyl, unsubstituted cycloalkyl, unsubstituted heterocycloalkyl, unsubstituted aryl or unsubstituted heteroaryl. $R^{2D}$ may be unsubstituted $C_1$-$C_{20}$ (e.g., $C_1$-$C_6$) alkyl, unsubstituted 2 to 20 membered (e.g., 2 to 6 membered) heteroalkyl, unsubstituted $C_3$-$C_8$ (e.g., $C_5$-$C_7$) cycloalkyl, unsubstituted 3 to 8 membered (e.g., 3 to 6 membered) heterocycloalkyl, unsubstituted $C_5$-$C_{10}$ (e.g., $C_5$-$C_6$) aryl, or unsubstituted 5 to 10 membered (e.g., 5 to 6 membered) heteroaryl.

In embodiments of the compounds provided herein (i.e. the compounds of Formulae (I, IA, II, IIA, III, IIIA, IIIB, IV, IVA, IVB, IVC and embodiments thereof)), q is 1, q1 is 1, z is 1 and z1 is 1. $R^1$ and $R^2$ may be hydrogen or substituted or unsubstituted alkyl. In embodiments, $R^1$ and $R^2$ are hydrogen.

In embodiments of the compounds provided herein, $R^4$ is hydrogen or substituted or unsubstituted alkyl. For example, $R^4$ may be hydrogen or methyl. $R^3$ may be $R^{3A}$-substituted or unsubstituted cycloalkyl, $R^{3A}$-substituted or unsubstituted heterocycloalkyl, $R^{3A}$-substituted or unsubstituted aryl or $R^{3A}$-substituted or unsubstituted heteroaryl. $R^{3A}$ is $R^{3B}$-substituted or unsubstituted alkyl, $R^{3B}$-substituted or unsubstituted heteroalkyl, $R^{3B}$-substituted or unsubstituted cycloalkyl, $R^{3B}$-substituted or unsubstituted heterocycloalkyl, $R^{3B}$-substituted or unsubstituted aryl or $R^{3B}$-substituted or unsubstituted heteroaryl. $R^{3B}$ is $R^{3C}$-substituted or unsubstituted cycloalkyl, $R^{3C}$-substituted or unsubstituted heterocycloalkyl, $R^{3C}$-substituted or unsubstituted aryl or $R^{3C}$-substituted or unsubstituted heteroaryl. $R^{3C}$ is halogen, —OH, —NH$_2$, —SH, —C(O)OH, —C(O)NH$_2$, —CF$_3$, —CCl$_3$, —CN, —N$_3$, unsubstituted alkyl, unsubstituted heteroalkyl, unsubstituted cycloalkyl, unsubstituted heterocycloalkyl, unsubstituted aryl or unsubstituted heteroaryl.

In embodiments, $R^{3A}$ is $R^{3B}$-substituted or unsubstituted alkyl, $R^{3B}$-substituted or unsubstituted cycloalkyl, $R^{3B}$-substituted or unsubstituted heterocycloalkyl, $R^{3B}$-substituted or unsubstituted aryl or $R^{3B}$-substituted or unsubstituted heteroaryl. $R^{3A}$ may also be $R^{3B}$-substituted or unsubstituted cycloalkyl, $R^{3B}$-substituted or unsubstituted heterocycloalkyl, $R^{3B}$-substituted or unsubstituted aryl or $R^{3B}$-substituted or unsubstituted heteroaryl.

In embodiments of the compounds provided herein, $R^3$ is not substituted or unsubstituted aryl. For example, $R^3$ may not be substituted or unsubstituted phenyl (e.g. unsubstituted phenyl). In embodiments, $R^3$ is not substituted phenyl (e.g. a halogen substituted phenyl such as a chloro substituted phenyl).

Also provided herein are pharmaceutical formulations including a compound provided herein and a pharmaceutically acceptable excipient.

Methods

Provided herein, inter alia, are methods and compositions for treating pain in human subjects, particularly male human subjects. As set forth in detail in the Examples section below, it has been demonstrated that anti-analgesic (e.g. pain enhancing) activity of opioid receptor agonist-antagonists (e.g. κ-agonist-antagonists) is facilitated by the NOP receptor. A "κ-agonist-antagonist" as used herein includes weak mu opioid receptor agonists. Thus, the present invention provides a completely new modality in achieving analgesia.

In one aspect, a method is provided for treating pain in a subject in need thereof. The method includes administering to the subject a therapeutically effective amount of a compound provided herein. In embodiments, the subject is a male subject, such as a mammalian male subject (e.g. a human male subject).

The pain may emanate from a wide variety of sources or be derived from a wide variety of causes. Thus, the pain may be nociceptive pain (e.g., trauma, procedural, cut, sprains, bone fractures, burns, bumps, bruises), neuropathic pain (e.g., post herpetic neuralgia, reflex sympathetic dystrophy/causalgia, cancer pain, pain induced by treatment of cancer, HIV/AIDS or hepatitis, diabetes, phantom limb pain, entrapment neuropathy, chronic alcohol use, exposure to other toxins, vitamin deficiencies and idiopathic), inflammatory pain (e.g., arthritis, colitis, carditis, pulmonits, nephritis, myositis, vasculitis, endometriosis, neuritis, dermatitis and pain associated with other inflammatory conditions), chronic widespread pain (e.g., fibromyalgia, migraine, irritable bowel syndrome, syndrome X, interstitial bladder syndrome, chronic fatigue syndrome, post-traumatic stress disorder, pain associated with psychiatric illnesses such as anxiety and depression and stress-related pain conditions, and secondary to inflammatory or neuropathic pain syndromes) or mixed etiology (i.e., combinations of two or more of the above four categories).

The compounds useful in treating pain in the methods provided herein typically mediate their analgesic effect through an opioid receptor that is not a NOP receptor. The opioid receptor may be a kappa opioid receptor, a delta opioid receptor or a mu opioid receptor. Thus, in embodiments, the compound is a delta opioid receptor agonist, a kappa opioid receptor agonist or a mu opioid receptor agonist. The compound may be a kappa opioid receptor agonist. In embodiments, the compounds is a kappa opioid receptor agonist and a mu opioid receptor agonist. In embodiments, the compounds is a kappa opioid receptor agonist and a weak mu opioid receptor agonist.

As explained above and detailed in the below examples, the compound is preferably not a NOP receptor agonist since it has been discovered herein that the NOP receptor mediates anti-analgesic effects (e.g. delayed onset anti-analgesic effect). Thus, in embodiments, the compound is not a NOP receptor agonist. In embodiment, the compound is a NOP receptor antagonist. The compound may also be a low-affinity NOP receptor binder (i.e. a compound that does not measurably bind to the NOP receptor under normal in vitro experimental conditions or binds to the NOP receptor with a Kd of more than 1 µM).

A sexual dimorphism is often observed with regard to the anti-analgesic effect (e.g. delayed onset anti-analgesic effect) mediated by the NOP receptor commonly. Thus, in embodiments, the subject being treated is a male subject (e.g. a male mammal such as a male human).

In another aspect, a method of inhibiting a nociceptin (NOP) receptor is provided. The method includes contacting a NOP receptor with an effective amount of a compound provided herein thereby inhibiting the NOP receptor. The contacting may occur in vitro. The method may further include contacting the compound with an opioid receptor thereby activating the opioid receptor. The opioid receptor is typically a delta opioid receptor, a kappa opioid receptor or a mu opioid receptor.

In another aspect, a method of activating an opioid receptor is provided. The method includes contacting an opioid receptor with an effective amount of a compound provided herein thereby activating the opioid receptor. The opioid receptor is typically a delta opioid receptor, a kappa opioid receptor or a mu opioid receptor or a combination thereof. In embodiments, the opioid receptor is a kappa opioid receptor. In embodiments, the compound is not a NOP receptor agonist. The compound may alternatively be a NOP receptor antagonist. The compound may also be a low-affinity NOP receptor binder. In some embodiments, the opioid receptor is a kappa opioid receptor and a mu opioid receptor.

In another aspect, a method of determining whether a test compound elicits an analgesic effect in a human male subject and does not elicit an anti-analgesic effect (e.g. pain enhancing) in a human male subject is provided. The method includes (a) administering a test compound to a human male subject, (b) determining whether the test compound elicits an analgesic effect in the human male subject at a first time point and (c) determining whether the test compound elicits an anti-analgesic (e.g. pain enhancing) effect in the human male subject at second time point thereby determining whether a test compound elicits an analgesic effect in a human male subject and does not elicit an anti-analgesic (e.g. pain enhancing) effect in a human male subject. In some embodiments, the second time point is at least 70 minutes after the administering. In other embodiments, the second time point is at least about 90 minutes after the administering. In other embodiments, the second time point is at least about 110 minutes after the administering. In some embodiments, the method further includes prior to the administering, determining whether the test compound binds to a NOP receptor. In some embodiments, the method further includes prior to the administering, determining whether the test compound is a NOP receptor antagonist. Thus, in some embodiments, the anti-analgesic effect (e.g. pain enhancing) is a delayed anti-analgesic effect (e.g. pain enhancing).

In another aspect, a method of determining whether a test compound elicits an analgesic effect in a mammal and does not elicit an anti-analgesic (e.g. pain enhancing) effect in mammal is provided. The method includes (a) administering a test compound to a mammal, (b) determining whether the test compound elicits an analgesic effect in the mammal at a first time point and (c) determining whether the test compound elicits an anti-analgesic effect (e.g. pain enhancing) in the mammal at a second time point thereby determining whether a test compound elicits an analgesic effect in a mammal and does not elicit an anti-analgesic (e.g. pain enhancing) effect in a mammal. In some embodiments, the mammal is a non-human mammal (e.g. rodent such as a rat or mouse). In some embodiments, the second time point is at least 70 minutes after the administering. In other embodiments, the second time point is at least about 90 minutes after the administering. In other embodiments, the second time point is at least about 110 minutes after the administering. In some embodiments, the method further includes prior to the administering, determining whether the test compound binds to a NOP receptor. In some embodiments, the method further includes prior to the administering, determining whether the test compound is a NOP receptor antagonist. Thus, in some embodiments, the anti-analgesic effect (e.g. pain enhancing) is a delayed anti-analgesic effect (e.g. pain enhancing).

EXAMPLES

Clinical studies have shown that kappa-type agonist-antagonist opioid analgesics (agonist-antagonists) produce a delayed-onset anti-analgesia in men but not women, an effect blocked by co-administration of a low dose of naloxone. Applicants describe the same time-dependent anti-analgesia and its underlying mechanism in an animal model. Using the Randall-Selitto paw-withdrawal assay in male rats, Applicants found that nalbuphine, pentazocine, and butorphanol each produced analgesia during the first hour followed by anti-analgesia starting at ~90 minutes after administration in males but not females, closely mimicking its clinical effects. As observed in humans, co-administration of nalbuphine with naloxone in a dose ratio of 12.5:1 blocked anti-analgesia but not analgesia. Administration of the highly selective kappa agonist U69,593 produced analgesia without subsequent anti-analgesia, indicating that anti-analgesia is not mediated by kappa-opioid receptors. Applicants therefore tested the role of other receptors in nalbuphine anti-analgesia. Nociceptin/orphanin FQ (NOP) and sigma-1 and sigma-2 receptors were chosen on the basis of receptor binding studies. The selective NOP receptor antagonists J-113397, JTC801, and J113397, but not the sigma receptor antagonist BD 1047, blocked nalbuphine anti-analgesia. Furthermore, the NOP receptor agonist NNC 63-0532 produced anti-analgesia with the same delay in onset observed with the three agonist-antagonists, but without producing preceding analgesia and this anti-analgesia was also blocked by naloxone. These results strongly support the suggestion that clinically used agonist-antagonists act at the NOP receptor to produce anti-analgesia.

Kappa (κ)-type agonist-antagonist opioid analgesics (i.e., nalbuphine, pentazocine, and butorphanol), here referred to as agonist-antagonists, have been used clinically for decades, but are considered weak analgesics compared to µ-opioids such as morphine or oxycodone. See Hansen B (2000) in *Quick reference to veterinary medicine*, ed. Fenner, W R (Lippincott Williams & Wilkins, Philadelphia), pp. 45-57; Levine R R, Walsh C T, Schwartz-Bloom R D (2000) *Pharmacology: drug actions and reactions* (Parthenon Pub. Group, New York); Walker J S (1995) in *Handbook of pharmacokinetic/pharmacodynamic correlation*, eds. Derendorf, H, Hochhaus, G (CRC Press, Boca Raton), pp. 141-170). To better understand the variables that control the efficacy of these drugs, a series of studies in patients with post-operative pain was conducted. It was found that for all three clinical agonist-antagonists women experience greater analgesia than men (Gear R W, et al. (1996), Neurosci Lett 205:207-9; Gear R W, et al. (1996), Nat Med 2:1248-50; Gordon N C, et al. (1995), Neuroscience 69:345-9; Gear R W, et al. (1999), Pain. And, in a placebo controlled study, men receiving nalbuphine actually experienced worse pain than those receiving placebo (Gear R W, et al. (1999), *Pain* 83:339-45). Analgesia was observed in both men and women during the first hour after administration, but by ~90 minutes men reported increasing pain (i.e., anti-analgesia) (Gear R W, et al. (1999), *Pain* 83:339-45).

In subsequent studies it was found that co-administration of nalbuphine with the non-selective opioid receptor antagonist naloxone in a narrow range of dose ratios, centered around 12.5:1 (nalbuphine:naloxone), blocks anti-analgesia and produces enhanced and prolonged analgesia, similar to that observed in women (Gear R W, et al. (2000), *J Pain* 1:122-127; Gear R W, et al. (2003), *Neurosci Lett* 351:5-8).

These results indicate that in men nalbuphine acts at two distinct classes of receptors, a κ-opioid and mu-opioid "analgesia" receptor (Gutstein H B, Akil H (2001) in *Goodman & Gilman's The Pharmacological Basis of Therapeutics*, eds. Hardman, J G, Limbird, L E (McGraw-Hill, New York), pp. 569-619) and an "anti-analgesia" receptor, the identity of which remains to be determined. Pharmacodynamic modeling recently provided support for this hypothesis (Kshirsagar S, Gear R, Levine J, Verotta D (2008), *J Pharmacokinet Pharmacodyn* 35:69-83).

Investigating the mechanism of agonist-antagonist induced anti-analgesia using human subjects is significantly hampered by the lack of clinically available receptor selective pharmacological agents. Therefore, to take advantage of the broad range of receptor selective agents only available for animal studies, an animal model of agonist-antagonist anti-analgesia in male rats was developed. On the basis of receptor binding assays as well as their reported pain-enhancing properties, the roles of the nociceptin/orphanin FQ (NOP) receptor and the two sigma (σ) receptors were evaluated in the anti-analgesic effect of κ-agonist-antagonist opioid analgesics.

Materials and Methods

Animals

All experiments were performed on 250-300 g adult male and female Sprague-Dawley rats (Charles River Laboratories, Hollister, Calif., USA). Animals were housed in a controlled environment at the animal care facility of the University of California, San Francisco, under a 12 hour light/dark cycle. Food and water were available ad libitum. Experiments were approved by the Institutional Animal Care and Use Committee at UCSF and adhered to guidelines of the American Association of Laboratory Animal Care, the National Institutes of Health, and the Committee for Research and Ethical Issues of the International Association for the Study of Pain. Effort was made to minimize the number of animals used and their suffering.

Mechanical Nociceptive Threshold Testing

Nociceptive testing was performed using an Ugo Basile Analgesymeter (Stoelting, Chicago, Ill., USA), which applies a linearly increasing mechanical force on the dorsum of the hind paw. Nociceptive threshold was defined as the force in grams at which the rat withdrew its paw. Each paw was treated as an independent measure and each experiment performed on a separate group of rats.

Prior to experiments, rats were trained in the paw-withdrawal test at 5 minute intervals for 1 hour/day for 3 days. On the day of the experiment, baseline paw-withdrawal threshold was measured before intravenous (i.v.) drug administration. Post-administration thresholds were recorded 30 minutes later and thereafter at 15 minute intervals for a total of three hours. Changes in paw-withdrawal threshold are presented as percent change from baseline.

Drugs

Nalbuphine hydrochloride, an agonist-antagonist, naloxone hydrochloride, a non-selective opioid receptor antagonist, and U-69593, a selective κ-opioid receptor agonist, were obtained from Sigma-Aldrich (St. Louis, Mo.). Pentazocine lactate (Talwin 30 mg/ml) was obtained from Hospira (Lake Forest, Ill.). Butorphanol was obtained from Bedford Laboratories (Bedford, Ohio). J-113397 and JTC-801, non-peptide nociceptin/orphanin FQ (NOP, ORL1) receptor selective antagonists, BD 1047, a selective sigma (σ)-receptor antagonist ($\sigma_1 > \sigma_2$), and NNC 63-0532, a selective NOP receptor agonist, were obtained from Tocris Bioscience (Ellisville, Mo.). SB 612111, another non-peptide selective nociceptin/orphanin FQ (NOP, ORL1) receptor antagonist, was obtained from Axon Medchem BV (Groningen, The Netherlands). Nalbuphine and naloxone were dissolved in physiological saline (0.9%); pentazocine was diluted with physiological saline to 5 mg/ml; U-69593 was dissolved in 45% aq 2-hydroxypropyl-β-cyclodextrin; J-113397, SB 612111, and JTC801 were dissolved in DMSO; and BD 1047 was dissolved in water. NNC 63-0532 was dissolved in 100% ethanol and then diluted 1:1 with 0.9% saline; the concentration of this solution was adjusted so that the injection volume was 250 μl. Nalbuphine, pentazocine, butorphanol, naloxone, saline, U-69593, or NNC 63-0532 were administered intravenously (i.v.) into a lateral tail vein with a 25-gauge infusion catheter; animals were briefly anesthetized with 2.5% isoflurane to facilitate this procedure. To allow time for absorption J-113397, JTC801, SB 612111, and BD 1047 were administered subcutaneously (s.c.) in the nape of the neck without anesthesia 45 minutes prior to nalbuphine administration Uchiyama H et al. (2008), *Neurosci Lett* 431:66-70).

Receptor Binding

Binding assays for nalbuphine, pentazocine, and naloxone at $\sigma_1$, $\sigma_2$, and NOP receptors were performed by MDS Pharma Services (Bothell, Wash.).

Statistical Analysis

Group data (all groups n=6) are presented as mean±SEM; data were analyzed using one-way or two-way ANOVAs as appropriate. Significance (alpha level) was set at $p \leq 0.05$). Two-way ANOVAs demonstrating a significant interaction were further analyzed with one way ANOVAs to determine the basis of the interaction. For within subjects effects, one way repeated measures ANOVAs were performed to determine if individual groups changed significantly over time. If so, simple contrasts were employed to determine which time points differed significantly from baseline. Because simple contrasts analysis requires multiple comparisons, a Bonferroni-type correction was applied to adjust the alpha level by dividing 0.05 by the number of comparisons. Scheffé post hoc analysis was employed to determine the basis of significance for between subjects main effects involving more than two groups.

TABLE 1

| | Inhibition (%) | | |
|---|---|---|---|
| | Nalbuphine | Naloxone | Pentazocine |
| Nociceptin/orphanin F/Q (NOP) | 12 | 19 | 24 |

TABLE 1-continued

|  | Inhibition (%) | | |
| --- | --- | --- | --- |
|  | Nalbuphine | Naloxone | Pentazocine |
| Sigma1 ($\sigma_1$) | −2 | 9 | 93 |
| Sigma2 ($\sigma_2$) | 15 | −2 | 81 |

Nalbuphine, naloxone and pentazocine binding to candidate neurotransmitter receptors. Samples of nalbuphine (10 μM), naloxone (10 μM), and pentazocine (10 μM) were tested to determine their ability to inhibit binding of NOP, $\sigma_1$, and $\sigma_2$ ligand standards to their receptors. Whereas all three drugs demonstrate binding to the NOP receptor, nalbuphine does not bind to the $\sigma_1$ receptor and naloxone does not bind to the $\sigma_2$ receptor.

Results

Effect of Nalbuphine in Males

To establish an animal model of agonist-antagonist-induced anti-analgesia, separate groups of rats received nalbuphine (0.1, 0.3, or 1.0 mg/kg) or saline (vehicle). The highest dose of nalbuphine showed analgesia early in the testing period, but, beginning at ~90 minutes, nociceptive thresholds decreased below baseline, an anti-analgesic effect that persisted to the end of the three hour experiment (FIG. 1A).

A two-way ANOVA demonstrated a significant time× group interaction ($F_{30,200}$=17.829; p<0.001), indicating that the groups responded differently over time, but not a significant main effect of group ($F_{3,20}$=2.714; p=0.072). Because the time×group interaction was significant, separate one-way repeated measures ANOVAs were performed to identify the doses of nalbuphine that produced significant change over time. There was a significant effect of time for nalbuphine 0.1 mg/kg ($F_{11,55}$=4.517; p<0.030), 0.3 mg/kg ($F_{11,55}$=23.451; p<0.001), and 1 mg/kg ($F_{11,55}$=71.399; p<0.001), but not saline ($F_{11,55}$=1.350; p=0.299). Simple contrasts examining individual time points with respect to baseline within each group, however, revealed significant differences only at the two highest nalbuphine doses.

Effect of Nalbuphine in Females

Earlier clinical studies showed nalbuphine-induced anti-analgesia in men but not in women (Gear R W, et al. (1999), *Pain* 83:339-45); therefore, Applicants determined if this sexual dimorphism is also present in the rat. In female rats nalbuphine 1.0 mg/kg induced early analgesia but no anti-analgesia, consistent with Applicants' earlier finding in humans (FIG. 1B).

A two-way ANOVA demonstrated a significant time× group interaction ($F_{10,90}$=121.163; p<0.001), indicating that males and females responded differently over time; there was also a significant main effect of group ($F_{1,9}$=9.014; p<0.001). Because the time×group interaction was significant, a separate one-way repeated measures ANOVA for the female group showed a significant effect of time ($F_{11,55}$=4.517; p<0.030). Simple contrasts examining individual time points with respect to baseline revealed significant analgesia during the first four time points (p<0.002) but no anti-analgesia.

Effect of Naloxone on Nalbuphine Anti-Analgesia

Figure 2:
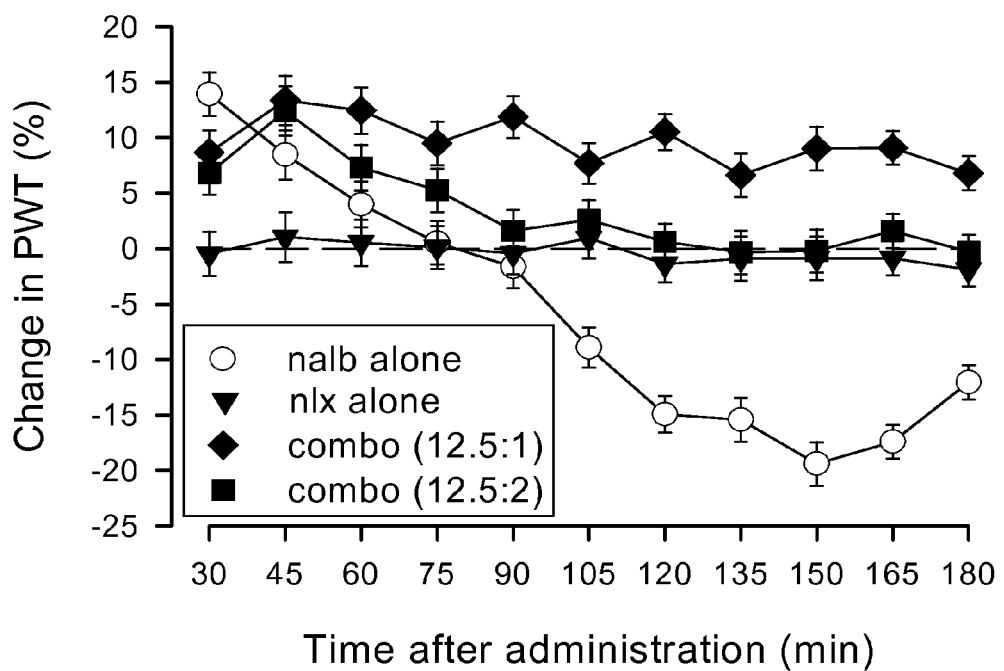
FIG. 2. Naloxone co-administered with nalbuphine. Naloxone (80 or 160 µg/kg, i.v.) co-administered with nalbuphine (1 mg/kg, i.v.) blocked anti-analgesia. At the lower dose of naloxone (combo 12.5:1) nalbuphine produced greater analgesia than when administered with the higher dose of naloxone (combo 12.5:2). Naloxone alone (nlx alone, 80 µg/kg, i.v.) did not affect nociceptive threshold. In this and subsequent figures the data for the nalbuphine (1 mg/kg) alone group (nalb alone) is replotted from FIG. 1 for comparison purposes only.

To determine if nalbuphine anti-analgesia in the rat can be blocked by naloxone, as previously observed in humans (Gear R W, et al. (2000), *J Pain* 1:122-127), nalbuphine (1 mg/kg, i.v.) was administered in combination with different doses of naloxone (80 μg/kg or 160 μg/kg, resulting in a nalbuphine:naloxone ratio=12.5:1 or 12.5:2, respectively). Naloxone (80 μg/kg) was administered alone as a control (FIG. 2). Both doses of naloxone blocked nalbuphine anti-analgesia, although only the lower dose of naloxone significantly prolonged its analgesia.

Two-way ANOVA showed a significant time×group interaction ($F_{20,150}$=2.125; p=0.032), and a significant main effect of group ($F_{2,15}$=14.585; p<0.001). Scheffé post hoc analysis showed that the analgesic effect of the 12.5:1 dose ratio was significantly greater than that of the 12.5:2 dose ratio (p=0.016). On the basis of the significant interaction term, one-way repeated measures ANOVAs were performed for each of the three groups. There was a significant main effect of time for the two groups that received both nalbuphine and naloxone ($F_{11,55}$=4.243; p=0.019 for the low dose and $F_{11,55}$=9.469; p=0.001 for the high dose naloxone group); the main effect of time for the group that received naloxone alone was not significant ($F_{11,55}$=0.682; p=0.556), indicating that naloxone itself did not have an effect on nociceptive threshold. Simple contrasts revealed the specific time points at which the responses differed from baseline (FIG. 2).

Effect of Selective κ-Opioid Receptor Agonist

Figure 3:
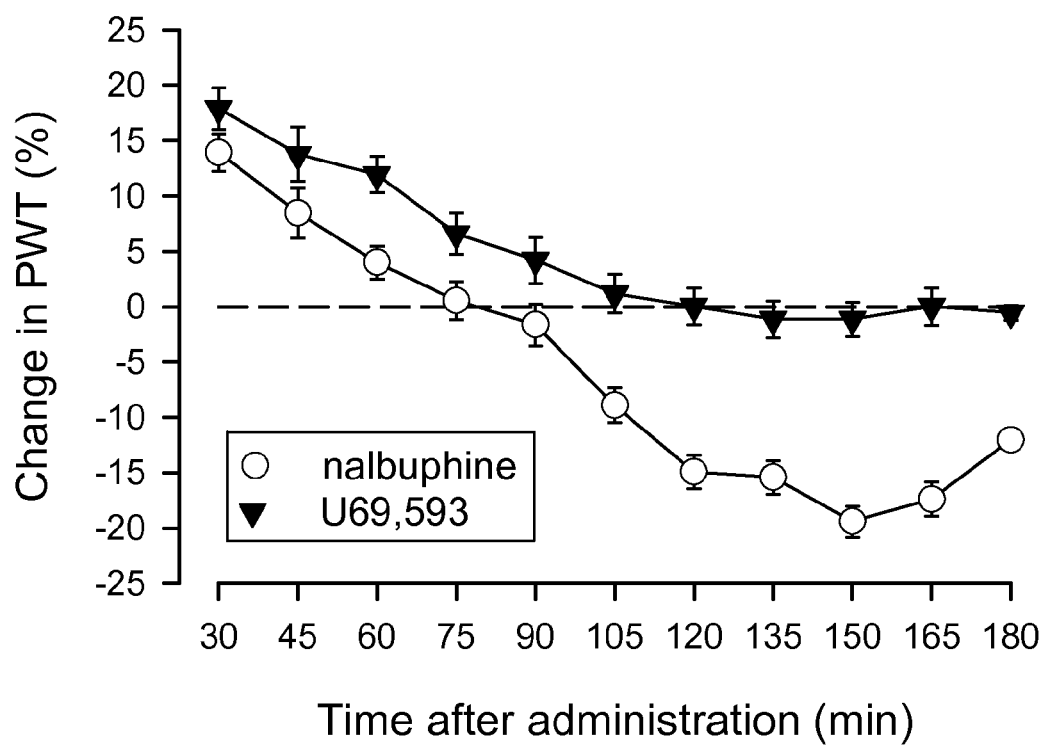
FIG. 3. U69,593. The selective κ-opioid receptor agonist U69,593 (0.3 mg/kg, i.v.) produced analgesia of similar magnitude to nalbuphine but not anti-analgesia, supporting the suggestion that nalbuphine anti-analgesia is not induced by its action at κ-receptors.

To determine if anti-analgesia is a downstream circuit effect of κ-opioid receptor activation, Applicants administered the selective κ-receptor agonist U69,593 (0.3 mg/kg, i.v., FIG. 3). U69,593 at a dose that produced similar analgesia to that of nalbuphine (1 mg/kg, i.v.), did not produce anti-analgesia, indicating that anti-analgesia is unlikely to be mediated by a circuit activated by κ-receptors, either directly or through downstream activation of an anti-analgesia circuit.

A one-way repeated measures ANOVA showed a significant effect of time ($F_{11,44}$=52.841; p<0.001). Simple contrasts demonstrated that the effect of U69,593 differed significantly from baseline during the first four time points, but not thereafter.

Receptors Involved in Nalbuphine Anti-Analgesia

Since the anti-analgesic effect of nalbuphine is not mediated by κ-opioid receptors, Applicants sought to generate a list of candidate anti-analgesia receptors by conducting receptor binding assays for both nalbuphine and naloxone. Samples of nalbuphine and naloxone were tested by a commercial laboratory for binding to the NOP and σ receptors (Table 1). The NOP receptor was chosen because its activation at some brain sites has been associated with pain enhancement (Meunier J C, et al. (1995), *Nature* 377:532-5; Mogil J S, et al. (1996), *Neuroscience* 75:333-7). Sigma receptors were chosen because they have been suggested to have anti-analgesic effects (Chien C C, Pasternak G W (1993), *Eur J Pharmacol* 250:R7-8; Chien C C, Pasternak G W (1994), *J Pharmacol Exp Ther* 271:1583-90).

Role of NOP Receptors

NOP Receptor Antagonists.

Figure 4:
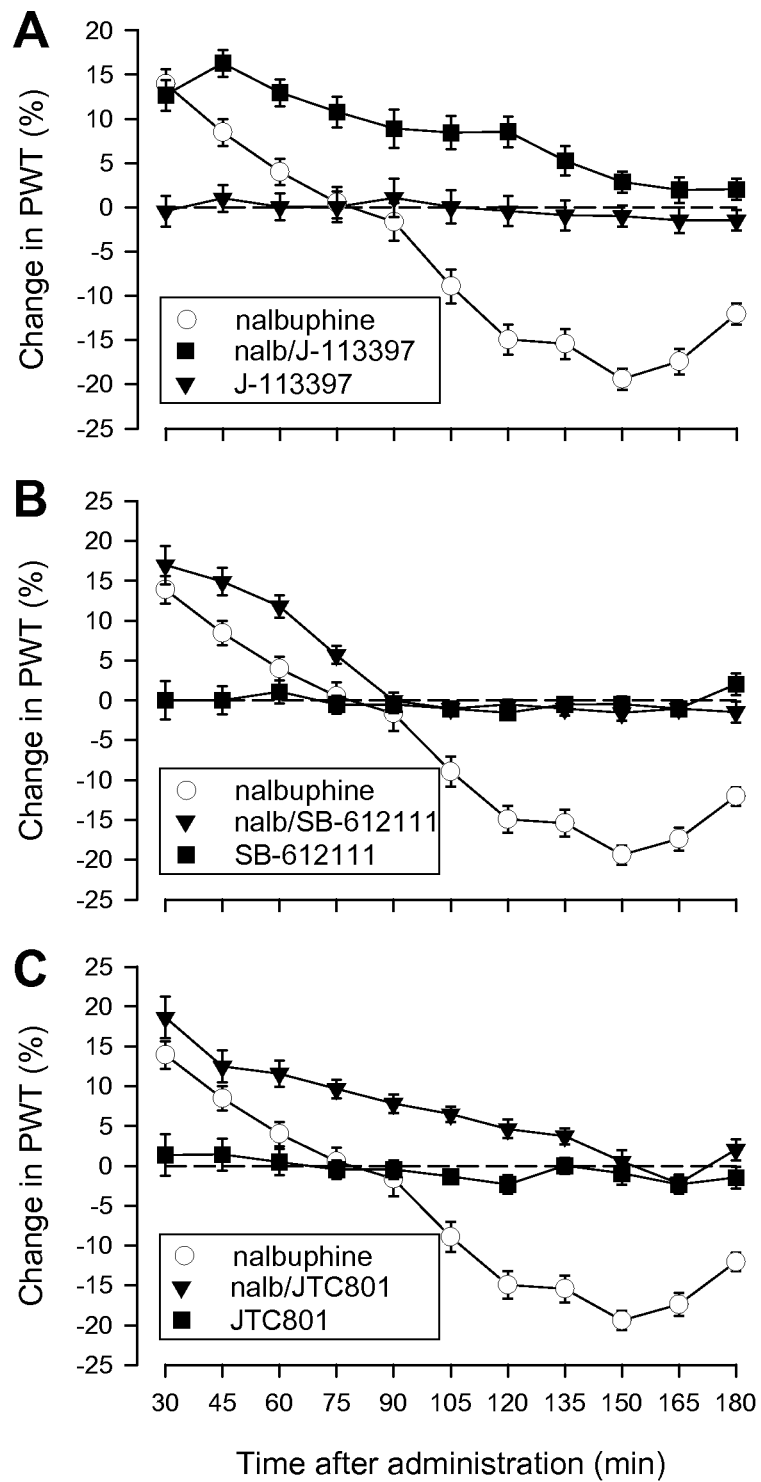
FIG. 4. NOP receptor antagonists. Selective NOP-receptor antagonists were administered in separate groups of rats 45 minutes prior to nalbuphine (nalb, 1 mg/kg, i.v.) or saline (i.v.). In the presence of the antagonist nalbuphine only produced analgesia, indicating the selective blockade of anti-analgesia. There were no significant changes in nociceptive threshold to any of the NOP receptor antagonists when they were administered with saline. A. J-113397; B. SB-612111; C. JTC801.

To test for the involvement of the NOP receptor in nalbuphine anti-analgesia, the selective NOP receptor antagonist J-113397 (30 mg/kg, s.c.) was administered subcutaneously 45 minutes prior to nalbuphine (1 mg/kg, i.v.) and compared to the effect of the same dose of J-113397 administered 45 minutes prior to i.v. saline in a separate control group of rats. J-113397 blocked anti-analgesia prolonging nalbuphine analgesia but had no effect itself (FIG. 4A), implicating the NOP receptor as a mediator of agonist-antagonist anti-analgesia. To confirm this result, two other NOP receptor selective antagonists, SB-6112111 and JTC801, were also tested. Both similarly blocked nalbuphine anti-analgesia without affecting nociception themselves (FIGS. 4B, 4C).

For J-113397 the two-way ANOVA showed a significant time×group interaction ($F_{10,100}=9.859$; $p<0.001$) and a significant main effect of group ($F_{1,10}=25.471$; $p<0.001$). Based on the significant time×group interaction, one-way repeated measures ANOVAs were performed separately for each of the groups. For the group receiving the combination of J-113397 and nalbuphine there was a significant main effect of time ($F_{11,55}=21.125$; $p<0.001$); simple contrasts revealed significant analgesia during the first four time points but no anti-analgesia at later time points. The main effect of time for the group receiving the combination of J-113397 and saline was not significant ($F_{11,55}=1.286$; $p=0.314$).

For SB-612111 the two-way ANOVA showed a significant time×group interaction ($F_{10,100}=20.352$; $p<0.001$) and a significant main effect of group ($F_{1,10}=41.381$; $p<0.001$). Based on the significant time×group interaction, one-way repeated measures ANOVAs were performed separately for each of the groups. For the group receiving the combination of SB-612111 and nalbuphine there was a significant main effect of time ($F_{11,55}=30.995$; $p<0.001$); simple contrasts revealed significant analgesia during the first four time points but no anti-analgesia at later time points. The main effect of time for the group receiving the combination of SB-612111 and saline was not significant ($F_{11,55}=0.866$; $p=0.482$).

For JTC801 the two-way ANOVA showed a significant time×group interaction ($F_{10,100}=14.057$; $p<0.001$) and a significant main effect of group ($F_{1,10}=30.603$; $p<0.001$). Based on the significant time×group interaction, one-way repeated measures ANOVAs were performed separately for each of the groups. For the group receiving the combination of JTC801 and nalbuphine there was a significant main effect of time ($F_{11,55}=29.564$; $p=0.031$); simple contrasts revealed significant analgesia during the first seven time points but no anti-analgesia at later time points. The main effect of time for the group receiving the combination of JTC801 and saline was also significant ($F_{11,55}=3.377$; $p=0.031$), but simple contrasts failed to reveal any individual time points that were significantly different from baseline.

NOP Receptor Agonist.

Figure 5:
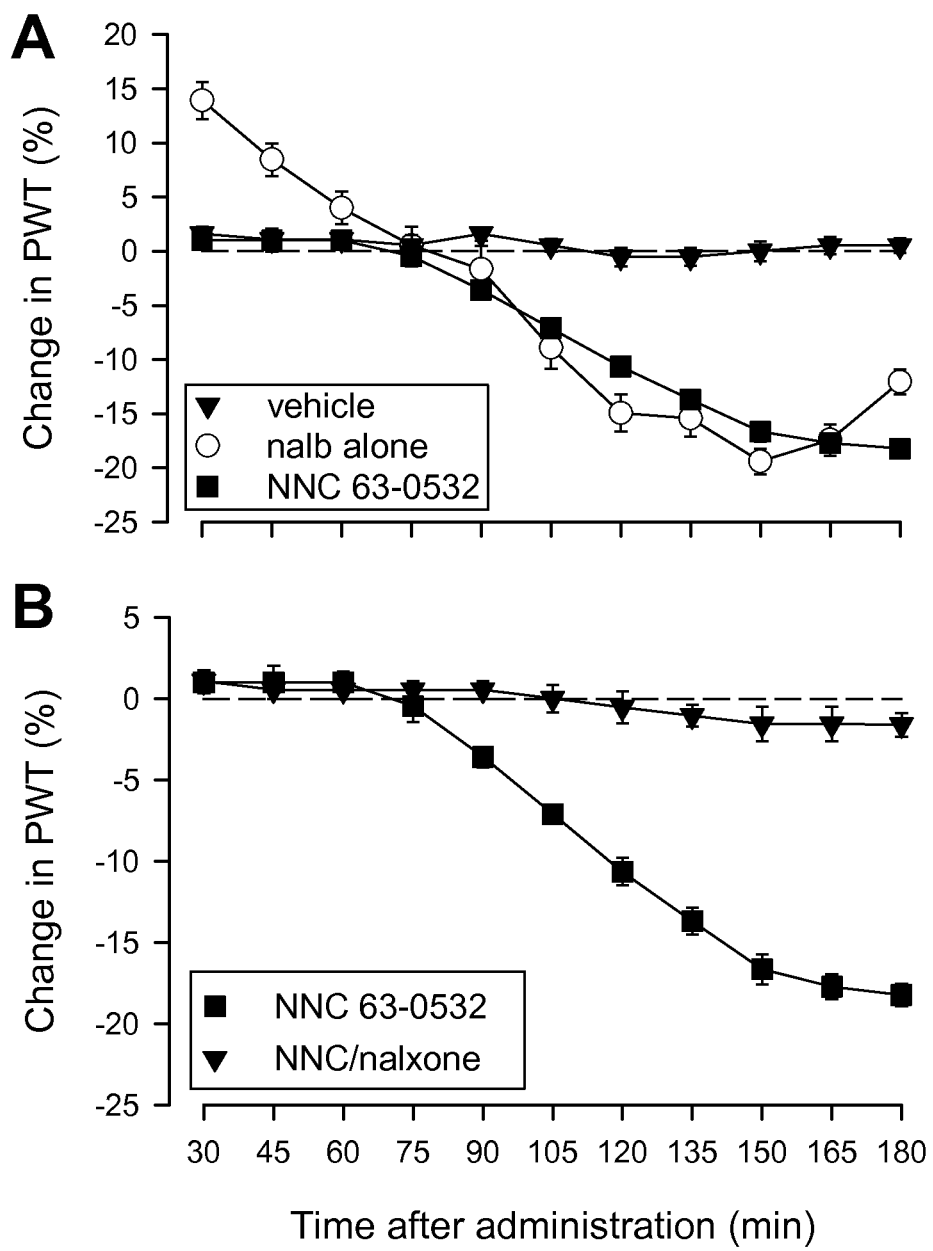
FIG. 5. NNC 63-0532. A. The selective NOP-receptor agonist NNC 63-0532 (0.3 mg/kg i.v.) produced no analgesia, but mimicked the anti-analgesic effect of nalbuphine (nalb) starting at 90 minutes and persisting through the remainder of the experiment. Administration of its vehicle did not have a significant effect. B. Co-administration of naloxone blocked NNC 63-0532-induced anti-analgesia.

To determine if selective NOP receptor activation is sufficient to produce anti-analgesia, the NOP receptor agonist NNC 63-0532 (0.3 mg/kg, i.v.) or vehicle (i.v.) as a control were administered. NNC 63-0532 produced no analgesia at any time but did produce responses significantly below baseline (i.e., demonstrating anti-analgesia) starting at ~90 minutes, similar to the anti-analgesic effects of nalbuphine (FIG. 5A).

Two-way ANOVA showed a significant group×time interaction ($F_{10,100}=47.058$; $p<0.001$) and a significant main effect of group ($F_{1,10}=405.590$; $p<0.001$). Because the time× group interaction was significant, separate one-way repeated measures ANOVAs were performed. The group receiving NNC 63-0532 showed a significant main effect of time ($F_{11,55}=132.563$; $p<0.001$); the main effect of time for the group receiving vehicle was not significant ($F_{11,55}=0.813$; $p=0.520$), indicating lack of change in nociceptive threshold over time. Simple contrasts for the NNC 63-0532 group showed that all time points starting with 90 minutes were significantly below baseline.

Effect of Naloxone on NNC 63-0532-Induced Anti-Analgesia.

Since naloxone blocks NOP-receptor-mediated anti-analgesia induced by nalbuphine, Applicants tested the hypothesis that naloxone would also block NNC 63-0532-induced anti-analgesia. NNC 63-0532 (0.3 mg/kg, i.v.) was administered with or without naloxone (80 µg/kg, i.v.). The group receiving NNC 63-0532 in combination with naloxone failed to show either analgesia or delayed onset anti-analgesia (FIG. 5B).

Two-way repeated measures ANOVA showed a significant group×time interaction ($F_{10,100}=46.830$; $p<0.001$) and a significant main effect of group ($F_{1,10}=257.473$; $p<0.001$). A one-way repeated measures ANOVA for the group receiving NNC 63-0532 in combination with naloxone showed that the main effect of time was not significant ($F_{11,55}=1.952$; $p=0.145$), indicating lack of change in nociceptive threshold over time.

Role of σ-Receptors in Anti-Analgesia

Figure 6:
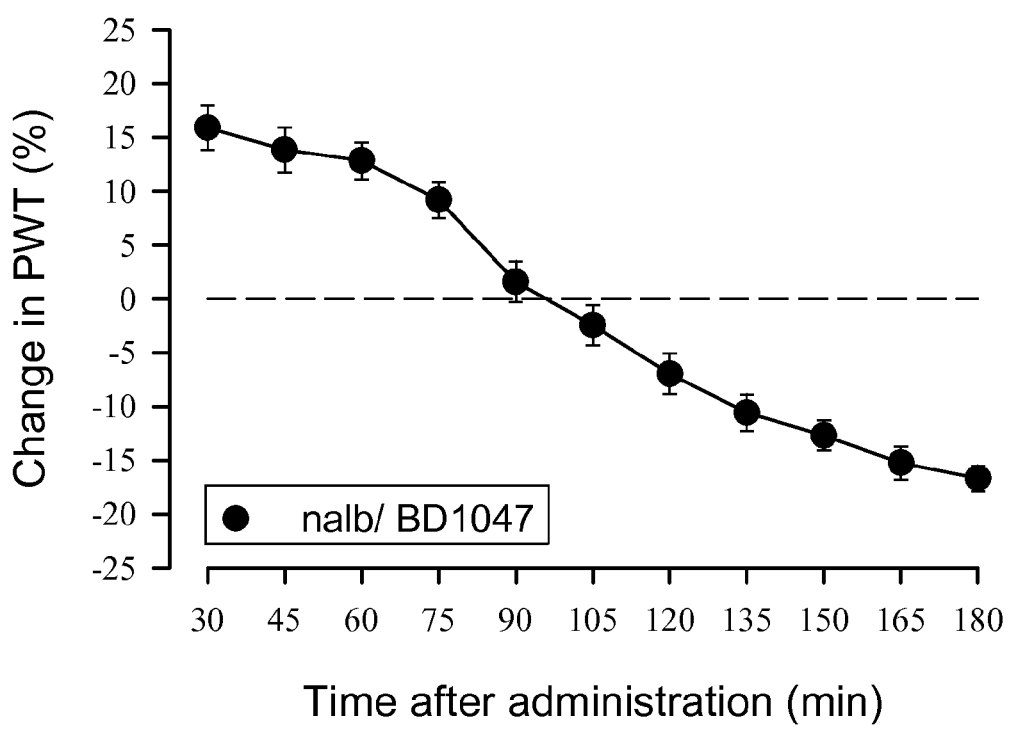
FIG. 6. BD 1047. The selective σ-receptor antagonist BD 1047 (10 mg/kg, s.c.) was administered 45 minutes prior to nalbuphine (nalb 1 mg/kg, i.v.). Similar to the effect of nalbuphine alone, both analgesia and anti-analgesia were observed. The first four time points demonstrated significant analgesia; the last four time points demonstrated significant anti-analgesia. These results indicate that BD 1047 attenuated neither the analgesic nor the anti-analgesic effects of nalbuphine.

To test the involvement of σ-receptors in nalbuphine anti-analgesia, the σ-receptor antagonist BD 1047 was administered (10 mg/kg, s.c.) 45 minutes prior (Rawls S M et al., *Pharmacol Biochem Behav* 73:779-86; Martin-Fardon R et al. (2007), *Neuropsychopharmacology* 32:1967-73) to nalbuphine (1 mg/kg, i.v.). One-way repeated measures ANOVA for this group showed a significant main effect of time ($F_{1,55}=76.330$; $p<0.001$). Simple contrasts revealed that both the early and late effects were significantly different from baseline, with the early time points showing analgesia and the later time points showing anti-analgesia (FIG. 6), indicating that BD 1047 did not significantly alter either the analgesic or the anti-analgesic effect of nalbuphine, thereby arguing against a role for σ-receptors in agonist-antagonist-induced anti-analgesia.

Effect of Pentazocine and Butorphanol in the Rat

Figure 7:
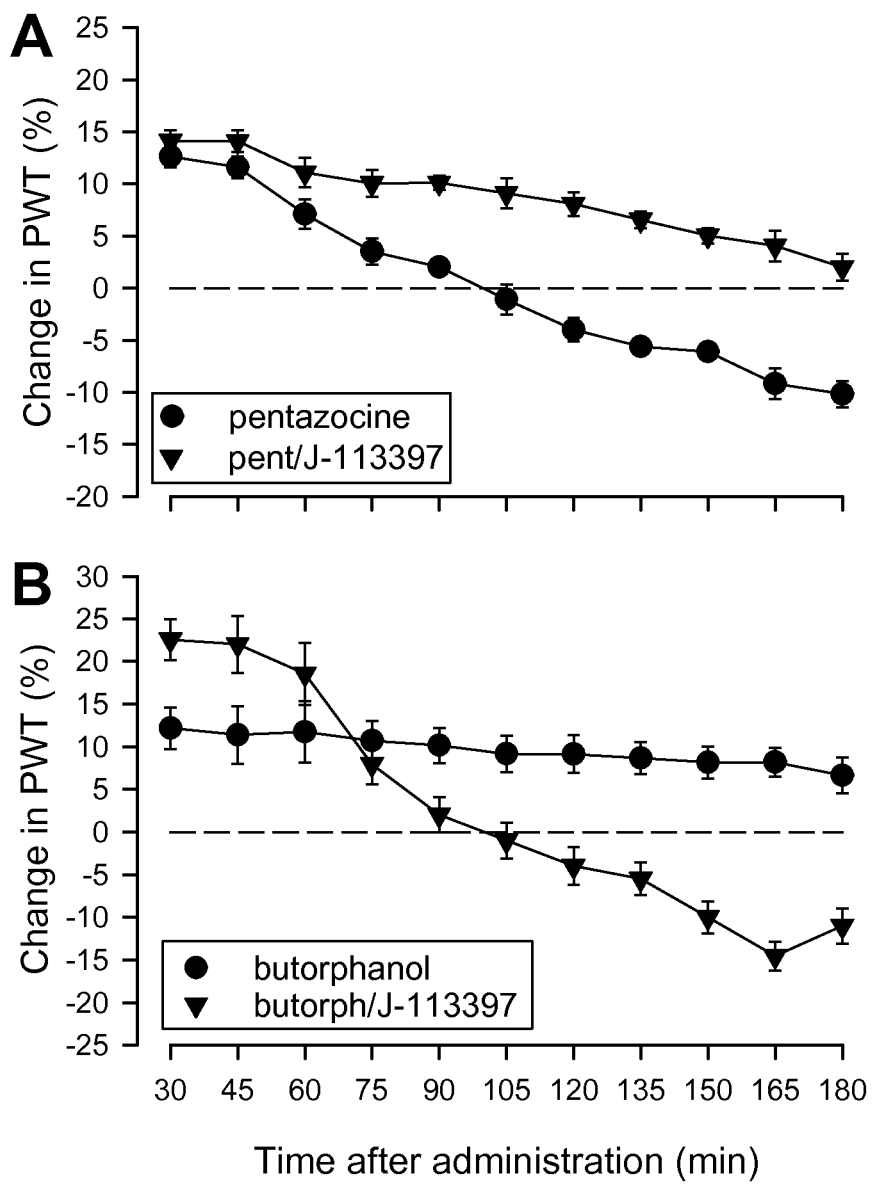
FIG. 7. Pentazocine or butorphanol co-administered with J-113397. Pentazocine (pent, 5 mg/kg, i.v.), panel A., and butorphanol (0.2 mg/kg, i.v.), panel B., both induced analgesia and delayed onset anti-analgesia. In the presence of J-113397 (30 mg/kg, s.c.) administered 45 minutes prior, these kappa-agonist-antagonists produced only analgesia, indicating that J-113397 effectively blocked anti-analgesia, similar to its effect when administered with nalbuphine.

To determine if NOP-receptor-mediated anti-analgesia induced by nalbuphine is a common characteristic among κ-agonist-antagonists, the other drugs in this class, pentazocine and butorphanol, were tested in separate groups of rats. All groups received either the NOP receptor antagonist J-113397 (30 mg/kg, s.c.) or vehicle administered 45 minutes prior to testing. Both pentazocine (FIG. 7A) and butorphanol (FIG. 7B) produced early analgesia followed by anti-analgesia at the later time points. As with nalbuphine and NNC 63-0532, the crossover between analgesia and anti-analgesia occurred at about 90 minutes. Also consistent with the effect of nalbuphine, J-113397 blocked the anti-analgesic effect of both pentazocine and butorphanol. These results are consistent with the receptor binding data (Table 1) showing that, like nalbuphine and naloxone, pentazocine binds to NOP receptors, and support the suggestion that κ-agonist-antagonists as a class produce anti-analgesia by acting at the NOP receptor.

Pentazocine.

Two-way ANOVA showed a significant time×group interaction ($F_{10,100}=10.206$; $p<0.001$) and a significant main effect of group ($F_{1,10}=68.471$; $p<0.001$). Based on the significant time×group interaction, one-way repeated measures ANOVAs were performed separately for each group. For the group receiving pentazocine alone there was a significant main effect of time ($F_{11,55}=68.287$; $p<0.001$); simple contrasts revealed significant analgesia during the first 4 time points and significant anti-analgesia during the last 4 time points. The main effect of time for the group receiving the combination of J-113397 and pentazocine was also significant ($F_{11,55}=23.325$; $p<0.001$); simple contrasts revealed analgesia during the first 8 time points but no anti-analgesia at later time points.

Butorphanol.

Two-way ANOVA showed a significant time×group interaction ($F_{10,100}=23.841$; $p<0.001$) but not a significant main effect of group ($F_{1,10}=3.808$; $p=0.080$). Based on the significant time×group interaction, one-way repeated measures ANOVAs were performed separately for each group. For the group receiving butorphanol alone there was a significant main effect of time ($F_{11,55}$=52.386; p<0.001); simple contrasts revealed significant analgesia during the first 3 time points and significant anti-analgesia during the last 3 time points. The main effect of time for the group receiving the combination of J-113397 and butorphanol was also significant ($F_{11,55}$=10.115; p=0.002); simple contrasts revealed analgesia during the first time point but no anti-analgesia at any time point.

Applicants found that the effects of κ-agonist-antagonists in rats closely replicate their effects in patients with post-operative pain (Gear R W, et al. (1999), *Pain* 83:339-45) and that the sexual dimorphism observed in humans is not species specific. In females only analgesia was observed, but agonist-antagonists produced early analgesia followed by marked anti-analgesia in males. Of note, the time at which analgesia transitioned to anti-analgesia, ~90 minutes after agonist-antagonist administration, was remarkably similar in both species. Furthermore, nalbuphine co-administered with naloxone at the same fixed dose ratio that was maximally effective in patients (12.5:1) blocked anti-analgesia without affecting analgesia, whereas a slightly higher dose of naloxone (dose ratio: 12.5:2) also reversed analgesia, again closely replicating Applicants' findings in patients with postoperative pain (Gear R W, et al. (2000), *J Pain* 1:122-127). It was proposed that the receptor at which an agonist-antagonist acts to produce analgesia (Gutstein H B, Akil H (2001) in *Goodman & Gilman's The Pharmacological Basis of Therapeutics*, eds. Hardman, J G, Limbird, L E (McGraw-Hill, New York), pp. 569-619 is different from the receptor at which it acts to produce anti-analgesia (Gear R W, et al. (2000), *J Pain* 1:122-127; Gear R W, et al. (2003), *Neurosci Lett* 351:5-8; Kshirsagar S, Gear R, Levine J, Verotta D (2008), *J Pharmacokinet Pharmacodyn* 35:69-83). This is further supported by the observation that the selective κ-receptor agonist U69,593 only induces analgesia.

Based on the finding that naloxone binds to the NOP receptor, which has been implicated as pronociceptive (Suaudeau C et al., (1998), *Fundam Clin Pharmacol* 12:420-5), NOP receptor involvement in nalbuphine anti-analgesia was tested. The NOP receptor antagonist J-113397 blocked nalbuphine's anti-analgesic effect, but not its analgesic effect. The same result was observed with the other κ-agonist-antagonists, pentazocine and butorphanol. To confirm that NOP receptor activation is sufficient to produce delayed-onset anti-analgesia, two other selective NOP receptor antagonists, SB-61211 and JTC801, were tested with nalbuphine; both blocked nalbuphine-induced anti-analgesia. Finally, the NOP receptor agonist NNC 63-0532 was administered. Although NOP receptor agonists have been shown to produce both analgesia and hyperalgesia, depending on site of injection in the central nervous system (Suaudeau C et al., (1998), *Fundam Clin Pharmacol* 12:420-5; Tian J H, et al. (1997), *Br J Pharmacol* 120:676-80; Erb K, et al. (1997), *Neuroreport* 8:1967-70; Rizzi A, et al. (2006), *Pain* 124:100-8), Applicants observed no analgesic effect of NNC 63-0532 when given systemically; rather, NNC 63-0532 mimicked nalbuphine, pentazocine, and butorphanol anti-analgesia, including a similarly delayed onset; furthermore, naloxone similarly blocked NNC 63-0532-mediated anti-analgesia. Taken together, these results strongly implicate NOP receptor activation as the basis for the anti-analgesic effects of agonist-antagonists.

The σ-receptor antagonist BD 1047 was co-administered to examine the involvement of the σ receptor, to which nalbuphine binds, in nalbuphine anti-analgesia. In a previous clinical study the involvement of the $σ_1$-receptor in anti-analgesia by administering the neuroleptic haloperidol, a known $σ_1$-receptor antagonist (Gear R W, et al. (2006), *J Pain* 7:187-91) (BD 1047 is not approved for use in humans) was investigated. Because haloperidol also binds to multiple other neurotransmitter receptors, as a control chlorpromazine was administered, which binds to many of the same receptors, but not the $σ_1$-receptor. Both haloperidol and chlorpromazine enhanced the analgesic effect of nalbuphine. Provided herein BD 1047, a σ receptor-selective ($σ_1>σ_2$) antagonist (Matsumoto R R, et al. (1995), *Eur J Pharmacol* 280:301-10) was administered. BD 1047 did not significantly alter the magnitude of the analgesic or anti-analgesic effect of nalbuphine. Of note, while nalbuphine, pentazocine and naloxone had similar affinity for the NOP receptor, their binding to the σ-receptors differed markedly (see Table 1), further ruling out a role for σ-receptors in the naloxone sensitive anti-analgesia induced by nalbuphine and pentazocine.

The analgesic effects of κ-opioids, including agonist-antagonists have been previously examined in humans (Fillingim R B, et al. (2004), *Anesthesiology* 100:1263-70; Mogil J S, et al. (2003), *Proc Natl Acad Sci USA* 100:4867-72), in primates (Negus S S, Mello N K (1999), *J Pharmacol Exp Ther* 290:1132-40), and in rodents (Cook C D et al. (2000, *Psychopharmacology* (Berl) 150:430-42; Craft R M, Bernal S A (2001), *Drug Alcohol Depend* 63:215-28; Bartok R E, Craft R M (1997), *J Pharmacol Exp Ther* 282:769-78; Khasar S G, Gear R W, Levine J D (2003), *Neurosci Lett* 345:165-8), but none were able to detect the anti-analgesic effect of κ-agonist-antagonists or other κ-opioids. Importantly, the current study sheds light on these apparent discrepancies. First, highly selective κ-receptor agonists such as U69,593, or U50,488, which were tested in some of these studies, would not be expected to induce NOP-receptor mediated anti-analgesia. Second, agonist-antagonist anti-analgesia is a delayed effect. Applicants' clinical studies (Gear R W, et al. (1996), *Nat Med* 2:1248-50; Gear R W, et al. (1999), *Pain* 83:339-45), pharmacodynamic modeling (Kshirsagar S, Gear R, Levine J, Verotta D (2008), *J Pharmacokinet Pharmacodyn* 35:69-83), and the data provided herein in the rat show that the onset of anti-analgesia is more than an hour after administration of the agonist-antagonist; none of the previous studies testing the effects of agonist-antagonists used an experimental protocol that would be expected to reveal late onset anti-analgesia. While Applicants' study reveals NOP as the receptor at which κ-agonist-antagonists act to produce anti-analgesia, the basis of the long delay (>1 hour) in onset of the anti-analgesia (by either nalbuphine, pentazocine, butorphanol, or the selective NOP-receptor agonist NNC 63-0532) remains to be determined. It is, however, unlikely to be a pharmacokinetic effect of κ-agonist-antagonists, since nalbuphine and pentazocine analgesia have a short latency to onset, and NNC 63-0532 shows the same latency to onset of anti-analgesia as the κ-agonist-antagonists, without producing prior analgesia.

In conclusion Applicants have shown that the κ-type agonist-antagonist class of opioids produces analgesic and anti-analgesic effects in rats similar to those observed in humans, supporting the rat as a model for the study of this class of opioids. Moreover, Applicants found that anti-analgesia can be demonstrated in the rat and that this effect does not result from action at the κ-opioid receptor, but rather is NOP receptor-mediated. These findings help to explain previous conflicting results in which studies in animal and human experimental pain models were unable to detect these differences and should facilitate novel strategies for development of more effective members of this class of analgesic drugs.

Sex Differences in κ-Agonist-Antagonist Analgesia.

All three clinically available κ-agonist-antagonists were tested: pentazocine, nalbuphine, and butorphanol. All showed significantly great analgesia in women than in men. (See FIG. 8: Sex differences in pentazocine analgesia).

Figure 8:
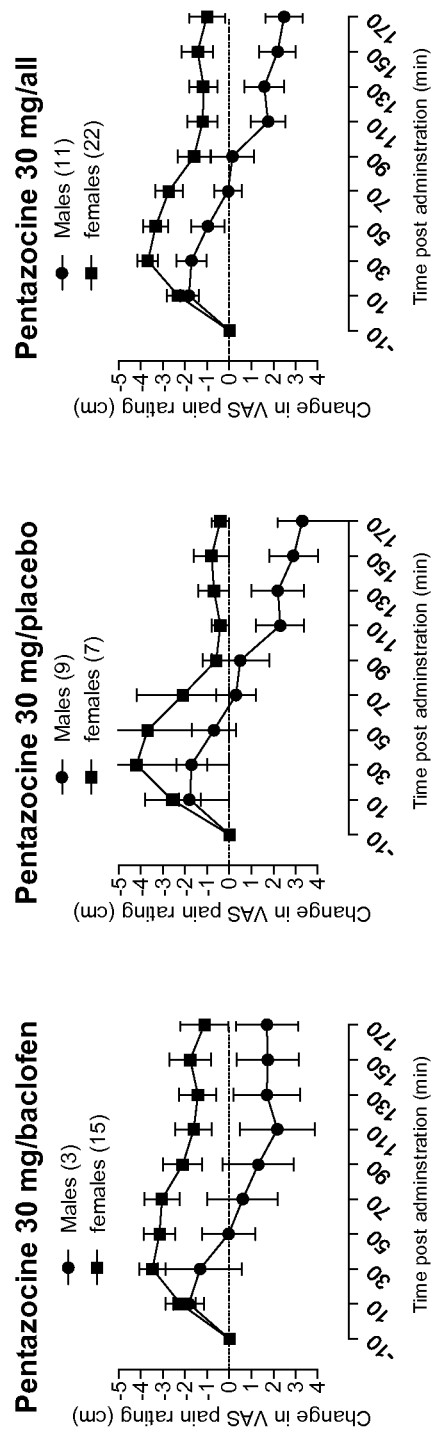
FIG. 8. Sex differences in pentazocine analgesia.

Data in FIG. 8 (Gordon N C et al., *Neuroscience*, 69:345-349, 1995) were accumulated before Applicants had discovered that κ-agonists-antagonists produce sexually dimorphic analgesia. The experiment consisted of oral administration of either baclofen (GABA$_B$ agonist) or placebo starting three days prior to the surgery. On the day of the surgery all participants received pentazocine 30 mg i.v. The object of the study was to determine if baclofen enhances the analgesic effect of pentazocine. The effect of baclofen was not significantly different from that of placebo (see left and middle graphs). However, there was a significant difference in analgesia experience by females and males. Therefore, the data for placebo and baclofen were combined and plotted in the right graph.

Figure 9:
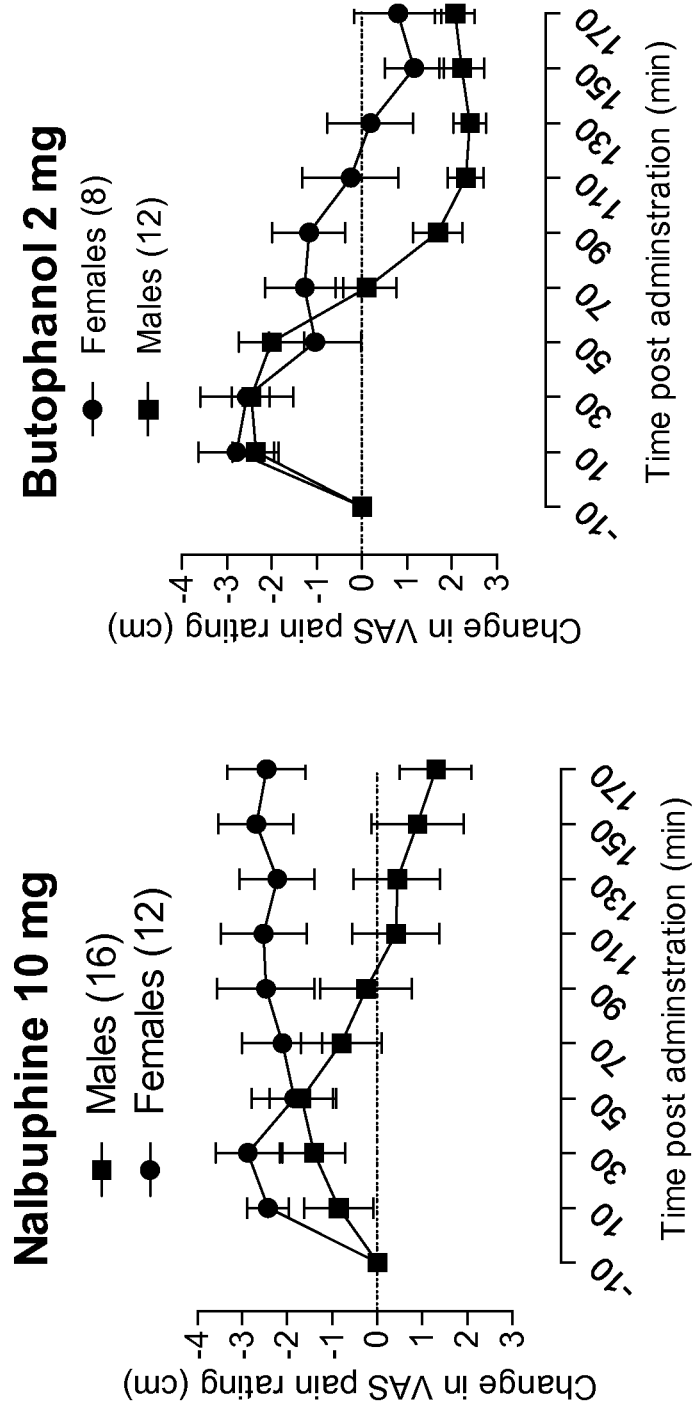
FIG. 9. Sex differences in nalbuphine and butorphanol analgesia.

To determine if sexual dimorphism is a general characteristic of κ-agonist-antagonists Applicants tested groups of males and females using either nalbuphine or butorphanol (Gear R W et al., *Nat Med*, 2:1248-1250, 1996), the other two clinically available drugs in this class. Both showed the same effects as pentazocine. Nalbuphine and butorphanol each produced significantly greater analgesia in females than in males. (See FIG. 9: Sex differences in nalbuphine and butorphanol analgesia). An important observation was the timing of the onset of increased pain in males. In all three κ-agonist-antagonists a brief period of early analgesia was followed by greater pain ("anti-analgesia") starting 70 to 90 minutes after administration.

Figure 10:
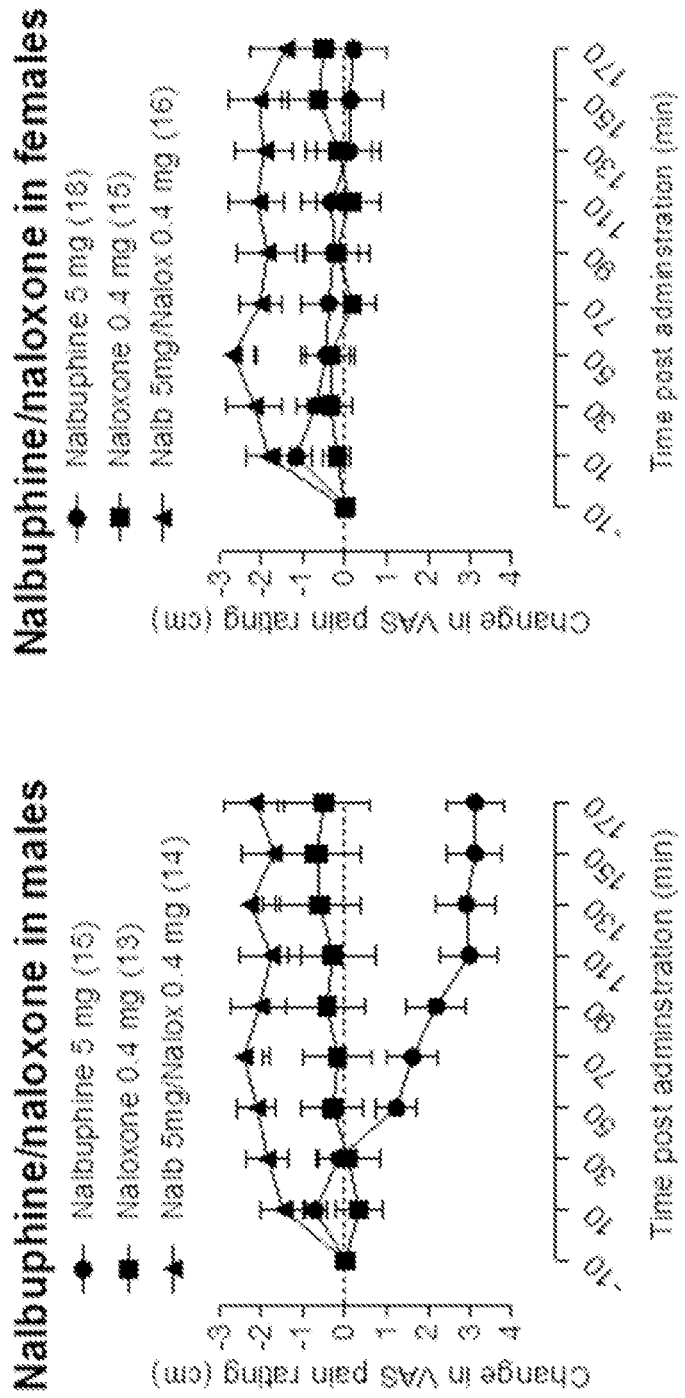
FIG. 10. Reversal of anti-analgesia by the opioid antagonist naloxone

In an earlier study conducted in animals (the rat), Applicants showed that pentazocine antinociception (Levine J D et al., *J Clin Invest*, 82:1574-1577, 1988) can be enhanced by combining it with the opioid antagonist naloxone. To test if this is also the case in humans Applicants administered naloxone (0.4 mg) in combination with nalbuphine. Subjects were stratified by sex (See FIG. 10: Reversal of anti-analgesia by the opioid antagonist naloxone). It was found that naloxone abolished the anti-analgesic effect of nalbuphine in males resulting in significant analgesia (FIG. 10 left panel). Naloxone also enhanced nalbuphine analgesia in females (FIG. 10 right panel).

Figure 11:
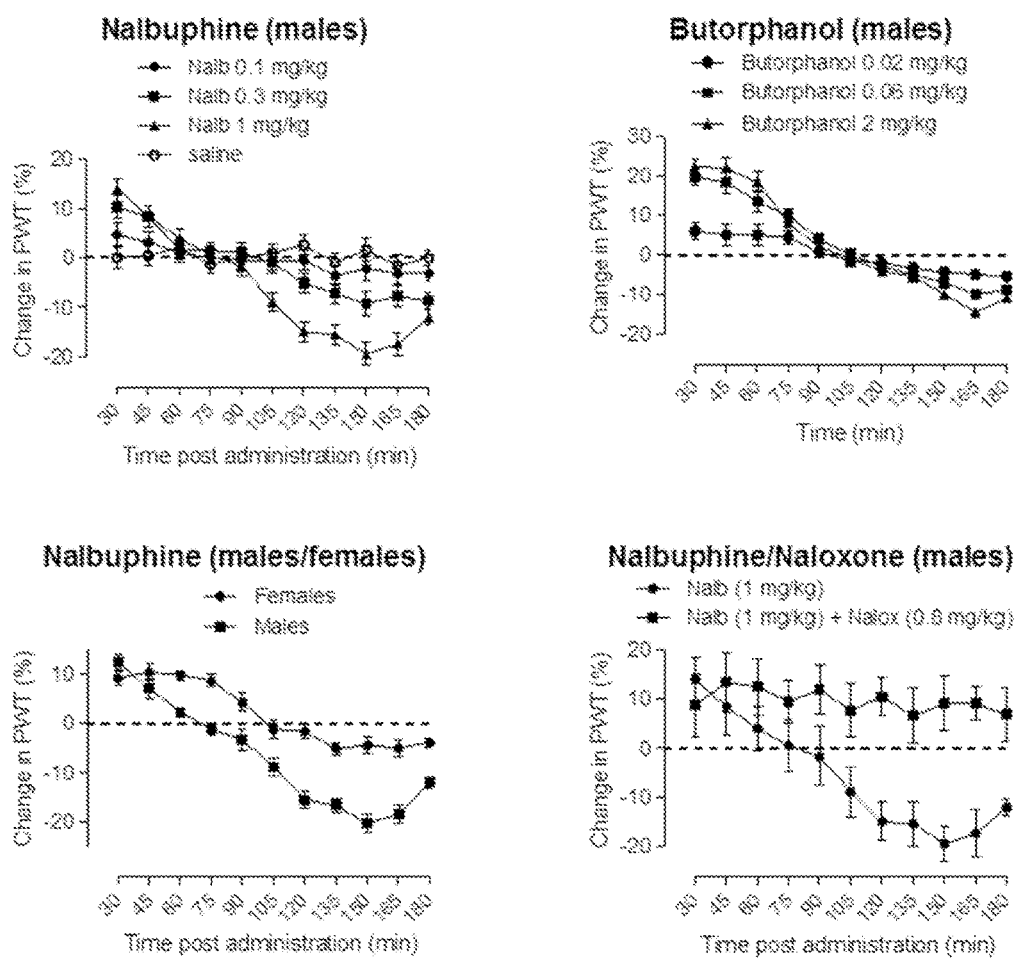
FIG. 11. An animal model that replicates the findings in humans; increasing doses of nalbuphine.

Experiments were performed, using the rat as a test subject, to determine if the κ-agonists-antagonists induce sexually dimorphic antinociception that is sensitive to naloxone as previously observed in humans. (See FIG. 11: An animal model that replicates the findings in humans). Increasing doses of nalbuphine (FIG. 11 upper left panel) or butorphanol (Figure upper right panel) induced dose-dependent anti-analgesia. Administration of the same dose of nalbuphine to male and female rats showed a significantly greater antinociceptive effect in females than in males (FIG. 11 lower left panel), and naloxone co-administration (same dose ratio as in humans) with nalbuphine (FIG. 11 lower right panel) abolished anti-analgesia inducing only antinociception (Note "PWT" is paw withdrawal threshold). Taken together, these findings strongly support the suggestion that the effects of κ-agonist-antagonists observed in humans can also be observed in the rat.

The Two-Receptor Hypothesis

The analgesic effect of kappa-agonist-antagonists is likely to be mediated by their action at a κ-opioid receptor. As implied by the name "agonist-antagonists," all three clinically available drugs in this class (i.e., nalbuphine, Zhu J et al., *J Pharmacol Exp Ther*, 282:676-684, 1997) pentazocine, (Zhu J et al., *J Pharmacol Exp Ther*, 282:676-684, 1997) and butorphanol (Commiskey S et al., *J Pharmacol Sci*, 98:109-116, 2005; Leander J D, J Pharmacol Exp Ther, 224:89-94, 1983)) are agonists at κ-receptors. And κ-receptor activation results in analgesia (Errick J K and Heel R C: Nalbuphine, *Drugs*, 26:191-211, 1983; Gutstein H B and Akil H: Opioid analgesics. In: J G Hardman and L E Limbird (Eds.), *Goodman & Gilman's The Pharmacological Basis of Therapeutics*, New York, McGraw-Hill, 2001, pp. 569-619). This class of opioids has also been reported to act as weak agonists at μ-opioid receptors, which could also contribute to μ-opioid-induced analgesia. However, naloxone (0.4 mg) produces opposite effects when co-administered with κ-opioids or morphine, which acts predominantly as a μ-receptor agonist (i.e. enhanced analgesia with κ-opioids and diminished analgesia with morphine (Levine J D and Gordon N C, *Pain*, 33:369-372, 1988)). Therefore, the role of μ-receptors in κ-opioid analgesia is probably minor at most.

Figure 12:
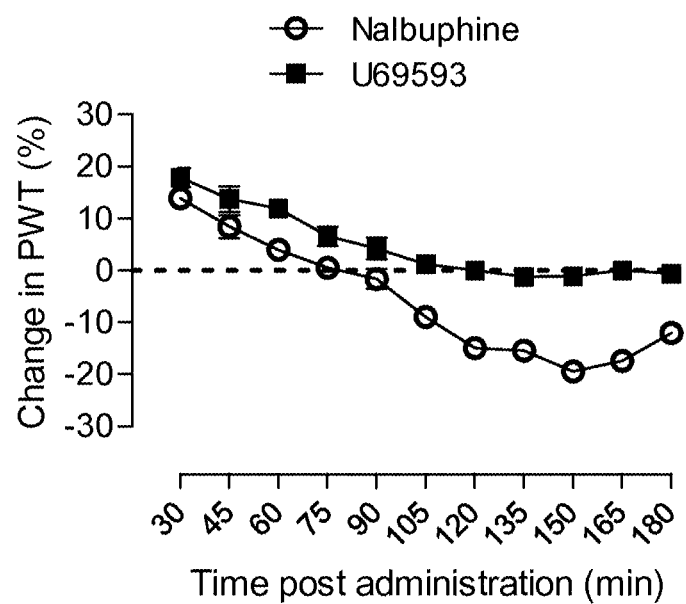
FIG. 12. The two receptor hypothesis.

The ability of κ-opioids to produce a separate anti-analgesia effect implies an action that involves at least two circuits in the central nervous system. In principle, a single receptor subtype could serve both functions by being present in each of the circuits. To test this possibility, nalbuphine or a selective κ-receptor agonist, U69593 was administered, to separate groups of rats (See FIG. 12: The two receptor hypothesis).

Nalbuphine induced early antinociception followed by anti-analgesia (pain greater than baseline); U69593 induced only antinociception, supporting the hypothesis that κ-receptors produce analgesia but not anti-analgesia. Because these results in the rat mimicked the results observed in humans, Applicants were able to use the rat model to identify the anti-analgesia receptor.

Identification of the Nociceptin/Orphanin FQ (NOP) Receptor as the "Anti-Analgesia" Receptor Since the anti-analgesic effect of nalbuphine is not mediated by κ-opioid receptors, a list of candidate anti-analgesia receptors was generated by conducting receptor binding assays for both nalbuphine and naloxone. Samples of nalbuphine (10 μM), naloxone (10 μM), and pentazocine (10 μM) were tested to determine their ability to inhibit binding of NOP, $\sigma_1$, and $\sigma_2$ ligand standards to their receptors.

TABLE 2

| | Inhibition (%) | | |
|---|---|---|---|
| | Nalbuphine | Naloxone | Pentazocine |
| Nociceptin/orphanin F/Q (NOP) | 12 | 19 | 24 |
| Sigma1 ($\sigma_1$) | −2 | 9 | 93 |
| Sigma2 ($\sigma_2$) | 15 | −2 | 81 |

Whereas all three drugs demonstrate binding to the NOP receptor, nalbuphine does not bind to the $\sigma_1$ receptor and naloxone does not bind to the $\sigma_2$ receptor. The NOP receptor was chosen because its activation at some brain sites has been associated with pain enhancement (Meunier J C et al., *Nature*, 377:532-535, 1995; Mogil J S et al., *Neuroscience*, 75:333-337, 1996). Sigma receptors were chosen because they have been suggested to have anti-analgesic effects (Chien C C and Pasternak G W, *Eur J Pharmacol*, 250:R7-8, 1993; Chien C C and Pasternak G W, *J Pharmacol Exp Ther*, 271:1583-1590, 1994).

Figure 13:
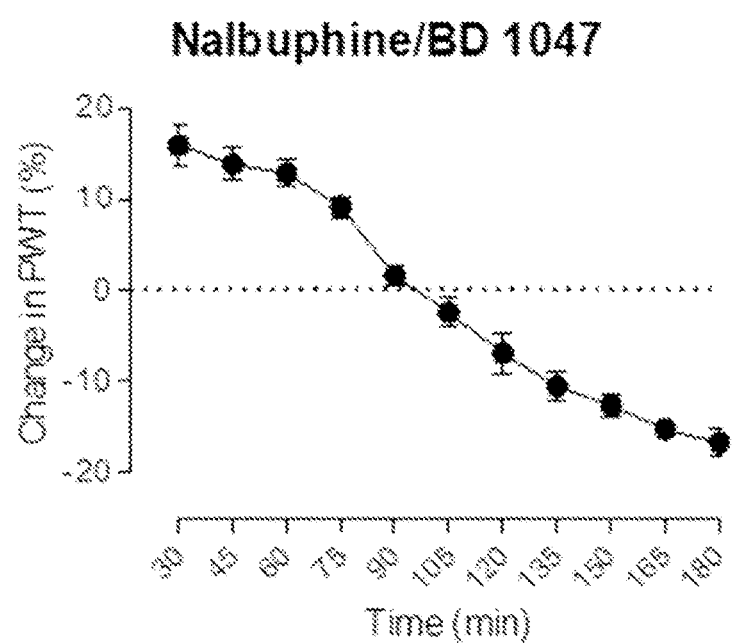
FIG. 13. Role of sigma receptors.

To test for a role of sigma receptors, Applicants co-administered nalbuphine and the sigma receptor antagonist BD1047 to a group of male rats (See FIG. 13: Role of sigma receptors).

The anti-analgesic effect of nalbuphine was not diminished in the presence of BD 1047, indicating that sigma receptors are not a likely source of κ-agonist-antagonist-induced anti-analgesia. Therefore it was tested for involvement of the NOP receptor.

Figure 14:
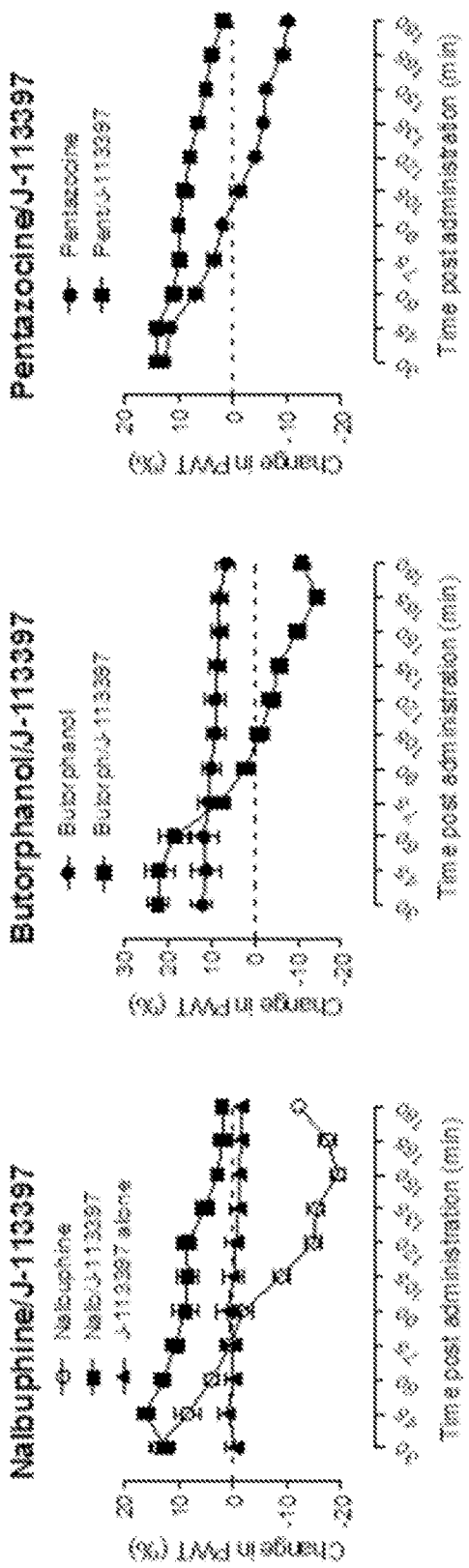
FIG. 14. Test of NOP receptor antagonist J-113397 against κ-agonist-antagonists.

The NOP receptor antagonist J-113397 was tested against all three κ-agonist-antagonists (See FIG. 14. Test of NOP receptor antagonist J-113397 against κ-agonist-antagonists). Nalbuphine (FIG. 14 left panel), butorphanol (FIG. 14 middle panel), and pentazocine (FIG. 14 right panel) each produced early antinociception followed at about 90 minutes with significant anti-analgesia. Administration of J-113397 blocked the anti-analgesic effect in all three cases, but had no effect when administered alone to a separate group of rats (FIG. 14 left panel). These findings implicate the NOP receptor in mediating the anti-analgesic effect of κ-agonist-antagonists.

Figure 15:
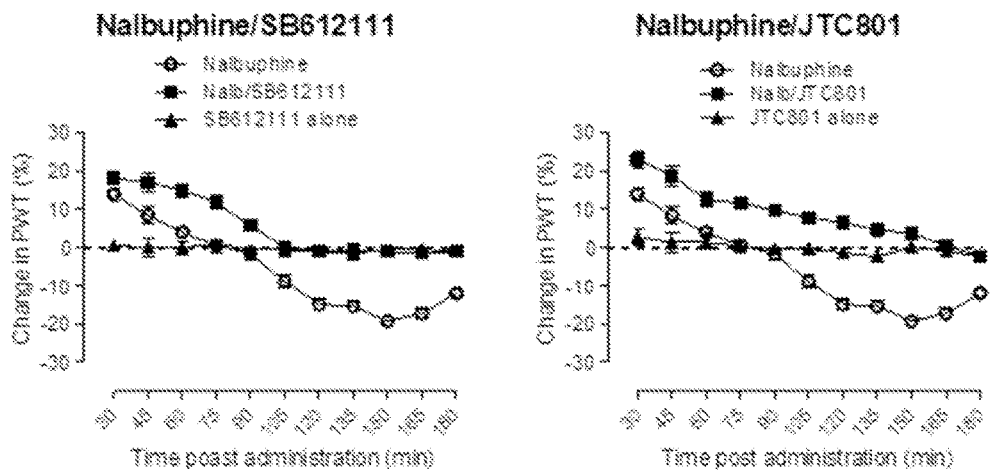
FIG. 15. Test of NOP receptor antagonists, SB-6112111 and JTC801.

To confirm this finding, Applicants tested two other NOP receptor antagonists, SB-6112111 and JTC801 (See FIG. 15: Test of NOP receptor antagonists, SB-6112111 and JTC801). Both SB6112111 (FIG. 15 left panel) and JTC801 (FIG. 15 right panel) blocked the anti-analgesic effect of nalbuphine but neither had any effect on nociceptive responses when administered alone. These findings are identical to those obtained with J-113397 and strongly support the suggestion that the NOP receptor produces anti-analgesia when activated by a κ-agonist-antagonist.

Figure 16:
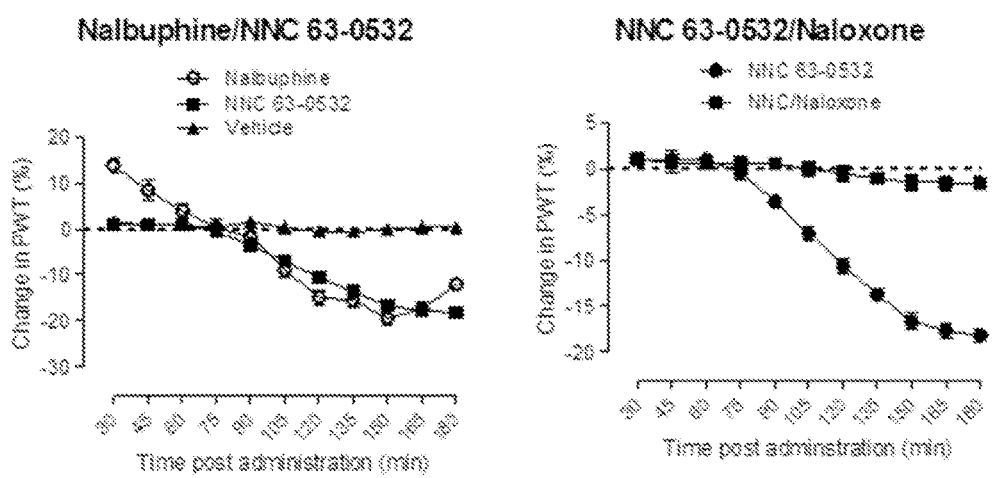
FIG. 16. Test of NOP receptor agonist NNC 63-0532.

To further confirm a role for the NOP receptor in anti-analgesia, Applicants tested whether the NOP receptor agonist NNC 63-0532 could produce anti-analgesia (See FIG. 16: Test of NOP receptor agonist NNC 63-0532). Nalbuphine, NNC 63-0532, and vehicle were administered to separate groups of rats (left panel). As previously observed, nalbuphine induced early analgesia followed by the onset of anti-analgesia about 90 minutes later. NNC 63-0532 produced no analgesia but did induce anti-analgesia at the same 90 minute time point. The magnitude of the NNC 63-0532-induced analgesia was indistinguishable from that of nalbuphine. Vehicle had no effect. Because the opioid antagonist naloxone had been found to block anti-analgesia induced by κ-agonist-antagonists, naloxone was co-administered with NNC 63-0532 to determine whether it could block anti-analgesia (FIG. 16 right panel). As observed previously with the κ-agonist-antagonists, naloxone complete blocked NNC 63-0532-induced anti-analgesia. Taken together these findings provide compelling evidence that the anti-analgesic effect of κ-agonist-antagonists is mediated by the NOP receptor.

Development of Compounds that Produce Analgesia by Acting at the κ-Opioid Receptor with or without Additional Action at the Mu-Opioid Receptor but do not Activate the Anti-Analgesic NOP Receptor.

Development of a κ-opioid agonists (e.g. with mild to moderate mu activity) that produces analgesia without producing accompanying anti-analgesia would have significant clinical benefits over the other major class of analgesics, μ-opioids such as morphine: less respiratory depression and less abuse potential. Compounds that produce analgesia at the κ-receptor and lack the ability to induce anti-analgesia at the NOP-receptor were developed and produced and tested for binding affinity to κ-, μ-, and NOP receptors.

TABLE 3

| Receptors | Tested compounds (% inhibition) | |
| --- | --- | --- |
| tested | 751612 | 751613 |
| Opiate κ (OP2, KOP) | 97 | 98 |
| Opiate μ (OP3, MOP) | 24 | 45 |
| Orphanin ORL1 or NOP | −2 | 20 |

Figure 17:
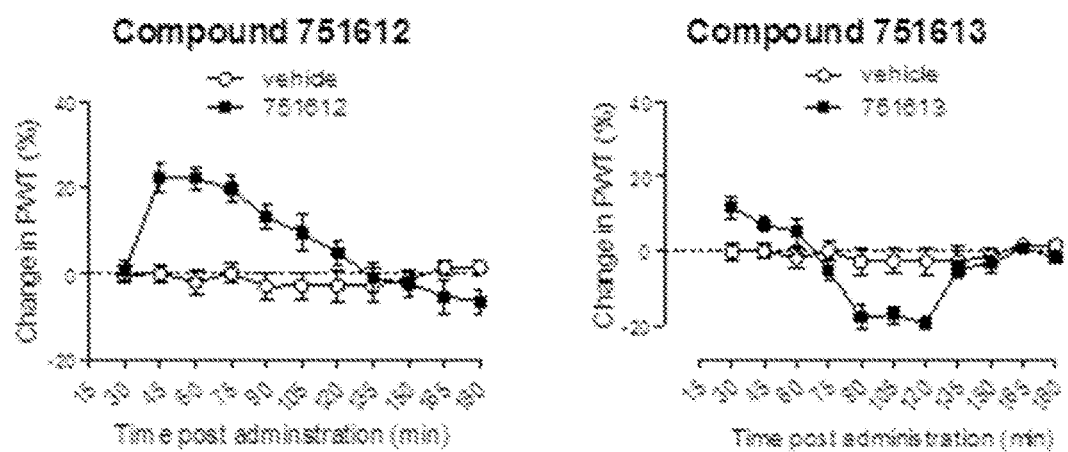
FIG. 17. Nociceptive testing of compound 751612 and 751613.

Although binding affinity (larger numbers) does not indicate if the compound is an agonist or antagonist at a particular receptor, it is possible to estimate how these compounds would perform in nociceptive testing. The most desirable characteristics would be low affinity for the NOP receptor and high affinity for the κ-receptor, provided the compound is a κ-receptor agonist. Nociceptive testing was performed for compounds 751612 and 751613. (See FIG. 17: Nociceptive testing of compound 751612 and 751613). Compound 751612 showed significant analgesia without significant anti-analgesia, suggesting that the behavioral profiles conformed reasonably well to the predictions based on the binding assays. On the other hand, compound 75613 showed 98% binding affinity for the κ-receptor but also 20% binding affinity for the NOP receptor. Nociceptive testing showed almost no analgesia but a typical anti-analgesic effect starting about 90 minutes, suggesting that his compound a NOP receptor agonist, similar to the κ-agonist-antagonists.

TABLE 4

Primary Binding Data. Data represent mean % inhibition (N = 4 determinations) for compound tested at receptor subtypes. Significant inhibition is considered >50%. In cases where negative inhibition (−) is seen, this represents a stimulation of binding. Occasionally, compounds at high concentrations will non-specifically increase binding. The default concentration for primary binding experiments is 10 μM.

| PDSP Number | Extraction PI | DOR | KOR | MOR |
| --- | --- | --- | --- | --- | --- |
| 26982 | Gallardo-Godoy | − | 43.8(AVE) | 96.1 | 4.2 |
| 26983 | Gallardo-Godoy | − | −1.8(AVE) | 98.6 | 25.5 |
| 26984 | Gallardo-Godoy | − | 4.2(AVE) | 60.6 | 31.4 |
| 26985 | Gallardo-Godoy | − | 2.5(AVE) | 92.3 | 31.9 |
| 26986 | Gallardo-Godoy | − | 12.4(AVE) | 99.4 | 44.6 |
| 26987 | Gallardo-Godoy | − | −1.78262 | 97.8 | 29.6 |
| 26988 | Gallardo-Godoy | − | −1.57687 | 98.9 | 29.8 |
| 26989 | Gallardo-Godoy | − | −2.81994 | 99.5 | 17.2 |

TABLE 4-continued

Primary Binding Data. Data represent mean % inhibition (N = 4 determinations) for compound tested at receptor subtypes. Significant inhibition is considered >50%. In cases where negative inhibition (−) is seen, this represents a stimulation of binding. Occasionally, compounds at high concentrations will non-specifically increase binding. The default concentration for primary binding experiments is 10 μM.

Extraction

| PDSP Number | PI | | DOR | KOR | MOR |
|---|---|---|---|---|---|
| 26990 | Gallardo-Godoy | − | 74.3235 | 51.7 | 10.4 |
| 26991 | Gallardo-Godoy | − | −0.494329 | 98.2 | 5.3 |
| 26992 | Gallardo-Godoy | − | 20.2474 | 63 | −3.9 |
| 26993 | Gallardo-Godoy | − | −2.39359 | 96.2 | 5.5 |
| 26994 | Gallardo-Godoy | − | 12.9266 | 98.9 | 69.2 |
| 26995 | Gallardo-Godoy | − | 36.7658 | 99.2 | 85.3 |
| 26996 | Gallardo-Godoy | − | 65.6456 | 99.2 | 87.7 |
| 26997 | Gallardo-Godoy | − | 9.97086 | 99.2 | 15.3 |
| 26998 | Gallardo-Godoy | − | 4.05995 | 99.4 | 66.5 |
| 26999 | Gallardo-Godoy | − | −5.15337 | 97.9 | 0.2 |
| 27000 | Gallardo-Godoy | − | 67.2511 | 99.1 | 92.9 |
| 27001 | Gallardo-Godoy | − | 8.84767 | 99.6 | 53.8 |
| 27002 | Gallardo-Godoy | − | 23.357 | 100.1 | 55.6 |
| 27003 | Gallardo-Godoy | − | 25.7477 | 99.4 | 69.9 |
| 27004 | Gallardo-Godoy | − | −3.8126 | 98 | 6.1 |
| 27005 | Gallardo-Godoy | − | −0.75704 | 99.7 | 27.9 |
| 27006 | Gallardo-Godoy | − | 20.9079 | 98.3 | −3.2 |
| 27007 | Gallardo-Godoy | − | 5.24887 | 99.8 | 19.5 |
| 27008 | Gallardo-Godoy | − | 21.21 | 99.5 | 62 |
| 27009 | Gallardo-Godoy | − | 2.10063 | 99.1 | 32.1 |
| 27010 | Gallardo-Godoy | − | 0.826673 | 95 | 2.3 |
| 27011 | Gallardo-Godoy | − | −3.08887 | 94.3 | 3.5 |
| 27012 | Gallardo-Godoy | − | −2.83973 | 68.8 | 14.1 |
| 27013 | Gallardo-Godoy | − | 31.7472 | 61 | 2.7 |
| 27014 | Gallardo-Godoy | − | −10.5096 | 6.1 | 3.6 |
| 27015 | Gallardo-Godoy | − | −16.8821 | 80.1 | 18.7 |
| 27016 | Gallardo-Godoy | − | −7.12766 | 68.1 | 47.8 |
| 27017 | Gallardo-Godoy | − | −8.00959 | 78.9 | 36 |
| 27018 | Gallardo-Godoy | − | 0.267733 | 75 | 20 |
| 27019 | Gallardo-Godoy | − | 3.26454 | 34.7 | 4.7 |
| 27020 | Gallardo-Godoy | − | 2.78505 | 87.9 | 23.6 |
| 27021 | Gallardo-Godoy | − | 4.50584 | 99.6 | 23.3 |
| 27022 | Gallardo-Godoy | − | −4.48177 | 98.7 | 13.9 |
| 27023 | Gallardo-Godoy | − | 16.3096 | 37.8 | 21 |
| 27024 | Gallardo-Godoy | − | −2.37671 | 54.3 | 20.6 |
| 27025 | Gallardo-Godoy | − | −9.30102 | 97.3 | 8.4 |
| 27026 | Gallardo-Godoy | − | 8.35601 | 42.3 | 7.7 |
| 27027 | Gallardo-Godoy | − | −3.89389 | 40.7 | 11.2 |
| 27028 | Gallardo-Godoy | − | −6.97444 | 45.4 | 30.2 |
| 27029 | Gallardo-Godoy | − | −8.61063 | 96.7 | 11.1 |
| 27030 | Gallardo-Godoy | − | 26.4623 | 99.1 | 70 |
| 27031 | Gallardo-Godoy | − | 81.0308 | 99 | 92.8 |
| 27032 | Gallardo-Godoy | − | 93.4278 | 99.9 | 98.6 |
| 27033 | Gallardo-Godoy | − | 96.2618 | 99.3 | 98.8 |
| 27034 | Gallardo-Godoy | − | 25.5138 | 98.1 | 90.4 |
| 27035 | Gallardo-Godoy | − | 95.2793 | 90.5 | 93.8 |

Legend: 1° Assay Scheduled | Complete | 2° Assay Scheduled | 2° Assay or Functional Completed | Redo | In Progress | Pending Approval

TABLE 5

Binding Ki Data. Unless otherwise indicated (see Note), data represent Ki (nM) values obtained from non-linear regression of radioligand competition binding isotherms. Ki values are calculated from best fit IC50 values using the Cheng-Prusoff equation.

Extraction-1

| PDSP Number | PI | | DOR | KOR | MOR |
|---|---|---|---|---|---|
| 26982 | Gallardo-Godoy | − | | 78 | |
| 26983 | Gallardo-Godoy | − | | 17 | |
| 26984 | Gallardo-Godoy | − | | 890 | |

TABLE 5-continued

Binding Ki Data. Unless otherwise indicated (see Note), data represent Ki (nM) values obtained from non-linear regression of radioligand competition binding isotherms. Ki values are calculated from best fit IC50 values using the Cheng-Prusoff equation.
Extraction-1

| PDSP Number | PI | DOR | KOR | MOR |
|---|---|---|---|---|
| 26985 | Gallardo-Godoy | – | 112 | |
| 26986 | Gallardo-Godoy | – | 10 | |
| 26987 | Gallardo-Godoy | – | 14 | |
| 26988 | Gallardo-Godoy | – | 19 | |
| 26989 | Gallardo-Godoy | – | 18 | |
| 26990 | Gallardo-Godoy | – | 530 | 1,999.00 |
| 26991 | Gallardo-Godoy | – | 98 | |
| 26992 | Gallardo-Godoy | – | >10,000 | |
| 26993 | Gallardo-Godoy | – | 78 | |
| 26994 | Gallardo-Godoy | – | 0.7 | 1,755.00 |
| 26995 | Gallardo-Godoy | – | 0.4 | 601 |
| 26996 | Gallardo-Godoy | – | 591 | 0.4 | 337 |
| 26997 | Gallardo-Godoy | – | 2,328.00 | |
| 26998 | Gallardo-Godoy | – | 2.2 | 1,928.00 |
| 26999 | Gallardo-Godoy | – | 64 | |
| 27000 | Gallardo-Godoy | – | 368 | 0.5 | 156 |
| 27001 | Gallardo-Godoy | – | 0.6 | 2,447.00 |
| 27002 | Gallardo-Godoy | – | 0.7 | 2,194.00 |
| 27003 | Gallardo-Godoy | – | 0.5 | 2,043.00 |
| 27004 | Gallardo-Godoy | – | 50 | |
| 27005 | Gallardo-Godoy | – | 1.8 | |
| 27006 | Gallardo-Godoy | – | 59 | |
| 27007 | Gallardo-Godoy | – | 1.7(AVE) | |
| 27008 | Gallardo-Godoy | – | 0.4 | >10,000 |
| 27009 | Gallardo-Godoy | – | 7.7(AVE) | |
| 27010 | Gallardo-Godoy | – | 358 | |
| 27011 | Gallardo-Godoy | – | 73 | |
| 27012 | Gallardo-Godoy | – | 146 | |
| 27013 | Gallardo-Godoy | – | 204 | |
| 27014 | Gallardo-Godoy | – | | |
| 27015 | Gallardo-Godoy | – | 1,735.00 | |
| 27016 | Gallardo-Godoy | – | >10,000 | |
| 27017 | Gallardo-Godoy | – | >10,000 | |
| 27018 | Gallardo-Godoy | – | >10,000 | |
| 27019 | Gallardo-Godoy | – | | |
| 27020 | Gallardo-Godoy | – | 2.6 | |

TABLE 5-continued

Binding Ki Data. Unless otherwise indicated (see Note), data represent Ki (nM) values obtained from non-linear regression of radioligand competition binding isotherms. Ki values are calculated from best fit IC50 values using the Cheng-Prusoff equation.

Extraction-1

| PDSP Number | PI | DOR | KOR | MOR |
|---|---|---|---|---|
| 27021 | Gallardo-Godoy | – | 1.2 | |
| 27022 | Gallardo-Godoy | – | 9.6 | |
| 27023 | Gallardo-Godoy | – | | |
| 27024 | Gallardo-Godoy | – | 1,229.00 | |
| 27025 | Gallardo-Godoy | – | 16 | |
| 27026 | Gallardo-Godoy | – | | |
| 27027 | Gallardo-Godoy | – | | |
| 27028 | Gallardo-Godoy | – | | |
| 27029 | Gallardo-Godoy | – | 40 | |
| 27030 | Gallardo-Godoy | – | 0.2 | 2,535.00 |
| 27031 | Gallardo-Godoy | – | 168 | 0.9 | 289 |
| 27032 | Gallardo-Godoy | – | 72 | 0.2 | 4.9 |
| 27033 | Gallardo-Godoy | – | 56 | 0.1 | 19 |
| 27034 | Gallardo-Godoy | – | 0.2 | 357 |
| 27035 | Gallardo-Godoy | – | 42 | 0.3 | 1.1 |

Legend: Complete  2° Assay Scheduled  1° Assay < 50%  Redo  In Progress  Pending Approval  Under Review Note:
When the Hill coefficient (nH) is significantly different from −1 (assessed by F test), the IC50 and nH are reported instead of the Ki.
A * next to a value denotes IC50.

TABLE 6

Functional NOP Agonism. Agonist assays. Data represent the percent efficacy (relative to cognate agonist) of the test compound at 10 micromolar. The response to a saturating concentration of cognate/reference agonist is set to 100%; the response to a saturating concentration of a reference antagonist or to vehicle (usually none or negligible) is set to 0%. Antagonist assays: Data represent the percent inhibition of the response to an EC90 concentration (empirically determined immediately prior to assay) of cognate/reference agonist by the test compound at 10 micromolar. The response inhibition elicited by a saturating concentration of reference antagonist is set to 100%; the response inhibition (usually none or negligible) elicited by vehicle is set to 0%. HEK T assays: Data represent the percent activity of test compounds relative to a reference agonist (TRAP for calcium flux assays, Isoproterenol for cAMP assays).

Extraction-3

| PDSP Number | PI | | NOP Tango Agonist |
|---|---|---|---|
| 26982 | Gallardo-Godoy | – | −4.3 |
| 26983 | Gallardo-Godoy | – | 0.9 |
| 26984 | Gallardo-Godoy | – | 1.7 |
| 26985 | Gallardo-Godoy | – | −2.7 |
| 26986 | Gallardo-Godoy | – | 0.7 |
| 26987 | Gallardo-Godoy | – | −1.9 |
| 26988 | Gallardo-Godoy | – | 1.9 |
| 26989 | Gallardo-Godoy | – | −0.2 |
| 26990 | Gallardo-Godoy | – | −1.6 |
| 26991 | Gallardo-Godoy | – | 0 |
| 26992 | Gallardo-Godoy | – | −5 |
| 26993 | Gallardo-Godoy | – | −2.6 |
| 26994 | Gallardo-Godoy | – | −3.4 |
| 26995 | Gallardo-Godoy | – | −2.6 |
| 26996 | Gallardo-Godoy | – | −3.9 |

TABLE 6-continued

Functional NOP Agonism. Agonist assays. Data represent the percent efficacy (relative to cognate agonist) of the test compound at 10 micromolar. The response to a saturating concentration of cognate/reference agonist is set to 100%; the response to a saturating concentration of a reference antagonist or to vehicle (usually none or negligible) is set to 0%. Antagonist assays: Data represent the percent inhibition of the response to an EC90 concentration (empirically determined immediately prior to assay) of cognate/reference agonist by the test compound at 10 micromolar. The response inhibition elicited by a saturating concentration of reference antagonist is set to 100%; the response inhibition (usually none or negligible) elicited by vehicle is set to 0%. HEK T assays: Data represent the percent activity of test compounds relative to a reference agonist (TRAP for calcium flux assays, Isoproterenol for cAMP assays).
Extraction-3

| PDSP Number | PI | | NOP Tango Agonist |
|---|---|---|---|
| 26997 | Gallardo-Godoy | – | −3.3 |
| 26998 | Gallardo-Godoy | – | −2.8 |
| 26999 | Gallardo-Godoy | – | −4 |
| 27000 | Gallardo-Godoy | – | −1.3 |
| 27001 | Gallardo-Godoy | – | 1.1 |
| 27002 | Gallardo-Godoy | – | −4.2 |
| 27003 | Gallardo-Godoy | – | −3.3 |
| 27004 | Gallardo-Godoy | – | −3.3 |
| 27005 | Gallardo-Godoy | – | −3.2 |
| 27006 | Gallardo-Godoy | – | −3.5 |
| 27007 | Gallardo-Godoy | – | −1 |
| 27008 | Gallardo-Godoy | – | −2.6 |
| 27009 | Gallardo-Godoy | – | −4.2 |
| 27010 | Gallardo-Godoy | – | −2.9 |
| 27011 | Gallardo-Godoy | – | −4.7 |
| 27012 | Gallardo-Godoy | – | −4.7 |
| 27013 | Gallardo-Godoy | – | −3.6 |
| 27014 | Gallardo-Godoy | – | −4.9 |
| 27015 | Gallardo-Godoy | – | −5.2 |
| 27016 | Gallardo-Godoy | – | −5 |
| 27017 | Gallardo-Godoy | – | −3.6 |
| 27018 | Gallardo-Godoy | – | −3.9 |
| 27019 | Gallardo-Godoy | – | −1.9 |
| 27020 | Gallardo-Godoy | – | −0.2 |
| 27021 | Gallardo-Godoy | – | −2.2 |
| 27022 | Gallardo-Godoy | – | 0.2 |
| 27023 | Gallardo-Godoy | – | −2.6 |
| 27024 | Gallardo-Godoy | – | −2.3 |
| 27025 | Gallardo-Godoy | – | −5 |
| 27026 | Gallardo-Godoy | – | −1.2 |
| 27027 | Gallardo-Godoy | – | −4.8 |
| 27028 | Gallardo-Godoy | – | −3 |
| 27029 | Gallardo-Godoy | – | 9 |
| 27030 | Gallardo-Godoy | – | −4.4 |
| 27031 | Gallardo-Godoy | – | −2.9 |
| 27032 | Gallardo-Godoy | – | −1.6 |
| 27033 | Gallardo-Godoy | – | −1.9 |
| 27034 | Gallardo-Godoy | – | −2.9 |
| 27035 | Gallardo-Godoy | – | 3.5 |

| Legend: | 1° Assay Scheduled | Complete | 2° Assay Scheduled | 2° Assay or Functional Completed | Redo | In Progress | Pending Approval | Hit | Miss | Undetermined |

TABLE 7

Specific Embodiments.

| PDSP No. | SMDC No. | Cmpd. Alias | KOR | KOR Ki | DOR | DOR Ki | MOR | MOR Ki | NOP Tango Agonist | MW | MW as Salt |
|---|---|---|---|---|---|---|---|---|---|---|---|
| 26982 | 751609 | LALS-SKY-R1Y1 | 96 | 78 | 44 | | 4 | | −4.3 | 322.4 | 358.9 |
| 26983 | 751664 | LALS-SKY-R1Y2 | 99 | 17 | −2 | | 26 | 0.9 | | 362.5 | 398.9 |

TABLE 7-continued

Specific Embodiments.

| PDSP No. | SMDC No. | Cmpd. Alias | KOR | KOR Ki | DOR | DOR Ki | MOR | MOR Ki | NOP Tango Agonist | MW | MW as Salt |
|---|---|---|---|---|---|---|---|---|---|---|---|
| 26984 | 751610 | LALS-SKY-R1Y3 | 61 | 890 | 4 | | 31 | | 1.7 | 342.9 | 379.3 |
| 26985 | 751665 | LALS-SKY-R1Y4 | 92 | 112 | 3 | | 32 | | -2.7 | 391.6 | 428 |
| 26986 | 751611 | LALS-SKY-R2Y1 | 99 | 10 | 12 | | 45 | | 0.7 | 405.4 | 441.8 |

TABLE 7-continued

Specific Embodiments.

| PDSP No. | SMDC No. | Cmpd. Alias | KOR | KOR Ki | DOR | DOR Ki | MOR | MOR Ki | NOP Tango Agonist | MW | MW as Salt |
|---|---|---|---|---|---|---|---|---|---|---|---|
| 26987 | 751612 | LALS-SKY-R2Y2 | 98 | 14 | −2 | | 30 | | −1.9 | 335.5 | 403 |
| 26988 | 751613 | LALS-SKY-R2Y3 | 99 | 19 | −2 | | 30 | | 1.9 | 376.5 | 412.9 |
| 26989 | 751666 | LALS-SKY-R2Y4 | 100 | 18 | −3 | | 17 | | −0.2 | 376.5 | 412.9 |

TABLE 7-continued
Specific Embodiments.
| PDSP No. | SMDC No. | Cmpd. Alias | KOR | KOR Ki | DOR | DOR Ki | MOR | MOR Ki | NOP Tango Agonist | MW | MW as Salt | Structure |
|---|---|---|---|---|---|---|---|---|---|---|---|---|
| 26990 | 751614 | LALS-SKY-R2Y5 | 52 | 2.00E+03 | 74 | 530 | 10 | | −1.6 | 356.9 | 393.4 | 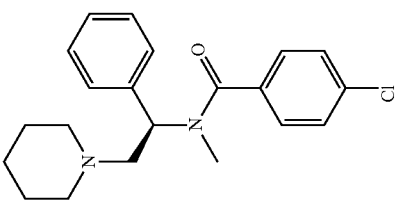 |
| 26991 | 751667 | LALS-SKY-R2Y6 | 98 | 98 | 0 | | 5 | | 0 | 405.6 | 442 | |
| 26992 | 751668 | LALS-SKY-R2Y7 | 63 | >10,000 | 20 | | −4 | | −5 | 343.5 | 379.9 | 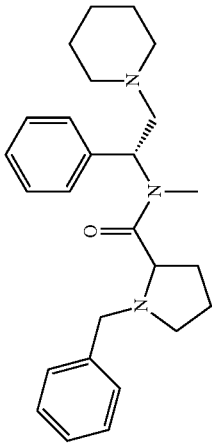 |

TABLE 7-continued

Specific Embodiments.

| PDSP No. | SMDC No. | Cmpd. Alias | KOR | KOR Ki | DOR | DOR Ki | MOR | MOR Ki | NOP Tango Agonist | MW | MW as Salt |
|---|---|---|---|---|---|---|---|---|---|---|---|
| 26993 | 751615 | LALS-SKY-R2Y9 | 96 | 78 | -2 | | 6 | | -2.6 | 336.5 | 372.9 |
| 26994 | 751616 | LALS-SKY-S1Y1 | 99 | 0.7 | 13 | | 69 | 1.76E+03 | -3.4 | 322.4 | 358.9 |

TABLE 7-continued

Specific Embodiments.

| PDSP No. | SMDC No. | Cmpd. Alias | KOR | KOR Ki | DOR | DOR Ki | MOR | MOR Ki | NOP Tango Agonist | MW | MW as Salt |
|---|---|---|---|---|---|---|---|---|---|---|---|
| 26995 | 751617 | LALS-SKY-S1Y2 | 99 | 0.4 | 37 | | 85 | 601 | -2.6 | 321.4 | 388.9 |
| 26996 | 751618 | LALS-SKY-S1Y3 | 99 | 0.4 | 66 | 591 | 88 | 337 | -3.9 | 362.5 | 398.9 |

TABLE 7-continued

Specific Embodiments.

| PDSP No. | SMDC No. | Cmpd. Alias | KOR | KOR Ki | DOR | DOR Ki | MOR | MOR Ki | NOP Tango Agonist | MW | MW as Salt |
|---|---|---|---|---|---|---|---|---|---|---|---|
| 26997 | 751619 | LALS-SKY-S1Y4 | 99 | 2.33E+03 | 10 | | 15 | | −3.3 | 342.9 | 379.3 |
| 26998 | 751669 | LALS-SKY-S1Y5 | 99 | 2.2 | 4 | | 67 | 1.93E+0.3 | −2.8 | 391.6 | 428 |
| 26999 | 751670 | LALS-SKY-SY16 | 98 | 64 | −5 | | 0 | | −4 | 329.4 | 365.9 |

TABLE 7-continued
Specific Embodiments.
| PDSP No. | SMDC No. | Cmpd. Alias | KOR | KOR Ki | DOR | DOR Ki | MOR | MOR Ki | NOP Tango Agonist | MW | MW as Salt |
|---|---|---|---|---|---|---|---|---|---|---|---|
| 27000 | 751620 | LALS-SKY-S2Y1 | 99 | 0.5 | 67 | 368 | 93 | 156 | -1.3 | 405.4 | 441.8 |
| 27001 | 751621 | LALS-SKY-S2Y2 | 100 | 0.6 | 9 | | 54 | 2.45E+03 | 1.1 | 335.5 | 403 |
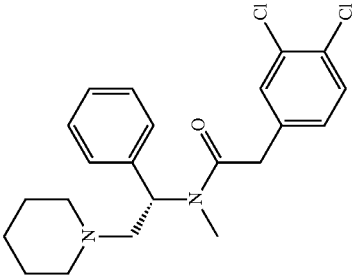
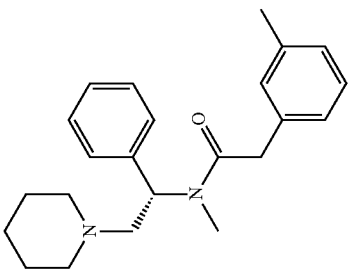

TABLE 7-continued

Specific Embodiments.

| PDSP No. | SMDC No. | Cmpd. Alias | KOR | KOR Ki | DOR | DOR Ki | MOR | MOR Ki | NOP Tango Agonist | MW | MW as Salt |
|---|---|---|---|---|---|---|---|---|---|---|---|
| 27002 | 751622 | LALS-SKY-S2Y3 | 100 | 0.7 | 23 | | 56 | 2.19E+03 | −4.2 | 376.5 | 412.9 |
| 27003 | 751688 | LALS-SKY-S2Y4 | 99 | 0.5 | 26 | | 70 | 2.04E+03 | −3.3 | 376.5 | 412.9 |
| 27004 | 751623 | LALS-SKY-S2Y5 | 98 | 50 | −4 | | 6 | | −3.3 | 356.9 | 393.4 |

TABLE 7-continued

Specific Embodiments.

| PDSP No. | SMDC No. | Cmpd. Alias | KOR | KOR Ki | DOR | DOR Ki | MOR | MOR Ki | NOP Tango Agonist | MW | MW as Salt |
|---|---|---|---|---|---|---|---|---|---|---|---|
| 27005 | 751671 | LALS-SKY-S2Y6 | 100 | 1.8 | −1 | | 28 | | −3.2 | 405.6 | 442 |
| 27006 | 751672 | LALS-SKY-S2Y7 | 98 | 59 | 21 | | −3 | | −3.5 | 343.5 | 379.9 |
| 27007 | 751624 | LALS-SKY-S2Y9 | 100 | 1.7 | 5 | | 20 | | −1 | 336.5 | 372.9 |

TABLE 7-continued
Specific Embodiments.
| PDSP No. | SMDC No. | Cmpd. Alias | KOR | KOR Ki | DOR | DOR Ki | MOR | MOR Ki | NOP Tango Agonist | MW | MW as Salt | Structure |
|---|---|---|---|---|---|---|---|---|---|---|---|---|
| 27008 | 751689 | Q2-SS88-1 | 100 | 0.4 | 21 | | 62 | >10,000 | −2.6 | 340.5 | 376.9 | 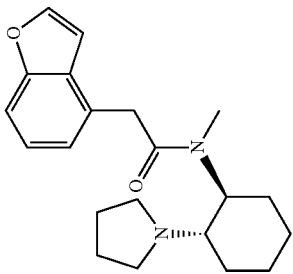 |
| 27009 | 751690 | Q2-SS88-2 | 99 | 7.7 | 2 | | 32 | | −4.2 | 300.4 | 346.9 | 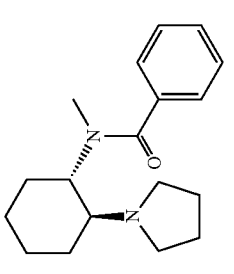 |
| 27010 | 751691 | Q2-SS88-3 | 95 | 358 | 1 | | 2 | | −2.9 | 302.4 | 338.9 | 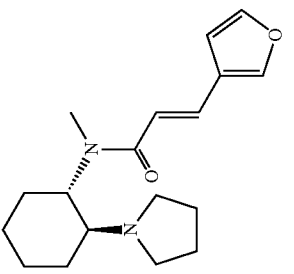 |

TABLE 7-continued

Specific Embodiments.

| PDSP No. | SMDC No. | Cmpd. Alias | KOR | KOR Ki | DOR | DOR Ki | MOR | MOR Ki | NOP Tango Agonist | MW | MW as Salt |
|---|---|---|---|---|---|---|---|---|---|---|---|
| 27011 | 751692 | Q2-SS88-4 | 94 | 73 | −3 | | 4 | | −4.7 | 286.4 | 322.9 |
| 27012 | 751693 | Q2-SS88-5 | 69 | 146 | −3 | | 14 | | −4.7 | 369.5 | 406 |
| 27013 | 751870 | Q2-SS88-6 | 61 | 204 | 32 | | 3 | | −3.6 | 355.5 | 392 |

TABLE 7-continued

Specific Embodiments.

| PDSP No. | SMDC No. | Cmpd. Alias | KOR | KOR Ki | DOR | DOR Ki | MOR | MOR Ki | NOP Tango Agonist | MW | MW as Salt |
|---|---|---|---|---|---|---|---|---|---|---|---|
| 27014 | 751871 | Q2-SS88-7 | 6 | | −11 | | 4 | | −4.9 | 293.4 | 329.9 |
| 27015 | 751694 | Q2-SS88-8 | 80 | 1.74E+03 | −1.7 | | 19 | | −5.2 | 307.4 | 343.9 |
| 27016 | 751695 | Q2-SS88-9 | 68 | >10,000 | −7 | | 48 | | −5 | 423.6 | 460.1 |

TABLE 7-continued
Specific Embodiments.
| PDSP No. | SMDC No. | Cmpd. Alias | KOR | KOR Ki | DOR | DOR Ki | MOR | MOR Ki | NOP Tango Agonist | MW | MW as Salt |
|---|---|---|---|---|---|---|---|---|---|---|---|
| 27017 | 751696 | Q2-SS88-10 | 79 | >10,000 | −8 | | 36 | | −3.6 | 409.6 | 446.1 |
| 27018 | 751697 | Q2-SS88-11 | 75 | >10,000 | 0 | | 20 | | −3.9 | 313.4 | 349.9 |
| 27109 | 751698 | Q2-SS88-11A | 35 | | 3 | | 5 | | −1.9 | 313.4 | 349.9 |
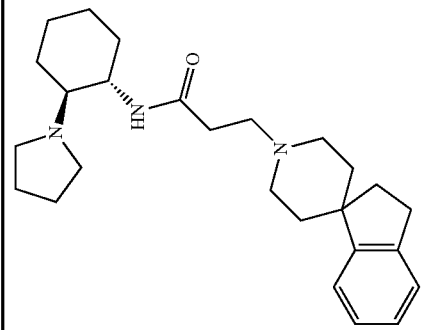 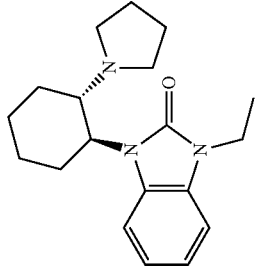 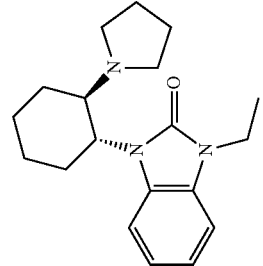

TABLE 7-continued

Specific Embodiments.

| PDSP No. | SMDC No. | Cmpd. Alias | KOR | KOR Ki | DOR | DOR Ki | MOR | MOR Ki | NOP Tango Agonist | MW | MW as Salt |
|---|---|---|---|---|---|---|---|---|---|---|---|
| 27020 | 751699 | Q3-S37-1 | 88 | 2.6 | 3 | | 24 | | −0.2 | 326.4 | 362.9 |
| 27021 | 751700 | Q3-S37-2 | 100 | 1.2 | 5 | | 23 | | −2.2 | 330.4 | 366.9 |
| 27022 | 751701 | Q3-S37-3 | 99 | 9.6 | −4 | | 14 | | 0.2 | 286.4 | 322.9 |

TABLE 7-continued

Specific Embodiments.

| PDSP No. | SMDC No. | Cmpd. Alias | KOR | KOR Ki | DOR | DOR Ki | MOR | MOR Ki | NOP Tango Agonist | MW | MW as Salt |
|---|---|---|---|---|---|---|---|---|---|---|---|
| 27023 | 751702 | Q3-S37-4 | 38 | | 16 | | 21 | | −2.6 | 288.4 | 324.8 |
| 27024 | 751703 | Q3-S37-5 | 54 | 1.23E+03 | −2 | | 21 | | −2.3 | 272.4 | 308.9 |
| 27025 | 751704 | Q3-S37-6 | 97 | 16 | −9 | | 8 | | −5 | 355.5 | 392 |

TABLE 7-continued

Specific Embodiments.

| PDSP No. | SMDC No. | Cmpd. Alias | KOR | KOR Ki | DOR | DOR Ki | MOR | MOR Ki | NOP Tango Agonist | MW | MW as Salt |
|---|---|---|---|---|---|---|---|---|---|---|---|
| 27026 | 751705 | Q3-S37-7 | 42 | | 8 | | 8 | | −1.2 | 293.4 | 329.9 |
| 27027 | 751706 | Q3-S37-8 | 41 | | −4 | | 11 | | −4.8 | 292.5 | 329 |
| 27028 | 751707 | Q3-S37-10 | 45 | | −7 | | 30 | | −3 | 412.6 | 449.1 |

TABLE 7-continued
Specific Embodiments.
| PDSP No. | SMDC No. | Cmpd. Alias | KOR | KOR Ki | DOR | DOR Ki | MOR | MOR Ki | NOP Tango Agonist | MW | MW as Salt |
|---|---|---|---|---|---|---|---|---|---|---|---|
| 27029 | 751708 | Q3-S37-11 | 97 | 40 | −9 | | 11 | | 9 | 341.5 | 377.9 |
| 27030 | 751629 | BRL 52537 | 99 | 0.2 | 26 | 70 | | 2.54E+03 | −4.4 | 355.3 | 396.3 |
| 27033 | 751630 | ICI 199,441 | 99 | 0.1 | 96 | 56 | 99 | 19 | −1.9 | 391.4 | 427.8 |
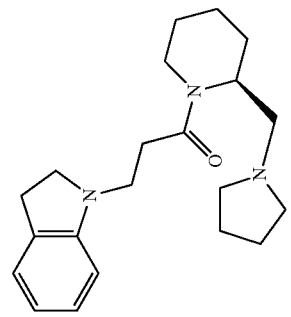 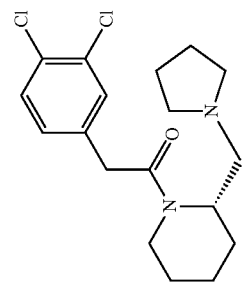 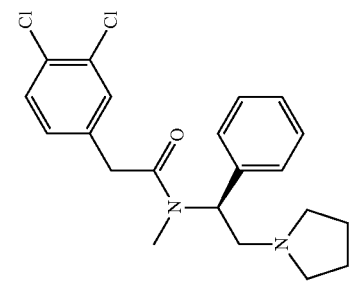

TABLE 7-continued
Specific Embodiments.
| PDSP No. | SMDC No. | Cmpd. Alias | KOR | KOR Ki | DOR | DOR Ki | MOR | MOR Ki | NOP Tango Agonist | MW | MW as Salt |
|---|---|---|---|---|---|---|---|---|---|---|---|
| 27035 | 701713 | TRK-820 HCl | 91 | 0.3 | 95 | 42 | 94 | 1.1 | 3.5 | 476.6 | 513 |
| | | Q2-SS88-12 | | | | | | | | 411.6 | |
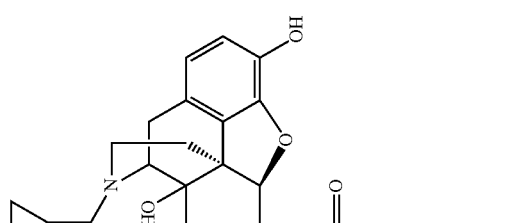
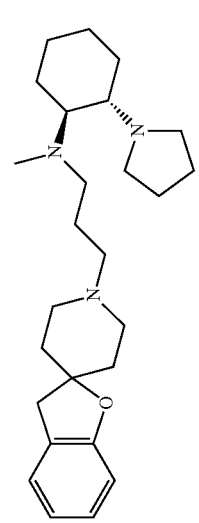

TABLE 7-continued
Specific Embodiments.
| PDSP No. | SMDC No. | Cmpd. Alias | KOR | KOR Ki | DOR | DOR Ki | MOR | MOR Ki | NOP Tango Agonist | MW | MW as Salt |
|---|---|---|---|---|---|---|---|---|---|---|---|
| | | | | | | | | | | 491.6 | |
| | | | | | | | | | | 218.3 | |
| | | | | | | | | | | 218.3 | |
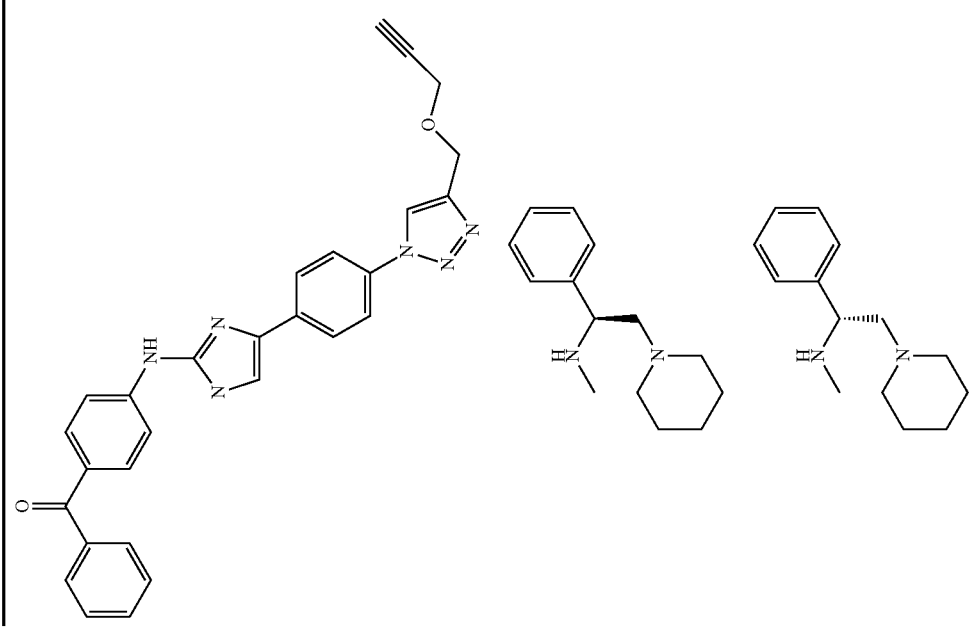

TABLE 7-continued
Specific Embodiments.
| PDSP No. | SMDC No. | Cmpd. Alias | KOR | KOR Ki | DOR | DOR Ki | MOR | MOR Ki | NOP Tango Agonist | MW | MW as Salt |
|---|---|---|---|---|---|---|---|---|---|---|---|
| | | 1-Q2-SS88 | | | | | | | | 204.3 | |
| | | 2-Q2-SS88 | | | | | | | | | |
| | | 3-Q2-SS88 | | | | | | | | | |
| | | 4-Q2-SS88 | | | | | | | | | |
| | | 5-Q2-SS88 | | | | | | | | | |
| | | 6-Q2-SS88 | | | | | | | | 204.3 | |
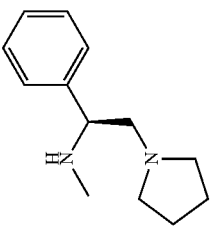
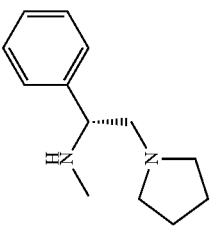
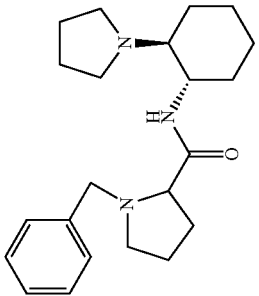

TABLE 7-continued

Specific Embodiments.

| PDSP No. | SMDC No. | Cmpd. Alias | KOR | KOR Ki | DOR | DOR Ki | MOR | MOR Ki | NOP Tango Agonist | MW | MW as Salt |
|---|---|---|---|---|---|---|---|---|---|---|---|
| | | 7-Q2-SS88 | | | | | | | | | |
| | | 8-Q2-SS88 | | | | | | | | | |
| | | 9-Q2-SS88 | | | | | | | | | |

TABLE 7-continued

Specific Embodiments.

| PDSP No. | SMDC No. | Cmpd. Alias | KOR | KOR Ki | DOR | DOR Ki | MOR | MOR Ki | NOP Tango Agonist | MW | MW as Salt |
|---|---|---|---|---|---|---|---|---|---|---|---|

10-Q2-SS88

11-Q2-SS88

12-Q2-SS88

TABLE 7-continued

Specific Embodiments.

| PDSP No. | SMDC No. | Cmpd. Alias | KOR | KOR Ki | DOR | DOR Ki | MOR | MOR Ki | NOP Tango Agonist | MW | MW as Salt |
|---|---|---|---|---|---|---|---|---|---|---|---|

13-Q2-SS88

1-Q3-S37

2-Q3-S37

TABLE 7-continued

Specific Embodiments.

| PDSP No. | SMDC No. | Cmpd. Alias | KOR | KOR Ki | DOR | DOR Ki | MOR | MOR Ki | NOP Tango Agonist | MW | MW as Salt |
|---|---|---|---|---|---|---|---|---|---|---|---|
| | | 3-Q3-S37 | | | | | | | | | |
| | | 4-Q3-S37 | | | | | | | | | |
| | | 5-Q3-S37 | | | | | | | | | |

TABLE 7-continued

Specific Embodiments.

| PDSP No. | SMDC No. | Cmpd. Alias | KOR | KOR Ki | DOR | DOR Ki | MOR | MOR Ki | NOP Tango Agonist | MW | MW as Salt |
|---|---|---|---|---|---|---|---|---|---|---|---|
| | | 6-Q3-S37 | | | | | | | | | |
| | | 7-Q3-S37 | | | | | | | | | |
| | | 8-Q3-S37 | | | | | | | | | |

TABLE 7-continued

Specific Embodiments.

| PDSP No. | SMDC No. | Cmpd. Alias | KOR | KOR Ki | DOR | DOR Ki | MOR | MOR Ki | NOP Tango Agonist | MW | MW as Salt |
|---|---|---|---|---|---|---|---|---|---|---|---|
| | | 11-Q3-S37 | | | | | | | | | |
| | | Int-R01 | | | | | | | | | |

TABLE 7-continued
Specific Embodiments.
| PDSP No. | SMDC No. | Cmpd. Alias | KOR | KOR Ki | DOR | DOR Ki | MOR | MOR Ki | NOP Tango Agonist | MW | MW as Salt |
|---|---|---|---|---|---|---|---|---|---|---|---|
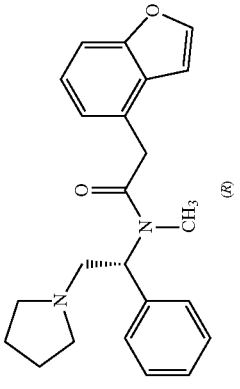
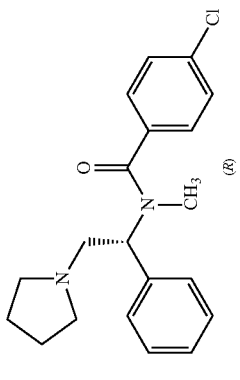
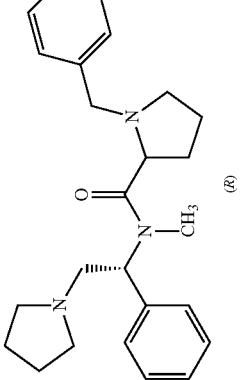

TABLE 7-continued

Specific Embodiments.

| PDSP No. | SMDC No. | Cmpd. Alias | KOR | KOR Ki | DOR | DOR Ki | MOR | MOR Ki | NOP Tango Agonist | MW | MW as Salt |
|---|---|---|---|---|---|---|---|---|---|---|---|

Int-S01

TABLE 7-continued

Specific Embodiments.

| PDSP No. | SMDC No. | Cmpd. Alias | KOR | KOR Ki | DOR | DOR Ki | MOR | MOR Ki | NOP Tango Agonist | MW | MW as Salt |
|---|---|---|---|---|---|---|---|---|---|---|---|

TABLE 7-continued
Specific Embodiments.
| PDSP No. | SMDC No. | Cmpd. Alias | KOR | KOR Ki | DOR | DOR Ki | MOR | MOR Ki | NOP Tango Agonist | MW | MW as Salt |
|---|---|---|---|---|---|---|---|---|---|---|---|
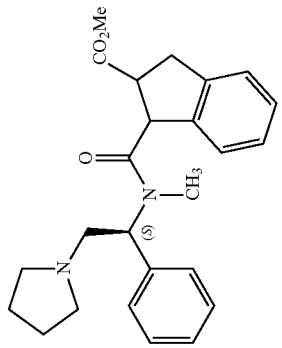
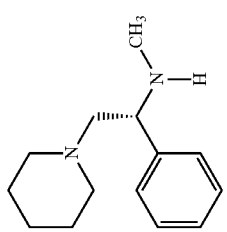
Int-R02
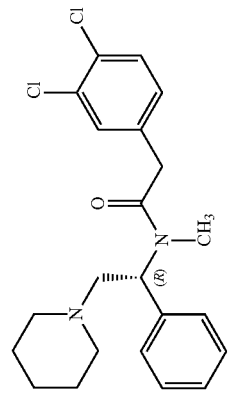

TABLE 7-continued

Specific Embodiments.

| PDSP No. | SMDC No. | Cmpd. Alias | KOR | KOR Ki | DOR | DOR Ki | MOR | MOR Ki | NOP Tango Agonist | MW | MW as Salt |
|---|---|---|---|---|---|---|---|---|---|---|---|

TABLE 7-continued

Specific Embodiments.

| PDSP No. | SMDC No. | Cmpd. Alias | KOR | KOR Ki | DOR | DOR Ki | MOR | MOR Ki | NOP Tango Agonist | MW | MW as Salt |
|---|---|---|---|---|---|---|---|---|---|---|---|

TABLE 7-continued

Specific Embodiments.

| PDSP No. | SMDC No. | Cmpd. Alias | KOR | KOR Ki | DOR | DOR Ki | MOR | MOR Ki | NOP Tango Agonist | MW | MW as Salt |
|---|---|---|---|---|---|---|---|---|---|---|---|

Int-S02

TABLE 7-continued

Specific Embodiments.

| PDSP No. | SMDC No. | Cmpd. Alias | KOR | KOR Ki | DOR | DOR Ki | MOR | MOR Ki | NOP Tango Agonist | MW | MW as Salt |
|---|---|---|---|---|---|---|---|---|---|---|---|

TABLE 7-continued

Specific Embodiments.

| PDSP No. | SMDC No. | Cmpd. Alias | KOR | KOR Ki | DOR | DOR Ki | MOR | MOR Ki | NOP Tango Agonist | MW | MW as Salt |
|---|---|---|---|---|---|---|---|---|---|---|---|

EMBODIMENTS

Embodiment 1

A compound, or pharmaceutically acceptable salt thereof, having the formula:

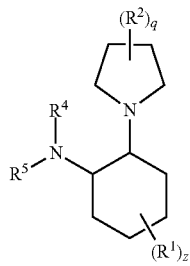

(I)

wherein q is an integer from 0 to 4; z is an integer from 0 to 4; $R^1$, $R^2$ and $R^4$ are independently hydrogen, halogen, —$N_3$, —$CF_3$, —$CCl_3$, —OH, —SH, —$NH_2$, —C(O)$NH_2$, —C(O)OH, —CN, —$NO_2$, —$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; and $R^4$ and $R^5$ are optionally joined together to form a substituted or unsubstituted heterocycloalkyl or substituted or unsubstituted heteroaryl; or $R^5$ is —C(O)-$L^1$-$R^3$ or $R^3$-substituted or unsubstituted alkyl, wherein $L^1$ is a bond or substituted or unsubstituted alkylene and $R^3$ is substituted or unsubstituted cycloalkyl, substituted or unsubstituted heterocycloalkyl, substituted or unsubstituted aryl or substituted or unsubstituted heteroaryl.

Embodiment 2

The compound of embodiment 1, wherein said compound has the formula:

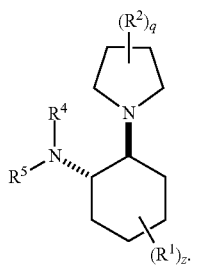

(IA)

Embodiment 3

The compound of embodiment 1 or 2 wherein $R^4$ and $R^5$ are joined together to form a substituted or unsubstituted heteroaryl or substituted or unsubstituted heterocycloalkyl.

Embodiment 4

The compound of one of embodiments 1 to 3, wherein $R^4$ and $R^5$ are joined together to form a substituted or unsubstituted benzimidizolone.

Embodiment 5

A compound, or pharmaceutically acceptable salt thereof, having the formula:

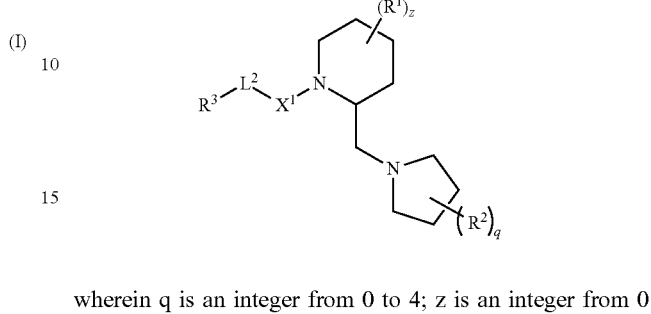

(II)

wherein q is an integer from 0 to 4; z is an integer from 0 to 4; $X^1$ is —C(O)— or substituted or unsubstituted alkylene; $L^2$ is a bond, —N(H)—C(O)—, —C(O)— or substituted or unsubstituted alkylene; $R^1$ and $R^2$ are independently hydrogen, halogen, —$N_3$, —$CF_3$, —$CCl_3$, —OH, —SH, —$NH_2$, —C(O)$NH_2$, —C(O)OH, —CN, —$NO_2$, —$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; and $R^3$ is substituted or unsubstituted cycloalkyl, substituted or unsubstituted heterocycloalkyl, substituted or unsubstituted aryl or substituted or unsubstituted heteroaryl.

Embodiment 6

The compound of embodiment 5, having the formula:

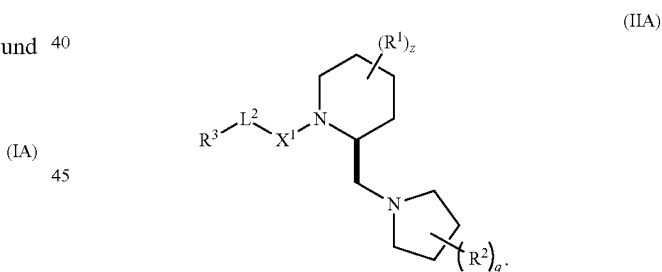

(IIA)

Embodiment 7

The compound of embodiment 5 or 6, wherein $X^1$ is —C(O)— or substituted or unsubstituted ($C_1$ to $C_3$) alkylene.

Embodiment 8

The compound of embodiment 5 or 6, wherein $X^1$ is —C(O)— or unsubstituted ($C_1$ to $C_3$) alkylene.

Embodiment 9

The compound of embodiment 5 or 6, wherein $X^1$ is —C(O)— or methylene.

Embodiment 10

The compound of embodiment 5 or 6, wherein $X^1$ is —C(O)—.

Embodiment 11

The compound of one of embodiments 5 to 10, wherein $L^2$ is a bond, —N(H)—C(O)—, —C(O)— or substituted or unsubstituted ($C_1$ to $C_3$) alkylene.

Embodiment 12

The compound of one of embodiments 5 to 10, wherein $L^2$ is a bond, —N(H)—C(O)—, —C(O)— or unsubstituted ($C_1$ to $C_3$) alkylene.

Embodiment 13

The compound of one of embodiments 5 to 10, wherein $L^2$ is a bond, —N(H)—C(O)—, —C(O)— or methylene.

Embodiment 14

The compound of one of embodiments 5 to 10, wherein $L^2$ is a bond or methylene.

Embodiment 15

The compound of embodiment 5 wherein $X^1$ is substituted or unsubstituted alkylene and $L^1$ is —N(H)—C(O)—.

Embodiment 16

A compound, or pharmaceutically acceptable salt thereof, having the formula:

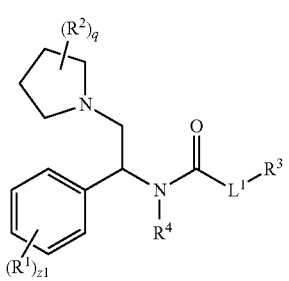

(III)

wherein q is an integer from 0 to 4; z1 is an integer from 0 to 5; $R^1$ and $R^2$ are independently hydrogen, halogen, —$N_3$, —$CF_3$, —$CCl_3$, —OH, —SH, —$NH_2$, —C(O)$NH_2$, —C(O)OH, —CN, —$NO_2$, —$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; $L^1$ is a bond or substituted or unsubstituted alkylene; and $R^3$ is substituted or unsubstituted cycloalkyl, substituted or unsubstituted heterocycloalkyl, substituted or unsubstituted aryl or substituted or unsubstituted heteroaryl.

Embodiment 17

The compound of embodiment 16, having the formula:

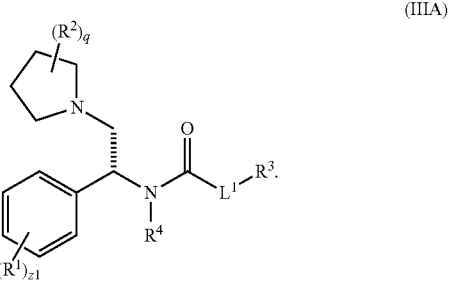

(IIIA)

Embodiment 18

The compound of embodiment 16, having the formula:

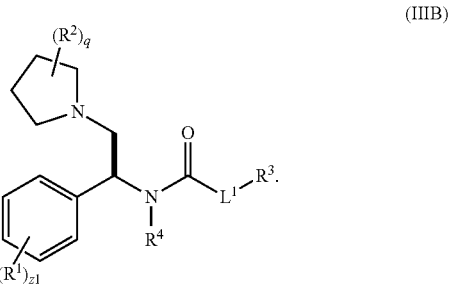

(IIIB)

Embodiment 19

A compound, or pharmaceutically acceptable salt thereof, having the formula:

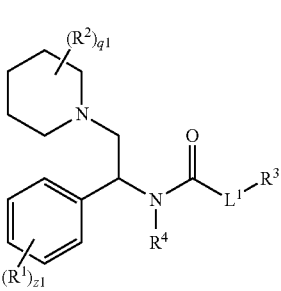

(IV)

wherein q1 is an integer from 0 to 5; z1 is an integer from 0 to 5; $R^1$ and $R^2$ are independently hydrogen, halogen, —$N_3$, —$CF_3$, —$CCl_3$, —OH, —SH, —$NH_2$, —C(O)$NH_2$, —C(O)OH, —CN, —$NO_2$, —$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; $L^1$ is a bond or substituted or unsubstituted alkylene; and $R^3$ is substituted or unsubstituted cycloalkyl, substituted or unsubstituted heterocycloalkyl, substituted or unsubstituted aryl or substituted or unsubstituted heteroaryl.

Embodiment 20

The compound of embodiment 19, having the formula:

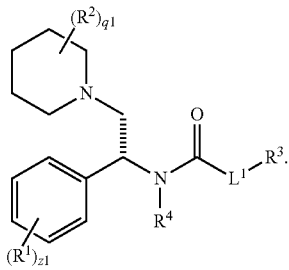

(IVA)

Embodiment 21

The compound of embodiment 19, having the formula:

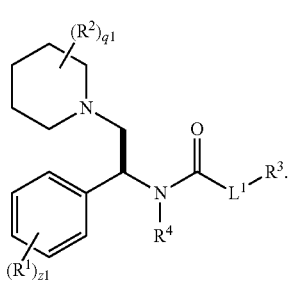

(IVB)

Embodiment 22

The compound of one of embodiments 1 to 21, wherein q is 1, q1 is 1, z is 1 and z1 is 1.

Embodiment 23

The compound of one of embodiments 1 to 21, wherein $R^1$ and $R^2$ are hydrogen or substituted or unsubstituted alkyl.

Embodiment 24

The compound of one of embodiments 1 to 21, wherein $R^1$ and $R^2$ are hydrogen.

Embodiment 25

The compound of one of embodiments 1 to 24 wherein $R^4$ is hydrogen or substituted or unsubstituted alkyl.

Embodiment 26

The compound of one of embodiments 1 to 24 wherein $R^4$ is hydrogen or methyl.

Embodiment 27

The compound of one of embodiments 1 to 26, wherein $R^3$ is $R^{3A}$-substituted or unsubstituted cycloalkyl, $R^{3A}$-substituted or unsubstituted heterocycloalkyl, $R^{3A}$-substituted or unsubstituted aryl or $R^{3A}$-substituted or unsubstituted heteroaryl; $R^{3A}$ is $R^{3B}$-substituted or unsubstituted alkyl, $R^{3B}$-substituted or unsubstituted heteroalkyl, $R^{3B}$-substituted or unsubstituted cycloalkyl, $R^{3B}$-substituted or unsubstituted heterocycloalkyl, $R^{3B}$-substituted or unsubstituted aryl or $R^{3B}$-substituted or unsubstituted heteroaryl; $R^{3B}$ is $R^{3C}$-substituted or unsubstituted cycloalkyl, $R^{3C}$-substituted or unsubstituted heterocycloalkyl, $R^{3C}$-substituted or unsubstituted aryl or $R^{3C}$-substituted or unsubstituted heteroaryl; $R^{3C}$ is halogen, —OH, —NH$_2$, —SH, —C(O)OH, —C(O)NH$_2$, —CF$_3$, —CCl$_3$, —CN, —N$_3$, unsubstituted alkyl, unsubstituted heteroalkyl, unsubstituted cycloalkyl, unsubstituted heterocycloalkyl, unsubstituted aryl or unsubstituted heteroaryl.

Embodiment 28

The compound of embodiment 27, wherein $R^{3A}$ is $R^{3B}$-substituted or unsubstituted alkyl, $R^{3B}$-substituted or unsubstituted cycloalkyl, $R^{3B}$-substituted or unsubstituted heterocycloalkyl, $R^{3B}$-substituted or unsubstituted aryl or $R^{3B}$-substituted or unsubstituted heteroaryl.

Embodiment 29

The compound of embodiment 27, wherein $R^{3A}$ is $R^{3B}$-substituted or unsubstituted cycloalkyl, $R^{3B}$-substituted or unsubstituted heterocycloalkyl, $R^{3B}$-substituted or unsubstituted aryl or $R^{3B}$-substituted or unsubstituted heteroaryl.

Embodiment 30

The compound of one of embodiments 1 to 29, wherein $R^3$ is not substituted or unsubstituted aryl.

Embodiment 31

The compound of one of embodiments 1 to 29, wherein $R^3$ is not substituted or unsubstituted phenyl.

Embodiment 32

The compound of one of embodiments 1 to 29, wherein $R^3$ is not unsubstituted phenyl.

Embodiment 33

The compound of one of embodiments 1 to 29, wherein $R^3$ is not substituted phenyl.

Embodiment 34

The compound of one of embodiments 1 to 29, wherein $R^3$ is not chloro-substituted phenyl.

Embodiment 35

A pharmaceutical composition comprising a pharmaceutically acceptable excipient and a compound of any one of embodiments 1-34.

Embodiment 36

A method of treating pain in a subject in need thereof; said method comprising administering to said subject a therapeutically effective amount of a compound of any one of embodiments 1-34.

Embodiment 37

The method of embodiment 36, wherein said administering is performed after completion of surgery on said subject.

Embodiment 38

The method of embodiment 36 or 37, wherein said subject is male.

Embodiment 39

The method of one of embodiments 36 to 38, wherein said compound is a delta opioid receptor agonist, a kappa opioid receptor agonist or a mu opioid receptor agonist.

Embodiment 40

The method of one of embodiments 36 to 38, wherein said compound is a kappa opioid receptor agonist.

Embodiment 41

The method of one of embodiments 36 to 40, wherein said compound is a NOP receptor antagonist.

Embodiment 42

The method of one of embodiments 36 to 40, wherein said compound is not a NOP receptor agonist.

Embodiment 43

The method of one of embodiments 36 to 40, wherein said compound is a low-affinity NOP receptor binder.

Embodiment 44

A method of inhibiting a nociceptin (NOP) receptor, said method comprising contacting a NOP receptor with an effective amount of a compound of any one of embodiments 1-34, thereby inhibiting said NOP receptor.

Embodiment 45

The method of embodiment 44, wherein said method further comprises contacting said compound with an opioid receptor thereby activating said opioid receptor, wherein said opioid receptor is a delta opioid receptor, a kappa opioid receptor or a mu opioid receptor.

Embodiment 46

A method of activating an opioid receptor, said method comprising contacting an opioid receptor with an effective amount of a compound of any one of embodiments 1-34, thereby activating said opioid receptor, wherein said opioid receptor is a delta opioid receptor, a kappa opioid receptor or a mu opioid receptor.

Embodiment 47

A method of determining whether a test compound elicits an analgesic effect in a human male subject and does not elicit an anti-analgesic effect in a human male subject, the method comprising: (a) administering a test compound to a human male subject; (b) determining whether said test compound elicits an analgesic effect in said human male subject at a first time point; (c) determining whether said test compound elicits an anti-analgesic effect in said human male subject at a second time point thereby determining whether a test compound elicits an analgesic effect in a human male subject and does not elicit an anti-analgesic effect in a human male subject.

Embodiment 48

The method of embodiment 47, wherein said second time point is at least 70 minutes after said administering.

Embodiment 49

The method of embodiment 47, wherein said second time point is at least about 90 minutes after said administering.

Embodiment 50

The method of embodiment 47, wherein said second time point is at least about 110 minutes after said administering.

Embodiment 51

The method of embodiment 47, further comprising, prior to said administering, determining whether said test compound binds to a NOP receptor.

What is claimed is:

1. A method of producing sexually dimorphic analgesia in a male subject in need thereof, the method comprising administering to the male subject a therapeutically effective amount of a compound having the formula:

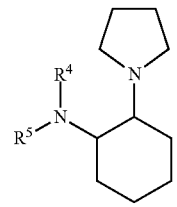

or a pharmaceutically acceptable salt thereof; wherein $R^4$ is hydrogen or methyl; $R^5$ is —C(O)-$L^1$-$R^3$; $L^1$ is a bond, —CH$_2$—, —CH$_2$CH$_2$—, or —CH$_2$CH$_2$CH$_2$—; and $R^3$ is (i) an unsubstituted 5-membered heterocyloalkyl; (ii) an unsubstituted 6-membered heterocycloalkyl; (iii) a 5-membered heterocyloalkyl substituted with one or two substituents selected from the group consisting of =O, halogen, —OH, —NH$_2$, —SH, —C(O)OH, —C(O)NH$_2$, —CF$_3$, —CCl$_3$, —CN, —N$_3$, an unsubstituted $C_1$-$C_8$ alkyl, and benzyl; or (iv) a 6-membered heterocycloalkyl.

2. The method of claim 1, wherein $R^3$ is (i) an unsubstituted 5-membered heterocyloalkyl containing one nitrogen heteroatom; (ii) an unsubstituted 6-membered heterocycloalkyl containing one nitrogen heteroatom; (iii) a 5-membered heterocyloalkyl containing one nitrogen heteroatom and one or two substituents selected from the group consisting of =O, halogen, —OH, —NH$_2$, —SH, —C(O)OH, —C(O)NH$_2$, —CF$_3$, —CCl$_3$, —CN, —N$_3$, an unsubstituted $C_1$-$C_8$ alkyl, and a benzyl; or (iv) a 6-membered heterocycloalkyl containing one nitrogen heteroatom and one or two substituents selected from the group consisting of =O, halogen, —OH, —NH$_2$, —SH, —C(O)OH, —C(O)NH$_2$, —CF$_3$, —CCl$_3$, —CN, —N$_3$, an unsubstituted C$_1$-C$_8$ alkyl, a benzyl, and an indene moiety.

3. The method of claim 1, wherein R$^3$ is a 5-membered heterocyloalkyl containing one nitrogen heteroatom and one or two substituents selected from the group consisting of =O, —OH, —NH$_2$, benzyl, methyl, and ethyl; or a 6-membered heterocycloalkyl containing one nitrogen heteroatom and one or two substituents selected from the group consisting of =O, —OH, —NH$_2$, methyl, ethyl, benzyl, and an indene moiety.

4. The method of claim 1, wherein the compound is of the formula:

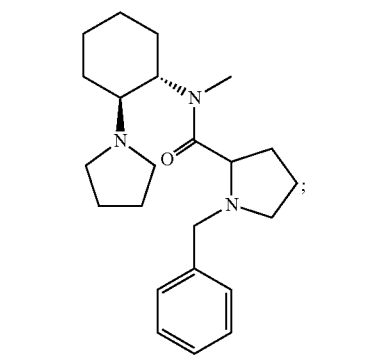

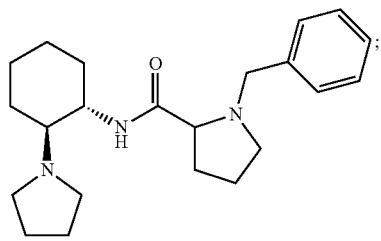

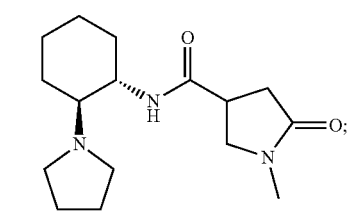

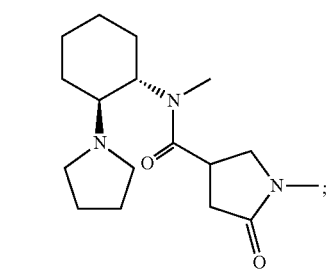

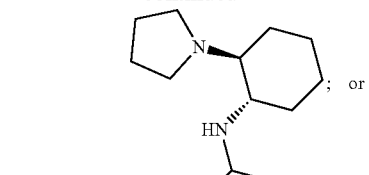

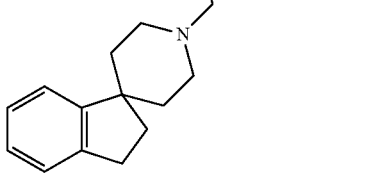

-continued

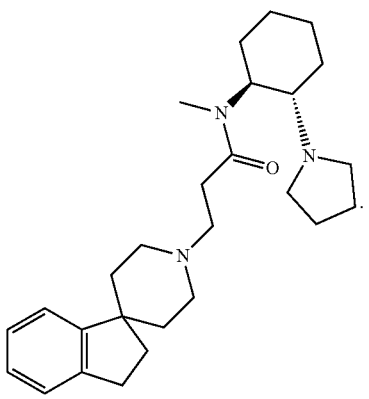 [SMILES: CN(C(=O)CCN1CCC2(CCc3ccccc32)CC1)[C@H]1CCCC[C@@H]1N1CCCC1]

5. The method of claim 4, wherein the compound is of the formula:

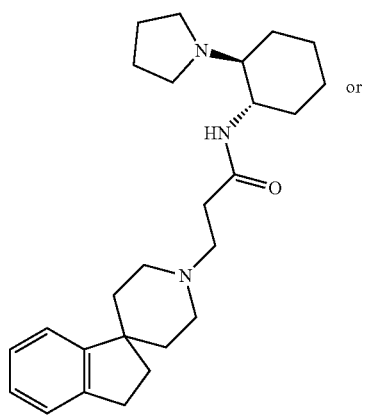

133
-continued
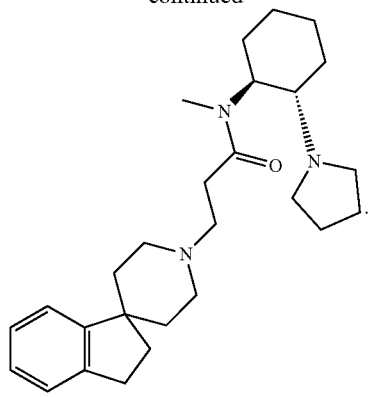
134
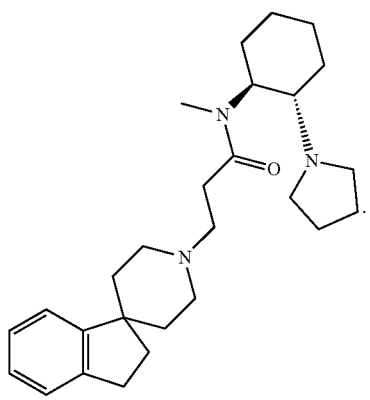 [SMILES: CN(C(=O)CCN1CCC2(CCc3ccccc32)CC1)[C@H]1CCCC[C@@H]1N1CCCC1]
6. The method of claim 5, wherein the compound is of the formula:
* * * * *